United States Patent

Takemura et al.

Patent Number: 5,849,757
Date of Patent: Dec. 15, 1998

[54] PYRIDONECARBOXYLIC ACID DERIVATIVES SUBSTITUTED BY A BICYCLIC AMINO GROUP AS ANTIBACTERIALS

[75] Inventors: Makoto Takemura; Youichi Kimura; Katsuhiro Kawakami; Kenichi Kimura; Hitoshi Ohki; Norikazu Matsuhashi; Haruko Kawato, all of Tokyo, Japan

[73] Assignee: Daiichi Pharmaceutical Co., Ltd., Tokyo, Japan

[21] Appl. No.: 875,678

[22] PCT Filed: Feb. 1, 1996

[86] PCT No.: PCT/JP96/00208

§ 371 Date: Aug. 4, 1997

§ 102(e) Date: Aug. 4, 1997

[87] PCT Pub. No.: WO96/23782

PCT Pub. Date: Aug. 8, 1996

[30] Foreign Application Priority Data

| Feb. 2, 1995 | [JP] | Japan | 7-015614 |
| Feb. 7, 1995 | [JP] | Japan | 7-019478 |
| Feb. 7, 1995 | [JP] | Japan | 7-019481 |

[51] Int. Cl.$^6$ ............ C07D 401/04; C07D 471/04; A61K 31/435; A61K 31/47
[52] U.S. Cl. ............ 514/312; 546/156
[58] Field of Search ............ 546/156; 514/312

[56] References Cited

U.S. PATENT DOCUMENTS 4,649,144  3/1987  Matsumoto et al. ............ 514/300

FOREIGN PATENT DOCUMENTS

| 0 343 524 A | 11/1989 | European Pat. Off. |  |
| 413 455 | 2/1991 | European Pat. Off. |  |
| 0 550 016 A1 | 7/1993 | European Pat. Off. | C07D 401/04 |
| 0 550 025 A1 | 7/1993 | European Pat. Off. | C07D 209/54 |
| 0 593 766 A1 | 4/1994 | European Pat. Off. |  |
| 57-72981 | 5/1982 | Japan | C07D 471/04 |
| 60-260577 | 12/1985 | Japan | C07D 471/04 |
| 64-56673 | 3/1989 | Japan | C07D 403/04 |
| 3-86875 | 4/1991 | Japan | C07D 401/04 |
| WO 9521163 | 8/1995 | WIPO. |  |

Primary Examiner—Mukund J. Shah
Assistant Examiner—Bruck Kifle
Attorney, Agent, or Firm—Sughrue, Mion, Zinn, Macpeak & Seas, PLLC

[57] ABSTRACT

This invention relates to a $N_1$-(halogenocyclopropyl)-substituted pyridonecarboxylic acid derivative represented by the following formula (I):

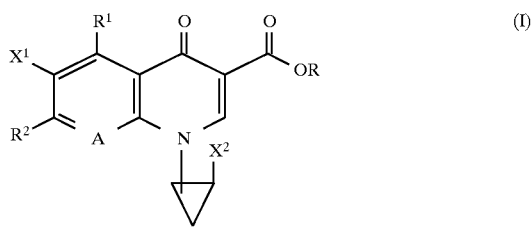

wherein $X^1$ is a halogen atom or a hydrogen atom; $X^2$ is a halogen atom; $R^1$ is a hydrogen atom, a hydroxyl group, a thiol group, a halogenomethyl group, an amino group, an alkyl group or an alkoxy group which may have a substituent group; $R^2$ is a group represented by the following formula (II):

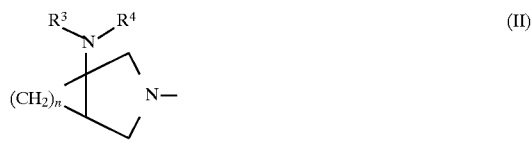

wherein $R^3$ and $R^4$ are independently a hydrogen atom or an alkyl group and n is an integer of 1 or 2; A is a nitrogen atom or a partial structure of the following formula (III):

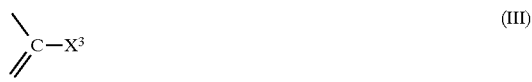

wherein $X^3$ is a hydrogen atom, a halogen atom, a cyano group, an amino group, an alkyl group, a halogenomethyl group, an alkoxyl group or a halogenomethoxyl group which may have a substituent group; and R is a hydrogen atom, a phenyl group, an acetoxymethyl group, a pivaloyloxymethyl group, an ethoxycarbonyl group, a choline group, a dimethylaminoethyl group, a 5-indanyl group, a phthalidynyl group, a 5-alkyl-2-oxo-1,3-dioxol-4-ylmethyl group, a 3-acetoxy-2-oxobutyl group, an alkyl group, an alkoxymethyl group or a phenylalkyl group, and provides a heterocyclic compound useful as antibacterial drugs.

7 Claims, No Drawings

PYRIDONECARBOXYLIC ACID DERIVATIVES SUBSTITUTED BY A BICYCLIC AMINO GROUP AS ANTIBACTERIALS

TECHNICAL FIELD

This invention relates to an antibacterial compound useful as medicines, animal drugs, fisheries drugs or antibacterial preservatives and to an antibacterial drug or antibacterial preparation which contains the same.

BACKGROUND ART

Though quinolone derivatives having 1-amino-3-azabicyclo[3.2.0]heptan-3-yl group as a substituent are disclosed in JP-A-64-56673 and JP-A-3-86875 (the term "JP-A" as used herein means an "unexamined published Japanese patent application"), nothing is known about the quinolone derivative of the present invention which has the substituent derived from this amino-substituted condensed-bicyclic heterocyclic compound and also has a halogenocyclopropyl group at the 1-position.

Synthetic quinolone antibacterial agents having not only antibacterial activities but also excellent biological distribution such as oral absorbability, distribution into organs, urinary excretion ratio and the like have been found in recent years, and a number of such compounds are now supplied to the clinical field as chemotherapeutic agents effective against various infectious diseases. However, the presence of bacterial strains having low sensitivity to these drugs has been increasing in recent years in the clinical field. Also, like the case of *Staphylococcus aureus* (MRSA) having less sensitivity against β-lactam antibiotics, strains having low sensitivity to synthetic quinolone antibacterial agents are increasing even among strains which are resistant to other drugs than synthetic quinolone antibacterial agents. In consequence, development of drugs having more higher efficacy has been called for in the clinical field.

DISCLOSURE OF INVENTION

The inventors of the present invention think that structures of the 7- and 1-position substituents are greatly concerned in the antibacterial activity, efficacy and safety of synthetic quinolone antibacterial agents. In consequence, the present inventors have conducted intensive studies to obtain a compound having high antibacterial activity against a broad range of bacteria including quinolone-resistant strains and found as the results that a quinolone derivative having a substituent group derived from an amino-substituted condensed-bicyclic heterocyclic compound at the 7-position shows strong antibacterial activity against Gram-positive and Gram-negative bacteria, particularly quinolone-resistant bacteria including MRSA, and that not only the antibacterial activity but also excellent efficacy and safety can be obtained by a quinolone derivative in which the 1-position is substituted with a halogenocyclopropyl group, particularly a fluorocyclopropyl group.

In the quinolone derivative of the present invention, a pair of enantiomer is attributed only to the 1-positioned halogenocyclopropane ring moiety even in the absence of stereoisomerism in other substituents. This is originated from a stereochemical relationship between pyridonecarboxylic acid moiety and halogen atom on the cyclopropane ring. When isomers formed in this way are racemic, these derivative is a mixture of enantiomers which could be used as a medicine as such.

On the other hand, when stereoisomerism is also present at other positions, particularly at the 7-position substitutent, in addition to the stereoisomerism of the halogenocyclopropene ring moiety, such quinolone derivative consists of diastereomers, meaning that 4 or more stereoisomers are present. Since the mixture of diastereomers is a mixture of compounds having different physical properties, it is difficult to administer the mixture as a medicine.

The present inventors have made intensive efforts to obtain a quinoline compound consisting of a single stereoisomer even in the case of a 1-(1,2-cis-2-halogenocyclopropyl)-substituted quinolone derivative which consists of diastereomers.

As the results, the present inventors have succeeded in obtaining each enantiomer of cis-2-fluorocyclopropylamine as a pure compound. The present inventors have also succeeded in obtaining each of the fluorocyclopropane ring-originated enantiomers of the quinolone derivative as a compound consisting of single isomer, from the pure cis-fluorocyclopropylamine. The present inventors have also succeeded in obtaining each isomer of an amino-substituted condensed-bicyclic heterocyclic compound having an asymmetric carbon atom and a nitrogen as the hetero atom, as a pure compound.

The success in obtaining such quinolone derivative and amino-substituted condensed-bicyclic heterocyclic compound having a nitrogen atom as a hetero atom, both useful as synthetic intermediates, has rendered possible synthesis of a stereochemically single quinolone derivative composed of single diastereomer.

Thereafter, the present invention has been accomplished on the basis of a finding that the novel quinolone derivative of the present invention which has a group derived from the amino-substituted condensed-bicyclic heterocyclic compound at the 7-position and the halogenocyclopropyl group at the 1-position is a compound which is highly safe and shows excellent activity against a broad range of bacterial species including quinolone-resistant strains.

Accordingly, the present invention relates to an $N_1$-(halogenocyclopropyl)-substituted pyridonecarboxylic acid derivative represented by formula (I):

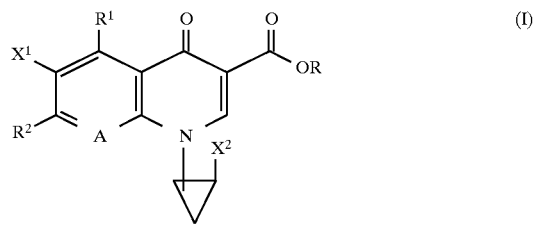

wherein $X^1$ represents a halogen atom or a hydrogen atom;

$X^2$ represents a halogen atom;

$R_1$ represents a hydrogen atom, a hydroxyl group, a thiol group, a halogenomethyl group, an amino group, an alkyl group having 1 to 6 carbon atoms or an alkoxy group having 1 to 6 carbon atoms, of which the amino group may have a substituent selected from the group consisting of a formyl group, an alkyl group having 1 to 6 carbon atoms and an acyl group having 2 to 5 carbon atoms, with the proviso that the amino group may be dialkyl-substituted when the substituent is alkyl groups which may be the same or different from each other;

$R^2$ represents a group having a structure derived from an amino-substituted condensed-bicyclic heterocyclic compound, represented by formula (II):

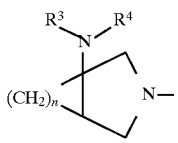

wherein $R^3$ and $R^4$ independently represent a hydrogen atom or an alkyl group having 1 to 6 carbon atoms and n is an integer of 1 or 2;

A represents a nitrogen atom or a partial structure of formula (III):

wherein $X^3$ represents a hydrogen atom, a halogen atom, a cyano group, an amino group, an alkyl group having 1 to 6 carbon atoms, a halogenomethyl group, an alkoxyl group having 1 to 6 carbon atoms or a halogenomethoxyl group, of which the amino group may have a substituent selected from the group consisting of a formyl group, an alkyl group having 1 to 6 carbon atoms and an acyl group having 2 to 5 carbon atoms, with the proviso that the amino group may be dialkyl-substituted when the substituent is alkyl groups which may be the same or different from each other; and R represents a hydrogen atom, a phenyl group, an acetoxymethyl group, a pivaloyloxymethyl group, an ethoxycarbonyl group, a choline group, a dimethylaminoethyl group, a 5-indanyl group, a phthalidynyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group; or a salt thereof.

The present invention also relates to the aforementioned compound or a salt thereof, in which the halogenocyclopropyl group in the formula (I) is a 1,2-cis-2-halogenocyclopropyl group.

The present invention also relates to the aforementioned compound or a salt thereof, in which $R^2$ in the formula (I) is a stereochemically pure substituent.

The present invention also relates to the aforementioned compound or a salt thereof, in which the halogenocyclopropyl group in the formula (I) is a stereochemically pure substituent.

The present invention also relates to the aforementioned compound or a salt thereof, in which the halogenocyclopropyl group is a (1R,2S)-2-halogenocyclopropyl group.

The present invention also relates to the aforementioned compound or a salt thereof, in which $X^2$ is a fluorine atom.

The present invention also relates to an antibacterial drug which contains the aforementioned compound of the formula (I) or a salt thereof as an active ingredient.

The following describes substituents of the compound of the present invention represented by the formula (I).

When each of $X_1$, $X^2$ and $X^3$ is a halogen atom, $X^1$ and $X^2$ are most preferably a fluorine atom and $X^3$ is preferably a fluorine atom or a chlorine atom.

$R^1$ is a hydrogen atom, a hydroxyl group, a thiol group, a halogenomethyl group, an amino group, an alkyl group having 1 to 6 carbon atoms or an alkoxy group having 1 to 6 carbon atoms, of which the amino group may have a formyl group, an alkyl group having 1 to 6 carbon atoms or an acyl group having 2 to 5 carbon atoms as a substituent, with the proviso that the amino group may be dialkyl-substituted when the substituent is alkyl groups which may be the same or different from each other.

As for $R^1$, the alkyl group may be straight or branched-chain alkyl groups having 1 to 6 carbon atoms, but is preferably methyl, ethyl, n-propyl or isopropyl group.

As the halogen atom of the halogenomethyl group, a fluorine atom is particularly preferred and the number of the atom may be 1 to 3. Preferred examples of the halogenomethyl group include a fluoromethyl group and a difluoromethyl group.

When $R^1$ is an amino group, a hydroxyl group or a thiol group, these groups may be protected with ordinarily used protective groups.

Examples of such protective groups include alkoxycarbonyl groups such as tertiary butoxycarbonyl, 2,2,2-trichloroethoxycarbonyl and the like, aralkyloxycarbonyl groups such as benzyloxycarbonyl, paramethoxybenzyloxycarbonyl, paranitrobenzyloxycarbonyl and the like, acyl groups such as acetyl, methoxyacetyl, trifluoroacetyl, chloroacetyl, pivaloyl, formyl, benzoyl and the like, alkyl or aralkyl groups such as tertiary butyl, benzyl, paranitrobenzyl, paramethoxybenzyl, triphenylmethyl and the like, ethers such as methoxymethyl, tertiary buyoxymethyl, tetrahydropyranyl, 2,2,2-trichloroethoxymethyl and the like, and silyl groups such as trimethylsilyl, isopropyldimethylsilyl, tertiary butyldimethylsilyl, tribenzylsilyl, tertiary butyldiphenylsilyl and the like.

Of these protective groups, ethers and silyl groups may be used preferably as protective groups for a hydroxyl group and a thiol group, and other protective groups can be used as protecting groups of any one of an amino group, a hydroxyl group and a thiol group.

$X^3$ is a hydrogen atom, a halogen atom, a cyano group, an amino group, an alkyl group having 1 to 6 carbon atoms, a halogenomethyl group, an alkoxyl group having 1 to 6 carbon atoms or a halogenomethoxyl group, of which the amino group may have a formyl group, an alkyl group having 1 to 6 carbon atoms or an acyl group having 2 to 5 carbon atoms as a substituent, with the proviso that the amino group may be dialkyl-substituted when the substituent is alkyl groups which may be the same or different from each other.

As for $X^3$, the alkyl group may be straight or branched-chain alkyl groups having 1 to 6 carbon atoms, but is preferably methyl, ethyl, n-propyl or isopropyl group.

As the halogen atom of the halogenomethyl group, a fluorine atom is particularly preferred and the number of the atom may be 1 to 3. Preferred examples of the halogenomethyl group include a fluoromethyl group and a difluoromethyl group.

The alkoxyl group may have 1 to 6 carbon atoms and is preferably a methoxyl group.

As the halogen atom of the halogenomethyl group, fluorine atom is particularly preferred and the number of the atom may be 1 to 3.

When A is a partial structure represented by the following formula (III),

preferred combination of $R^1$ and $X^3$ is that $R^1$ is an amino group, a hydrogen atom, a hydroxyl group or an alkyl group having 1 to 6 carbon atoms and $X^3$ is an alkyl group having 1 to 6 carbon atoms, an alkoxyl group having 1 to 6 carbon atoms, a halogen atom, a halogenomethoxyl group or a hydrogen atom.

In more preferred combination, $R^1$ is an amino group, a hydrogen atom, a hydroxyl group or a methyl group and $X^3$ is a methyl group, a methoxyl group, a fluorine atom, a chlorine atom, a difluoromethoxyl group or a hydrogen atom.

In most preferred combination, $R^1$ is an amino group, a hydrogen atom, a hydroxyl group or a methyl group and $X^3$ is a methyl group or a methoxyl group.

To these $R^1$ and $X^3$ groups, $X^1$ and $X^2$ are preferably fluorine atoms.

$R^2$ is a group represented by the following formula (II)

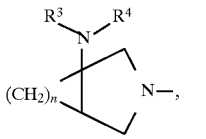

(II)

which is derived from an amino-substituted condensed-bicyclic heterocyclic compound represented by the following formula

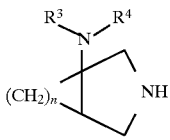

(though a case in which the 5-membered ring nitrogen is hydrogen-substituted is shown herein, it may be substituted with other substituent such as a protective group for nitrogen atom). This group has an amino group as a substituent on the bridge head carbon atom. In consequence, this moiety seems to have a small-membered alicyclic cyclic amine structure, so that the present inventors think that this structure is taking an important role for the appearance of the excellent properties of the compound of the present invention.

The term "condensed-bicyclic heterocyclic compound" as used herein means a compound which has a structure formed by the replacement of a ring structure-forming carbon atom of a condensed-bicyclic hydrocarbon compound by a hetero atom such as a nitrogen atom or the like:

In the above formula, $R^3$ and $R^4$ independently represent a hydrogen atom or an alkyl group having 1 to 6 carbon atoms and n is an integer of 1 or 2. The alkyl group may be either straight or branched chain having 1 to 6 carbon atoms, and is preferably a methyl group.

Also, $R^3$ and $R^4$ may be combined to from a methylene chain having 2 to 6 carbon atoms and a ring structure including a nitrogen atom to which $R^3$ and $R^4$ are bonded.

In a preferred combination of $R^3$ and $R^4$, one of $R^3$ and $R^4$ is a hydrogen atom and the other is an alkyl group having 1 to 6 carbon atoms.

In a more preferred combination, one of $R^3$ and $R^4$ is a hydrogen atom and the other is a methyl group or an ethyl group.

Also, n is an integer of 1 or 2.

The present inventors have found that the following groups are also preferable as the substituent $R^2$.

It is known that a quinolone derivative, which has 3-aminomethylpyrrolidine as a substituent, shows strong antibacterial activity against Gram-positive bacteria. For example, a 7-(3-aminomethylpyrrolidinyl)quinolonecarboxylic acid derivative is disclosed in *Journal of Medicinal Chemistry*, vol. 29, p. 445 (1986), and a 7-[3-(1-amino-1-methylethyl)pyrrolidinyl] quinolonecarboxylic acid derivative is disclosed in *Journal of Medicinal Chemistry*, vol. 37, p. 733 (1994).

On the other hand, though quinolone derivatives having a 3-aminoalkylpyrrolidinyl group on the 7-position show strong antibacterial activity against Gram-negative and Gram-positive bacteria, many of these compounds act upon not only bacteria but also eucaryotic cells because of their low selective toxicity, so that it is difficult to use them as medicines or animal drugs.

The present inventors have conducted intensive studies on quinolone derivatives having a 3-aminoalkylpyrrolidinyl group on the 7-position. As the result, it has been found that a quinolone derivative having high antibacterial activity, excellent safety and high selective toxicity can be obtained when both of its 5- and 8-positions of the quinolone skeleton are substituent groups other than a hydrogen atom.

That is, the 3-aminoalkylpyrrolidinyl group is preferable, a pyrrolidinyl group having an aminoalkyl group on its 3-position represented by the following formula (IV)

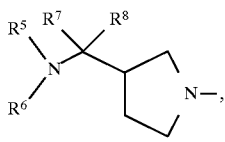

(IV)

which is derived from a 3-aminoalkylpyrrolidine compound represented by the following formula

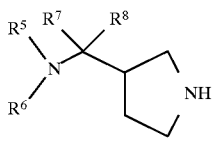

(though a case in which the pyrrolidine nitrogen atom is hydrogen-substituted is shown herein, it may be substituted with other substituent such as a protective group for nitrogen atom).

In the above formulae, $R^5$ and $R^6$ independently represent a hydrogen atom or an alkyl group having 1 to 3 carbon atoms. The alkyl group may be either straight or branched chain, and is preferably a methyl group or an ethyl group.

Also, $R^5$ and $R^6$ may be combined to from a methylene chain having 2 to 6 carbon atoms and a ring structure including a nitrogen atom bonded to $R^5$ and $R^6$.

$R^7$ represents an alkyl group having 1 to 6 carbon atoms and $R^8$ represents a hydrogen atom or an alkyl group having 1 to 6 carbon atoms.

In a preferred combination of $R^5$ and $R^6$, one of $R^5$ and $R^6$ is a hydrogen atom and the other is an alkyl group having 1 to 3 carbon atoms.

In a more preferred combination, one of $R^5$ and $R^6$ is a hydrogen atom and the other is a methyl group or an ethyl group.

The pyrrolidine derivative having an aminoalkyl group on its 3-position can be produced, for example, in accordance with the method disclosed in JP-A-63-166876 or JP-A-3-72476.

In addition, the present inventors have found that a quinolone derivative having an aminocycloalkyl group-substituted saturated nitrogen-containing heterocyclic substituent shows strong antibacterial activity against Gram-positive bacteria particularly including MRSA.

That is, it is a case in which $R^2$ is a saturated nitrogen-containing heterocyclic substituent having a structure represented by the following formula (V).

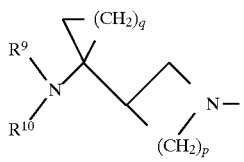

(V)

In this formula, $R^9$ is a hydrogen atom or an alkyl group having 1 to 6 carbon atoms. The alkyl group may be either straight or branched chain having 1 to 6 carbon atoms, and is preferably methyl, ethyl, n-propyl or isopropyl group.

$R^{10}$ is a hydrogen atom, an alkyl group having 1 to 6 carbon atoms, a hydroxyl group-containing alkyl group having 1 to 6 carbon atoms or a halogen atom-containing alkyl group having 1 to 6 carbon atoms.

The alkyl group may be either straight or branched chain having 1 to 6 carbon atoms, and is preferably methyl, ethyl, n-propyl or isopropyl group.

As the hydroxyl group-containing alkyl group having 1 to 6 carbon atoms, a 2-hydroxyethyl group or a 3-hydroxypropyl group is preferred.

As the halogen atom of the halogen atom-containing alkyl group having 1 to 6 carbon atoms, 1 to 3 fluorine atoms are particularly preferred. As the halogen atom-substituted alkyl group having 1 to 6 carbon atoms, a 2-fluoroethyl group, a 2,2-difluoroethyl group or a 2,2,2-trifluoroethyl group is particularly preferred.

Also, $R^9$ and $R^{10}$ may be combined to from a methylene chain having 2 to 6 carbon atoms and a ring structure including a nitrogen atom bonded to $R^9$ and $R^{10}$.

In a preferred combination of $R^9$ and $R^{10}$, one of $R^9$ and $R^{10}$ is a hydrogen atom and the other is an alkyl group having 1 to 6 carbon atoms, or $R^9$ is a hydrogen atom and $R^{10}$ is a hydroxyl group-containing alkyl group having 1 to 6 carbon atoms.

In a more preferred combination, one of $R^9$ and $R^{10}$ is a hydrogen atom and the other is a methyl group or an ethyl group, or $R^9$ is a hydrogen atom and $R^{10}$ is a 2-hydroxyethyl group.

Also, p is an integer of 1 to 3, preferably 2, and q is an integer of 1 to 3, preferably 1 or 2.

Binding with $R^2$ at the 7-position of the mother nucleus of the quinolone compound may be effected most preferably on the $R^2$ ring structure-forming nitrogen atom, but also on a carbon atom of $R^2$.

When stereoisomerism is present in $R^2$ and the quinolone mother nucleus compound is allowed to react directly with a mixture of stereoisomers of the compound represented by formula $R^2$—H, which is the source of the substituent $R^2$, the formed quinolone derivative becomes a mixture of diastereomers due to the 1,2-cis-2-halogenocyclopropyl group at the 1-position. Because of this, when stereoisomerism is present in $R^2$, it is desirable to allow only one of the isomers of the $R^2$—H compound to be reacted with the quionolone mother nucleus compound.

When $R^2$ is introduced into the 7-position of the quinolone and the $R^2$—H compound contains an amino group, the amino group may be subjected to the reaction as a compound converted into an ordinary protective group.

Examples of such protective groups include alkoxycarbonyl groups such as tertiary butoxycarbonyl, 2,2,2-trichloroethoxycarbonyl and the like, aralkyloxycarbonyl groups such as benzyloxycarbonyl, paramethoxybenzyloxycarbonyl, paranitrobenzyloxycarbonyl and the like, acyl groups such as acetyl, methoxyacetyl, trifluoroacetyl, chloroacetyl, pivaloyl, formyl, benzoyl and the like, alkyl or aralkyl groups such as tertiary butyl, benzyl, paranitrobenzyl, paramethoxybenzyl, triphenylmethyl and the like, alkylsulfonyl groups or halogenoalkylsulfonyl groups such as methanesulfonyl, trifluoromethanesulfonyl and the like, and arylsulfonyl groups such as benzenesulfonyl, toluenesulfonyl and the like.

Next, the halogenocyclopropyl group at the $N_1$-position is described.

Examples of the halogen atom to be substituted include a fluorine atom and a chlorine atom, of which a fluorine atom is particularly preferred.

With regard to the stereochemical environment in this moiety, it is particularly desirable that the halogen atom and the pyridonecarboxylic acid moiety take a cis configuration against the cyclopropane ring.

So-called enantiomeric isomers are formed only by this 1-position cis-2-halogenocyclopropyl moiety independent of the stereoisomerism of substituent groups at other positions, particularly $R^2$ at the 7-position. Strong antibacterial activity and high safety have been found in each of these isomers.

When the compound (I) of the present invention has a structure in which diastereomers exist and such a compound of the present invention is administered to human and animals, it is desirable to administer a compound comprising a pure diastereomer. The term "comprising a pure diastereomer" means not only a case in which the other diastereomer is entirely absent but also a case of chemically pure degree. In other words, the other diastereomer may be contained in such a degree that it does not exert influences upon physical constants and physiological activities.

Also, the term "stereochemically pure" means that when a compound has a plurality of isomeric species due to its asymmetric carbon atom, the compound is composed of only one of these species. The term "pure" in this case can also be considered in the same manner as described above.

The pyridonecarboxylic acid derivative of the present invention may be used as its free form, or as an acid addition salt or a salt of its carboxyl group. Examples of the acid addition salt include inorganic acid salts such as hydrochloride, sulfate, nitrate, hydrobromide, hydroiodide, phosphate and the like and organic acid salts such as acetate, methanesulfonate, benzenesulfonate, toluenesulfonate, citrate, maleate, fumarate, lactate and the like.

The salt of carboxyl group may be any one of inorganic and organic salts such as lithium salt, sodium salt, potassium salt and the like alkali metal salts, magnesium salt, calcium salt and the like alkaline earth metal salts, ammonium salt, triethylamine salt, N-methylglucamine salt, tris-(hydroxymethyl)aminomethane salt and the like.

In addition, these free form, acid addition salts and carboxyl group salts of the pyridonecarboxylic acid derivative may be present as hydrates.

On the other hand, quinolone derivatives, in which the carboxylic acid moiety is an ester, are useful as synthetic intermediates and prodrugs. For example, alkyl esters, benzyl esters, alkoxyalkyl esters, phenylalkyl esters and phenyl esters are useful as synthetic intermediates.

Examples of esters to be used as prodrugs are those which are easily hydrolyzed in the living body to form a free carboxylic acid, such as acetoxymethyl ester, pivaloiloxymethyl ester, ethoxycarbonyl ester, choline ester, dimethylaminoethyl ester, 5-indanyl ester, phthalidinyl ester and oxoalkyl esters such as 5-alkyl-2-oxo-1,3-dioxol-4-yl methyl ester, 3-acetoxy-2-oxobutyl ester and the like.

The compound of the present invention represented by the formula (I) can be produced by various methods. In a preferred example, it can be produced by allowing the compound of the formula $R^2$—H (wherein $R^2$ is as defined in the foregoing in relation to the formula (I), except that the amino group may be protected by a protective group Rx of the nitrogen atom), or an acid addition salt thereof to react with a compound (a quionolone mother nucleus compound) represented by formula (VI):

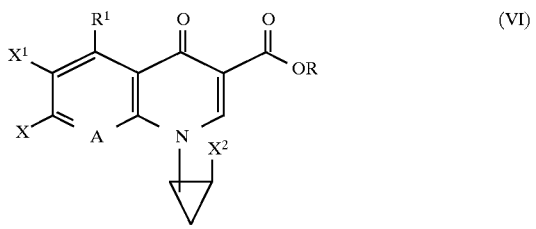

wherein X is a substituent which serves as a leaving group, for example, a fluorine atom, a chlorine atom, a bromine atom, an alkylsulfonyl group having 1 to 3 carbon atoms or arylsulfonyl groups such as a benzenesulfonyl group, a toluenesulfonyl group and the like, R is the same R defined in the formula (I) or a group represented by formula (VII):

wherein each of $R^{11}$ and $R^{12}$ is a fluorine atom or a lower alkylcarbonyloxy group, and $X^1$, $X^2$, $R^1$ and A are as defined in the formula (I).

The protective group Rx of the nitrogen atom is any group generally used in this field, and examples of such protective group include alkoxycarbonyl groups such as tertiary butoxycarbonyl, 2,2,2-trichloroethoxycarbonyl and the like, aralkyloxycarbonyl groups such as benzyloxycarbonyl, paramethoxybenzyloxycarbonyl, paranitrobenzyloxycarbonyl and the like, acyl groups such as acetyl, methoxyacetyl, trifluoroacetyl, chloroacetyl, pivaloyl, formyl, benzoyl and the like, alkyl or aralkyl groups such as tertiary butyl, benzyl, paranitrobenzyl, paramethoxybenzyl, triphenylmethyl arid the like, alkylsulfonyl or halogenoalkylsulfonyl groups such as methanesulfonyl, trifluoromethanesulfonyl and the like, and arylsulfonyl groups such as benzenesulfonyl, toluenesulfonyl and the like.

When R is a carboxylic acid derived from an aralkyl group comprising an alkyl group having 1 to 6 carbon atoms, an alkoxymethyl group having 2 to 7 carbon atoms or a group composed of an alkylene group having 1 to 6 carbon atoms and phenyl group, the compound of interest represented by the formula (I) can be obtained by carrying out conversion into corresponding carboxylic acid under acidic or basic conditions which are common in the hydrolysis of carboxylic acid esters and, if necessary in such case that the other substituents are protected, removing the protective group under corresponding suitable conditions.

When R in the compound of the formula (VI) is a group represented by the aforementioned formula (VII), its conversion into corresponding carboxylic acid can be made by firstly carrying out its substitution reaction with the compound $R^2$—H and then treating with an acidic or basic compound.

Substitution reaction of the compound of formula (VI) with the compound of $R^2$—H can be carried out with or without a solvent. When a solvent is used, it may be inert under the reaction conditions. Examples of suitable solvents include dimethyl sulfoxide, pyridine, acetonitrile, ethanol, chloroform, dimethylformamide, dimethylacetamide, N-methylpyrrolidone, tetrahydrofuran, water, 3-methoxybutanol and mixtures thereof.

The reaction can be carried out at a temperature of generally from room temperature to 200° C., preferably from 25° to 150° C. The reaction time is 30 minutes to 48 hours, and the reaction is completed generally in a time of from 30 minutes to 2 hours.

It is advantageous to carry out the reaction in the presence of an acid receptor which includes inorganic bases such as carbonates or hydrogencarbonates of alkali metals or alkaline earth metals and organic basic compounds such as triethylamine, pyridine and the like.

The following describes examples of the synthesis of amino-substituted condensed-bicyclic heterocyclic compounds. For example, 1-tert-butoxycarbonylamino-3-[(1S)-phenylethyl]-3-azabicyclo[3.1.0]hexane comprising a stereochemically pure isomer can be obtained by the following method.

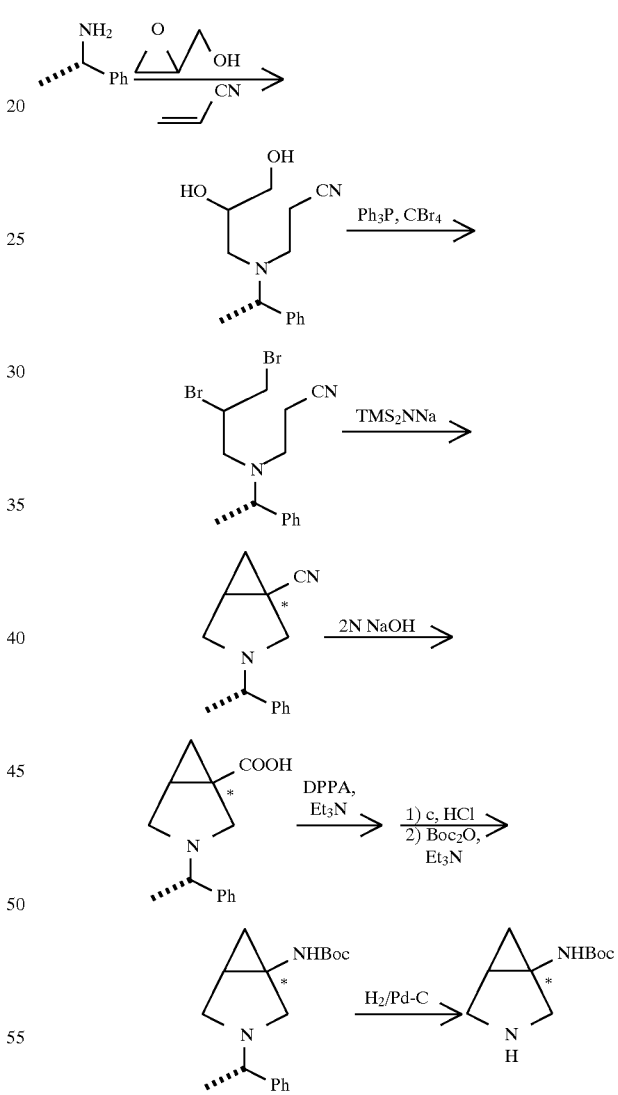

That is, (S)-(-)-phenylethylamine is allowed to react firstly with glycidol using ethanol as a solvent and then with acrylonitrile to give N-(2-cyanoethyl)-N-[(1S)-phenylethyl]-3-amino-1,2-propanediol. This compound is allowed to react with triphenylphosphine and carbon tetrabromide to give N-(2-cyanoethyl)-N-[(1S)-phenylethyl]-3-amino-1,2-dibromopropane. This compound is allowed to undergo reaction in the presence of a strong base to yield 1-cyano-3-[(1S)-phenylethyl]-3-azabicyclo[3.1.0]hexane. Since this compound has phenylethyl group at the 3-position and asymmetric carbon atom at the 1-position, a mixture of diastereomers is obtained. These isomers can be separated from each other by a silica gel column chromatography or a high performance liquid chromatography. Each of the thus obtained isomers is allowed to react with a base in an ordinary method to yield 3-[(1S)-phenylethyl]-3-azabicyclo [3.1.0]hexane-1-carboxylic acid. When this compound is subjected to Curtius reaction in the presence of tert-butanol, it can be converted at once into protected 3-[(1S)-phenylethyl]-3-azabicyclo[3.1.0]hexane-1-carboxylic acid. This reaction can be carried out easily when diphenylphosphorylazide is used, but synthesis of the intermediate azide is not limited thereto and any ordinary synthetic method can be employed. When the phenylethyl group is removed from this compound by catalytic hydrogenation in an ordinary method, 1-tert-butoxycarbonylamino-3-azabicyclo[3.1.0] hexane comprising a pure optical isomer is obtained.

1-Tert-butoxycarbonyl-3-azabicyclo[3.2.0]heptane which comprises stereochemically single isomer can be obtained, for example, by the following method.

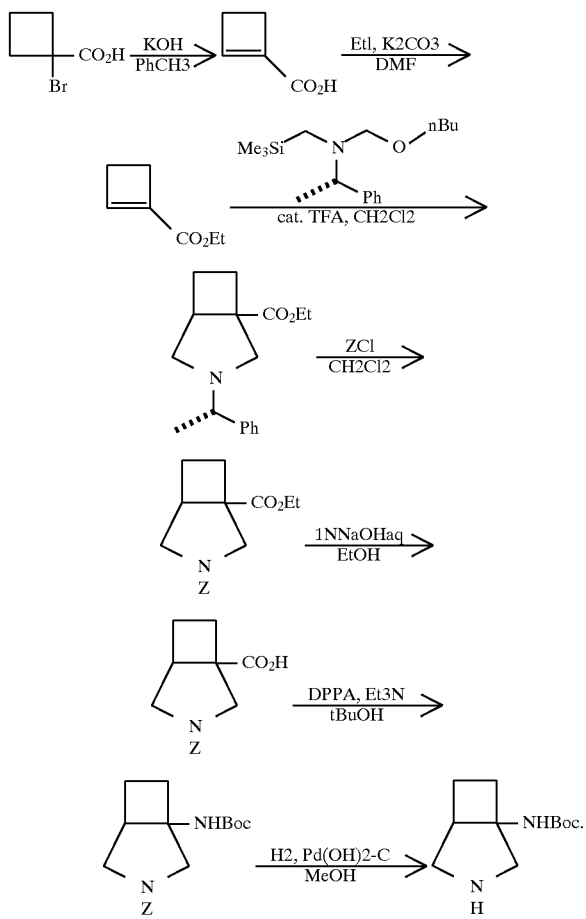

That is, 1-bromocyclobutenecarboxylic acid ethyl ester is allowed to react with a base to yield 1-cyclobutenecarboxylic acid. This compound is allowed to react with ethyl iodide using a base to yield 1-cyclobutenecarboxylic acid ethyl ester. Using an acid as a catalyst, this compound is allowed to react with n-butoxymethyltrimethylsilylmethyl[(S)-phenylethyl]amine to yield 3-[(S)-phenylethyl]-3-azabicyclo[3.2.0]heptane-1-carboxylic acid ethyl ester. Trifluoroacetic acid can be exemplified as the acid to be used in this reaction. Since this compound has phenylethyl group at the 3-position and asymmetric carbon atom at the 1-position, a mixture of diastereomers is obtained. These isomers can be separated from each other by a silica gel column chromatography or a high performance liquid chromatography. Each of the thus obtained isomers is allowed to react with benzyl chloroformate to give 3-benzyloxycarbonyl-3-azabicyclo[3.2.0] heptane-1-carboxylic acid ethyl ester. This compound is subjected to ester hydrolysis in an ordinary method to give 3-benzyloxycarbonyl-3-azabicyclo[3.2.0]heptane-1-carboxylic acid. When this compound is subjected to Curtius reaction in the presence of tert-butanol, it can be converted at once into protected 1-tert-butoxycarbonyl-3-benzyloxycarbonyl-3-azabicyclo[3.2.0]heptane. This reaction can be carried out easily when diphenylphosphorylazide is used, but synthesis of the intermediate azide is not limited thereto and any ordinary synthetic method can be employed. When the benzyloxycarbonyl group is removed from this compound by catalytic hydrogenation in an ordinary method, 1-tert-butoxycarbonyl-3-azabicyclo[3.2.0]heptane comprising a pure optical isomer is obtained.

The following describes examples of the synthesis of the aminocycloalkyl group-substituted saturated nitrogen-containing heterocyclic compound which is necessary for the introduction of the aminocycloalkyl group-substituted saturated nitrogen-containing heterocyclic group. In the following reaction formulae or description, Me means a methyl group, Et means an ethyl group, Ph means a phenyl group, Z means a benzyloxycarbonyl group, Boc means a tert-butoxycarbonyl group, TFA means a trifluoroacetic acid and Ts means a p-toluenesulfonyl group. In some cases, the arrow means a plurality of reaction steps.

1. Production of (3R)-3-(1-aminocyclopropyl) pyrrolidine:

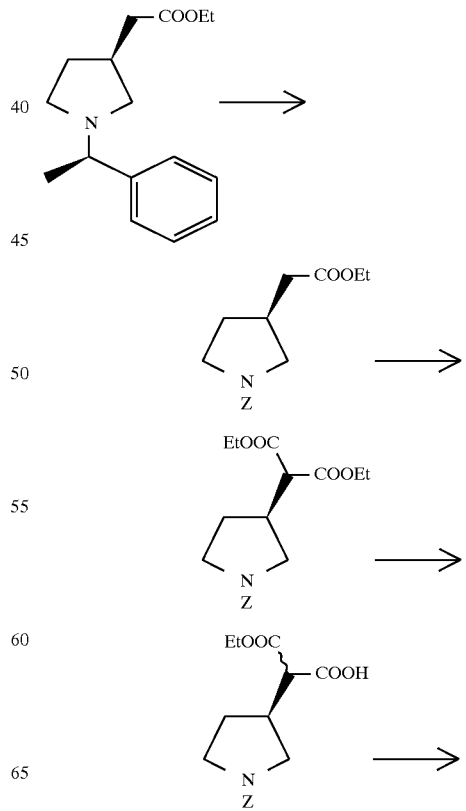

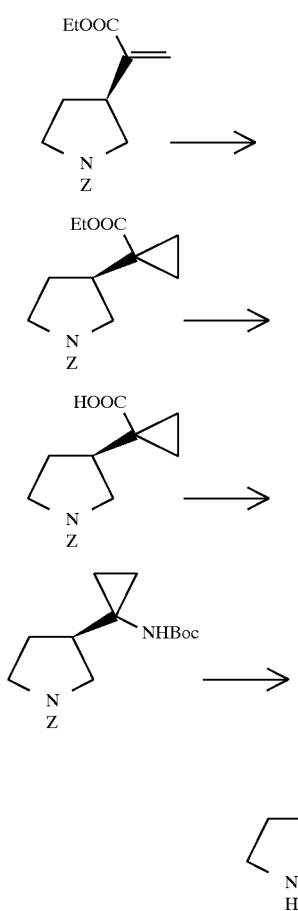

(3R)-Ethyl 1-[(R)-1-phenylethyl]pyrrolidine-3-acetate described in U.S. Pat. No. 621,101 is allowed to react with benzyl chlorocarbonate to give (3R)-ethyl 1-benzyloxycarbonylpyrrolidine-3-acetate.

Next, this compound is allowed to react firstly with a strong base and then with ethyl chlorocarbonate to give 1-benzyloxycarbonyl-3-(R)-pyrrolidinylmalonate. The compound is allowed to react a base to yield ethyl hydrogen 1-benzyloxycarbonyl-3-(R)-pyrrolidinylmalonate.

Next, this compound is allowed to react with Eschenmoser's salt to yield ethyl 2-(1-benzyloxycarbonyl-3-(R)-pyrrolidinyl)acrylate. This compound is allowed to react with diazomethane using palladium acetate as a catalyst to give ethyl 1-(1-benzyloxycarbonyl-3-(R)-pyrrolidinyl) cyclopropanecarboxylate.

Next, this compound is converted into 1-(1-benzyloxycarbonyl-3-(R)-pyrrolidinyl)cyclopropanecarboxylic acid by subjecting hydrolysis with a base in an ordinary method.

When this compound is subjected to Curtius reaction in the presence of tert-butanol, it can be converted at once into protected (3R)-1-benzyloxycarbonyl-3-(1-tert-butoxycarbonylaminocyclopropyl)pyrroridine. This reaction can be carried out easily when diphenylphosphorylazide is used, but synthesis of the intermediate azide is not limited thereto and any ordinary synthetic method can be employed.

When Z is removed from the thus obtained (3R)-1-benzyloxycarbonyl-3-(1-tert-butoxycarbonylaminocyclopropyl)pyrroridine by an ordinary catalytic hydrogenation or the like means,(3R)-3-(1-tert-butoxycarbonylaminocyclopropyl)pyrroridine is obtained.

Also, a (3S)-3-(1-aminocyclopropyl)pyrroridine derivative can be obtained when (3S)-ethyl[1-(S)-phenylethyl] pyrroridine-3-acetate is used in stead of (3R)-ethyl[1-(R)-phenylethyl]pyrroridine-3-acetate.

Also, (3R)-1-benzyloxycarbonyl-(1-ethoxycarbonylcyclopropyl)pyrroridine can be produced in the following manner. 2. Alternative method for the production of (3R)-3-(1-aminocyclopropyl)pyrroridine:

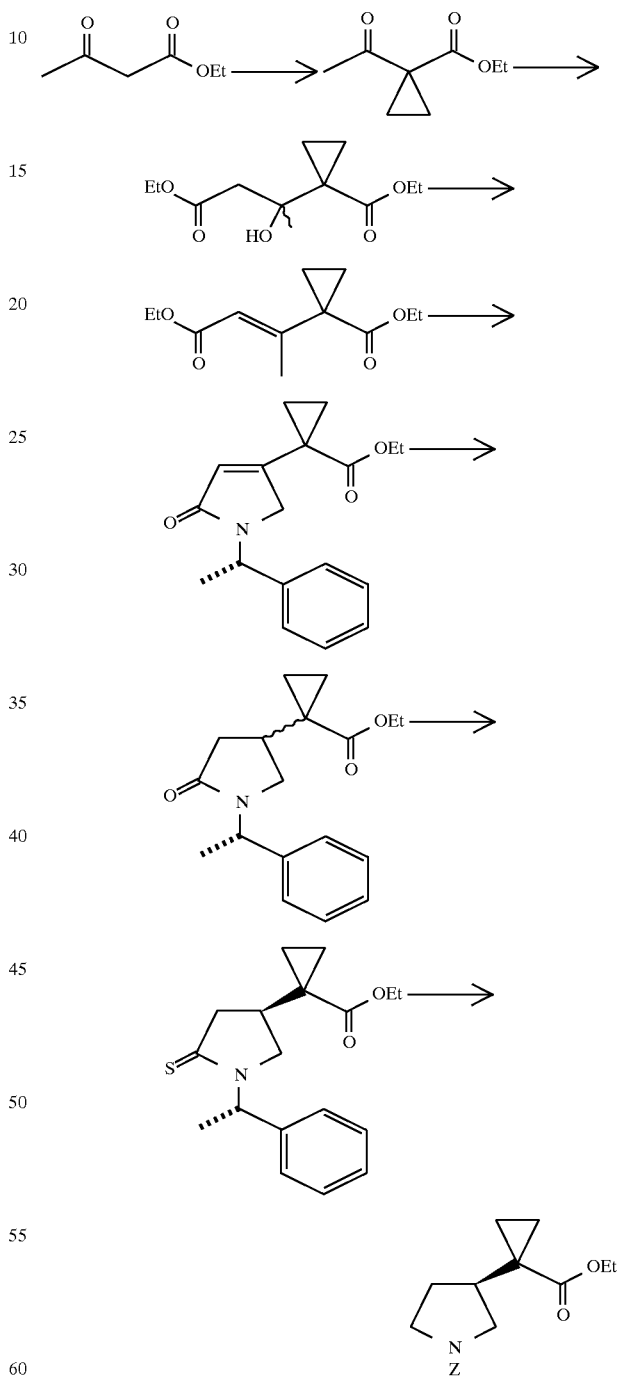

Ethyl acetoacetate is allowed to react with 1,2-dibromoethane to obtain ethyl 1-acetylcyclopropanecarboxylate. Next, ethyl 1-acetylcyclopropanecarboxylate is allowed to react with zinc powder and ethylbromoacetate to give ethyl 1-ethoxycarbonyl-β-hydroxy-β-methyl-cyclopropanoate.

Next, this compound is allowed to react with thionyl chloride using pyridine as a solvent to yield 1-ethoxycarbonyl-β-chloro-β-methylcyclopropanepropanoate and then with a base to obtain (E)-ethyl 3-(1-ethoxycarbonylcyclopropyl)-2-butenoate. Examples of the organic bases to be used include pyridine, 2,6-lutidine and the like aromatic heterocyclic compounds, as well as 1,8-diazabicyclo[5.4.0]undec-7-ene, 1,5-diazabicyclo[4.3.0]non-5-ene and the like organic bases.

Thereafter, (3R)-3-(1-aminocyclopropyl)pyrrolidine is obtained by the aforementioned reaction.

(3R)-3-(1-Alkylaminocyclopropyl)pyrrolidine or (3R)-1-[1-(N-tert-butoxycarbonyl-N-(2-hydroxyethyl)amino)cyclopropyl]pyrrolidine can be synthesized in the following manner.

3. Production of (3R)-3-(1-substituted aminocyclopropyl)pyrrolidine:

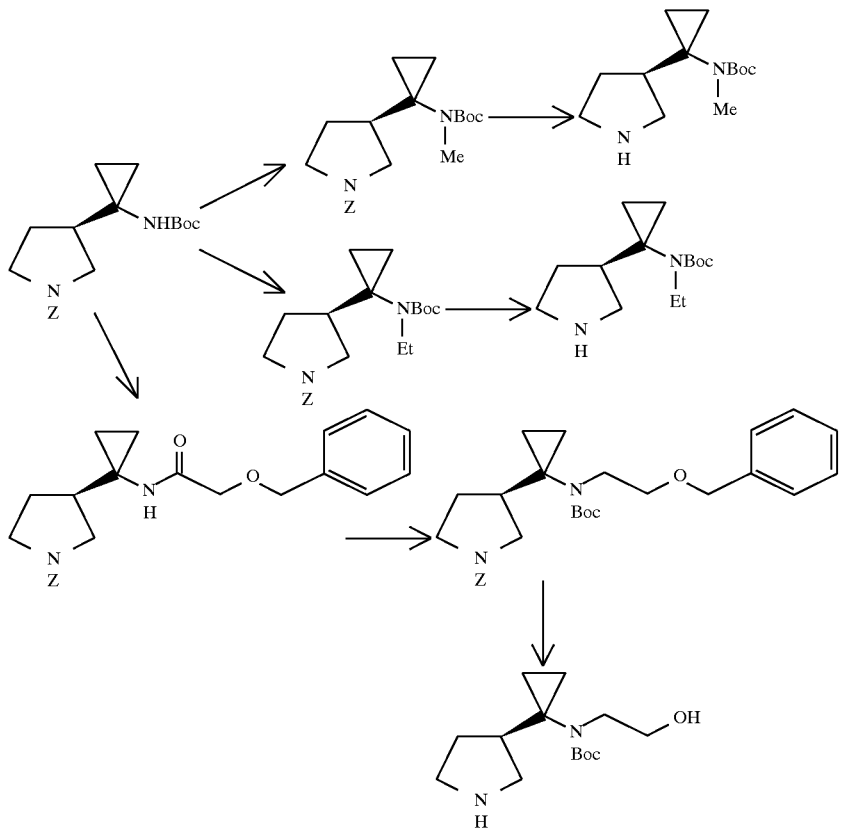

(E)-Ethyl 3-(1-ethoxycarbonylcyclopropyl)-2-butenoate thus obtained is allowed to react with N-bromosuccinimide to give (E)-ethyl 4-bromo-3-(1-ethoxycarbonylcyclopropyl)-2-butenoate which is then allowed to react with (S)-phenylethylamine to yield 4-(1-ethoxycarbonylcyclopropyl)-1-[(S)-1-phenylethyl]-3-pyrrolin-2-one. This compound is subjected to an ordinary catalytic hydrogenation to obtain 4-(1-ethoxycarbonylcyclopropyl)-1-[(S)-1-phenylethyl]-2-pyrrolidone. This compound is a diastereomer mixture due to the presence of (S)-phenylethyl group on the 1-position. Separation of this mixture can be effected by a fractional recrystallization or a silica gel column chromatography.

The thus separated (4R)-4-(1-ethoxycarbonylcyclopropyl)-1-[(S)-1-phenylethyl]-2-pyrrolidone is allowed to react with Lawesson reagent to give (4S)-4-(1-ethoxycarbonylcyclopropyl)-1-[(S)-1-phenylethyl]-2-pyrrolidinethione. This reaction can also be effected using phosphorus pentasulfide.

The thus obtained (4S)-4-(1-ethoxycarbonylcyclopropyl)-1-[(S)-1-phenylethyl]-2-pyrrolidinethione is allowed to react with Raney nickel and then with benzyl chloroformate to yield (3R)-1-benzyloxycarbonyl-(1-ethoxycarbonylcyclopropyl)pyrrolidine.

In order to obtain (3R)-3-(1-methylaminocyclopropyl)pyrrolidine, (3R)-1-benzyloxycarbonyl-3-(1-tert-butoxycarbonylaminocyclopropyl)pyrrolidine is firstly allowed to react with methyl iodide and silver oxide in N,N-dimethylformamide to obtain(3R)-1-benzyloxycarbonyl-3-[1-(N-tert-butoxycarbonyl-N-methyl)aminocyclopropyl]pyrrolidine.

(3R)-1-Benzyloxycarbonyl-3-[1-(N-tert-butoxycarbonyl-N-ethyl)aminocyclopropyl]pyrrolidine can be obtained when ethyl iodide is used instead of methyl iodide.

Thereafter, Z is removed from this compound by an ordinary catalytic hydrogenation to give (3R)-3-(1-alkylaminocyclopropyl)pyrrolidine.

In order to obtain (3R)-1-[1-(N-tert-butoxycarbonyl-N-(2-hydroxyethyl)amino)cyclopropyl]pyrrolidine, Boc is firstly removed from (3R)-1-benzyloxycarbonyl-3-(1-tert-butoxycarbonylaminocyclopropyl)pyrrolidine by its reaction under an acidic condition using trifluoroacetic acid, hydrochloric acid or the like, and the product is then allowed to react with benzyloxyacetyl chloride in the presence of triethylamine or the like acid-removing agent to yield (3R)-3-[1-(benzyloxyacetyl)aminocyclopropyl]-1-benzyloxycarbonylpyrrolidine.

By reducing this compound with borane-tetrahydrofuran complex and then adding Boc thereto, (3R)-1- benzyloxycarbonyl-3-[1-(N-2-benzyloxyethyl-N-tert-butoxycarbonyl)aminocyclopropyl]pyrrolidine is obtained.

Thereafter, the benzyl group and Z are removed from this compound by an ordinary catalytic hydrogenation to give (3R)-1-[1-(N-tert-butoxycarbonyl-N-(2-hydroxyethyl)amino)cyclopropyl]pyrrolidine.

3-(1-Tert-butoxycarbonylaminocyclobutyl)pyrrolidine can be produced, for example, by the following method.

4. Production of 3-(1-tert-butoxycarbonylaminocyclobutyl)pyrrolidine:

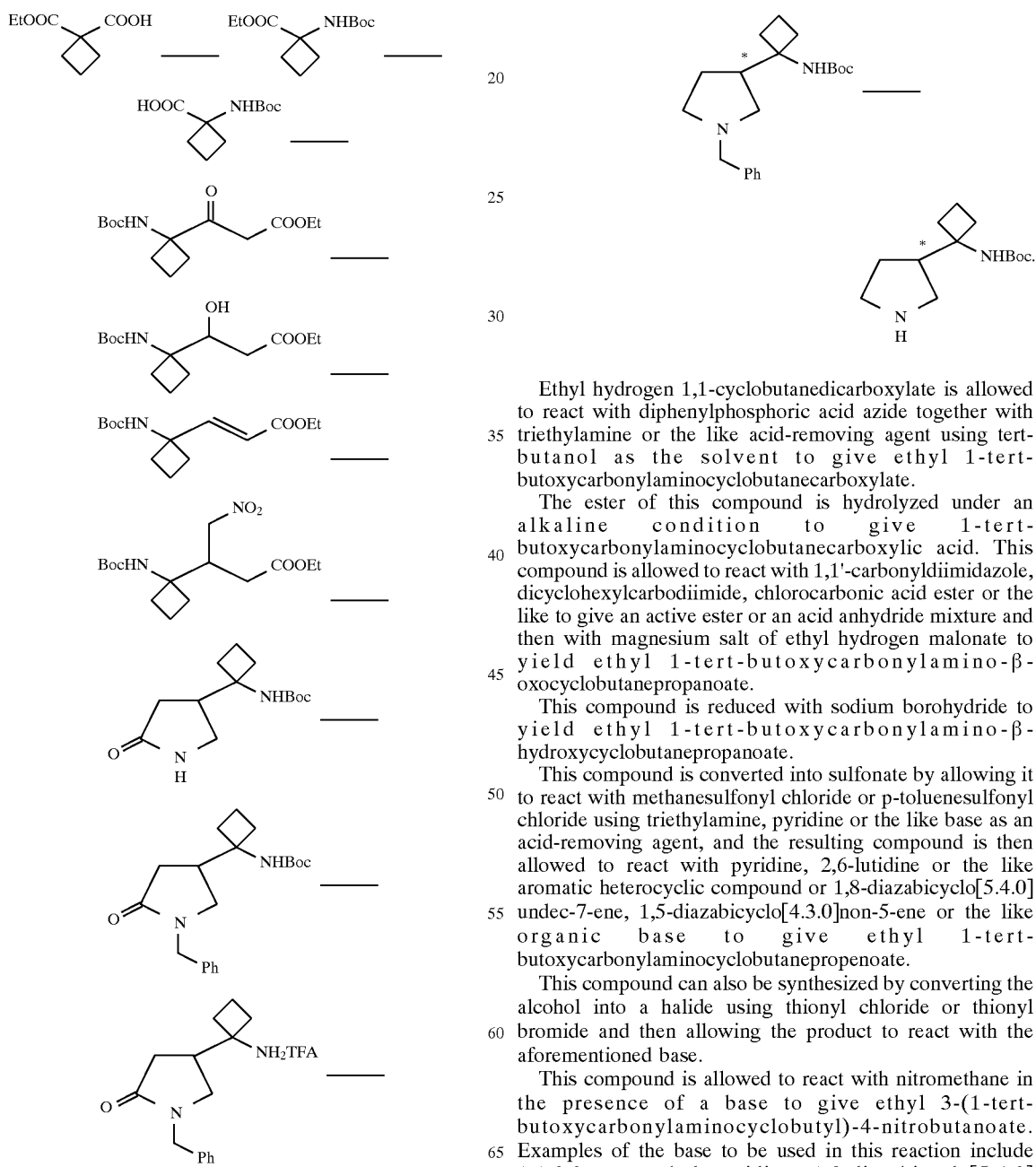

Ethyl hydrogen 1,1-cyclobutanedicarboxylate is allowed to react with diphenylphosphoric acid azide together with triethylamine or the like acid-removing agent using tert-butanol as the solvent to give ethyl 1-tert-butoxycarbonylaminocyclobutanecarboxylate.

The ester of this compound is hydrolyzed under an alkaline condition to give 1-tert-butoxycarbonylaminocyclobutanecarboxylic acid. This compound is allowed to react with 1,1'-carbonyldiimidazole, dicyclohexylcarbodiimide, chlorocarbonic acid ester or the like to give an active ester or an acid anhydride mixture and then with magnesium salt of ethyl hydrogen malonate to yield ethyl 1-tert-butoxycarbonylamino-β-oxocyclobutanepropanoate.

This compound is reduced with sodium borohydride to yield ethyl 1-tert-butoxycarbonylamino-β-hydroxycyclobutanepropanoate.

This compound is converted into sulfonate by allowing it to react with methanesulfonyl chloride or p-toluenesulfonyl chloride using triethylamine, pyridine or the like base as an acid-removing agent, and the resulting compound is then allowed to react with pyridine, 2,6-lutidine or the like aromatic heterocyclic compound or 1,8-diazabicyclo[5.4.0]undec-7-ene, 1,5-diazabicyclo[4.3.0]non-5-ene or the like organic base to give ethyl 1-tert-butoxycarbonylaminocyclobutanepropenoate.

This compound can also be synthesized by converting the alcohol into a halide using thionyl chloride or thionyl bromide and then allowing the product to react with the aforementioned base.

This compound is allowed to react with nitromethane in the presence of a base to give ethyl 3-(1-tert-butoxycarbonylaminocyclobutyl)-4-nitrobutanoate. Examples of the base to be used in this reaction include 1,1,3,3-tetramethylguanidine, 1,8-diazabicyclo[5.4.0]undec-7-ene and the like organic bases.

This reaction can be carried out using a solvent or nitromethane as the solvent. Examples of the solvent to be used in this reaction are those which are inert under the reaction conditions, such as benzene, toluene and the like aromatic compounds, chloroform, dichloromethane and the like chlorine-based compounds or diethyl ether, tetrahydrofuran and the like ether compounds.

When the thus obtained ethyl 3-(1-tert-butoxycarbonylaminocyclobutyl)-4-nitrobutanoate is subjected to usually used catalytic hydrogenation, 4-(1-tert-butoxycarbonylaminocyclobutyl)-2-pyrrolidone cyclized at once after reduction of nitro group into amino group is obtained.

When uncyclized 4-amino-3-(1-tert-butoxycarbonylaminocyclobutyl)butanoate is present, it can be converted into 4-(1-tert-butoxycarbonylaminocyclobutyl)-2-pyrrolidone by heating it with or without using benzene, toluene or the like solvent.

In this cyclization reaction, sodium ethylate, potassium butylate or the like base can be used.

Next, 4-(1-tert-butoxycarbonylaminocyclobutyl)-2-pyrrolidone is allowed to react with benzyl bromide or benzyl chloride using a base to yield 1-benzyl-4-(1-tert-butoxycarbonylaminocyclobutyl)-2-pyrrolidone.

This compound is treated under an acidic condition to remove Boc, thereby obtaining 4-(1-aminocyclobutyl)-1-benzyl-2-pyrrolidone. This reaction can be carried out using any usually used method for the removal of Boc.

4-(1-Aminocyclobutyl)-1-benzyl-2-pyrrolidone trifluoroacetate can be used in the following reaction as an acid addition product such as trifluoroacetate or as its free form which can be obtained by neutralizing it in the usual way after the reaction.

4-(1-Aminocyclobutyl)-1-benzyl-2-pyrrolidone trifluoroacetate is allowed to react with D-(R)-N-p-toluenesulfonylproline acid chloride in the presence of pyridine or the like acid-removing agent to give 1-benzyl-4-[1-[N'-p-toluenesulfonyl-2-(R)-pyrrolidinecarbonyl]aminocyclobutyl]-2-pyrrolidone which is then separated into 2 stereoisomers.

Separation of the isomers can be effected by a silica gel column chromatography or a high performance liquid chromatography.

Each of the thus separated isomers is hydrolyzed with an acid to give optically active 1-benzyl-4-(1-aminocyclobutyl)-2-pyrrolidone. Each of the optical isomers is allowed to react with lithium aluminum hydride to yield 1-benzyl-3-(1-aminocyclobutyl)pyrrolidine which is subsequently allowed to react with di-tert-butyldicarbonate to give 1-benzyl-3-(1-tertbutoxycarbonylaminocyclobutyl)pyrrolidine.

When this compound is subjected to catalytic hydrogenation in an ordinary method, optically active 3-(1-tertbutoxycarbonylaminocyclobutyl)pyrrolidine is obtained.

3-(1-Tert-butoxycarbonylaminocyclopropyl)azetidine can be produced, for example, by the following method.

5. Production of 3-(1-tert-butoxycarbonylaminocyclopropyl)azetidine:

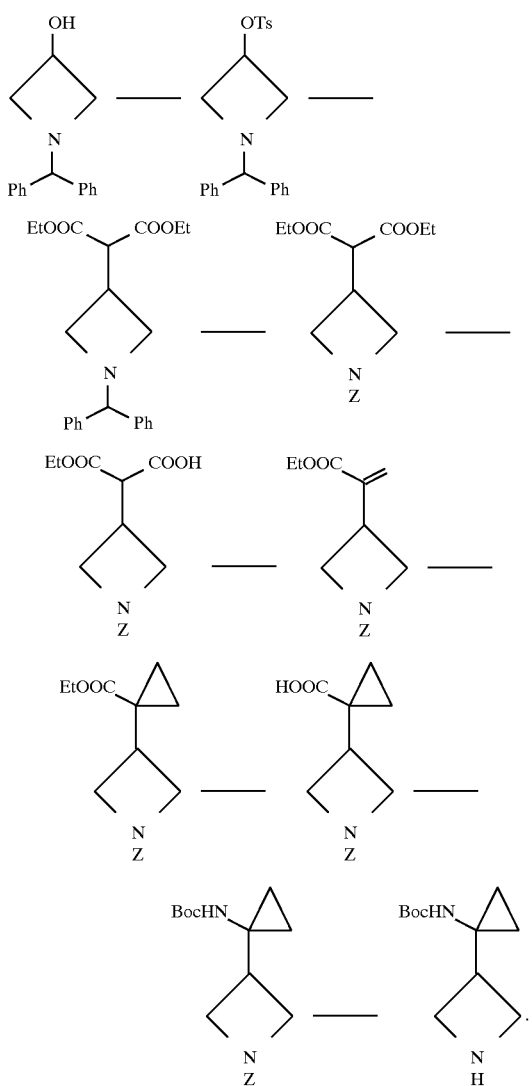

1-Benzhydryl-3-hydroxyazetidine is allowed to react with p-toluenesulfonyl chloride using an acid-removing agent to give 1-benzhydryl-3-(p-toluenesulfonyloxy)azetidine. This compound is allowed to react with diethyl malonate in the presence of a base to give diethyl (1-benzhydryl-3-azetidinyl)malonate.

This compound is allowed to react with benzyl chloroformate to yield diethyl (1-benzyloxycarbonyl-3-azetidinyl)malonate which is then subjected to partial ester hydrolysis to obtain ethyl hydrogen (1-benzyloxycarbonyl-3-azetidinyl)malonate.

When this compound is allowed to react with Eschenmoser's salt, ethyl 2-(1-benzyloxycarbonyl-3-azetidinyl)acrylate is obtained. Using a base, this compound is allowed to react with trimethylsulfoxonium iodide to give ethyl 1-(1-benzyloxycarbonyl-3-azetidinyl)cyclopropanecarboxylate.

This compound is hydrolyzed to yield 1-(1-benzyloxycarbonyl-3-azetidinyl)cyclopropanecarboxylic acid which is then allowed to react with diphenylphospholic acid azide in the presence of a base using t-butanol as the solvent to yield 1-benzyloxycarbonyl-3-(1-tert-butoxycarbonylaminocyclopropyl)azetidine. When this compound is subjected to catalytic hydrogenation in an ordinary method, 3-(1-tert-butoxycarbonylaminocyclopropyl)azetidine is obtained.

A quinolone compound having a substituent group represented by the formula (IV) or (V) can be produced in the same manner as the case of the production of quinolone compound having the substituent group of formula (II).

On the other hand, synthesis of a compound of formula (VIII) comprising a single isomer from an optically active cis-2-fluorocyclopropylamine derivative can be carried out, for example, in accordance with the method disclosed in JP-A-2-231475.

Ethyl 2,3,4,5,6-pentafluorobenzoylacetate is allowed to react with N,N-dimethylformamide dimethylacetal and then with (1R,2S)-2-fluorocyclopropylamine p-toluenesulfonate in the presence of triethylamine or the like acid-removing agent, thereby ethyl 5,6,7,8-tetrafluoro-1-[(1R,2S)-2-fluorocyclopropyl]-1,4-dihydro-4-oxoquinoline-3-carboxylate is obtained.

This compound is allowed to react with benzyl alcohol in the presence of a base to give ethyl 5-benzyloxy-6,7,8-

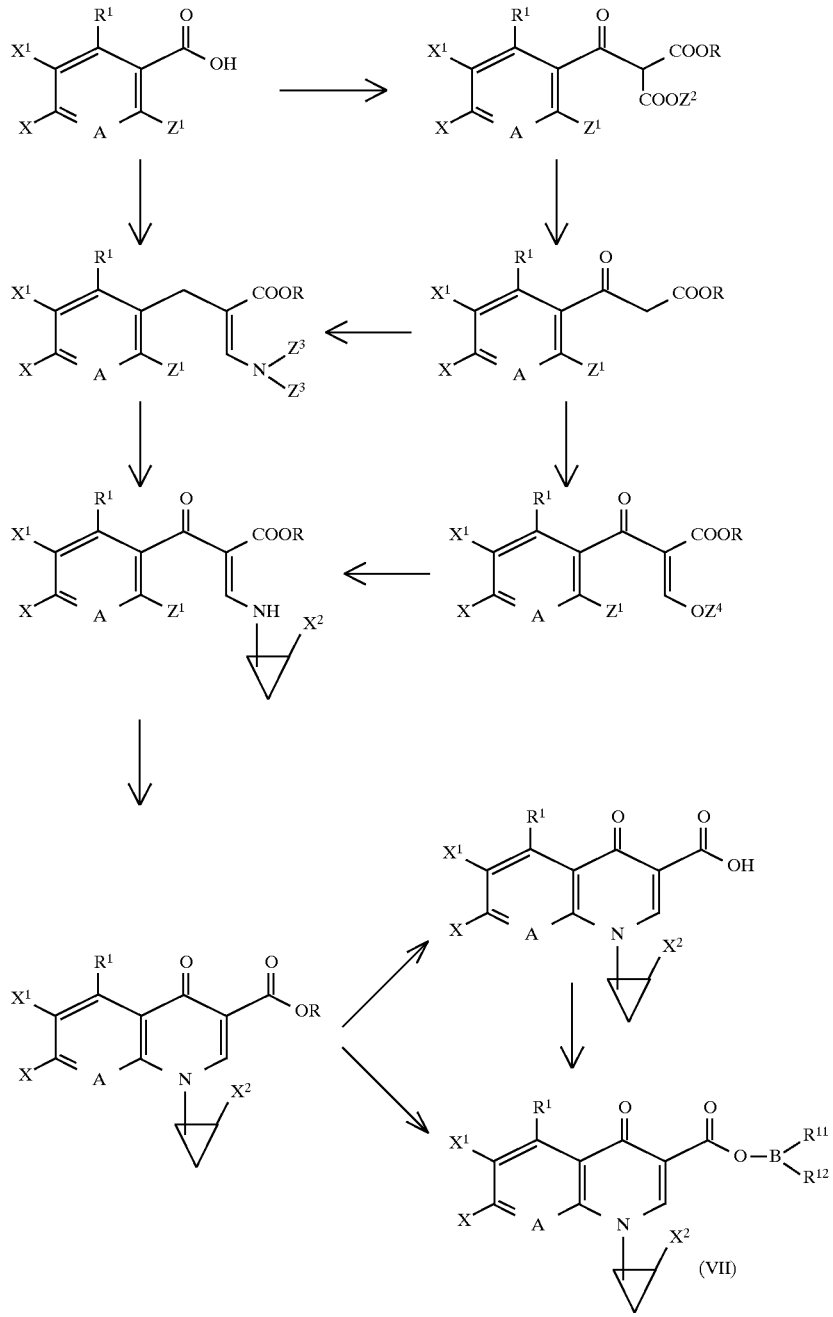

6,7,8-Trifluoro-1-[(1R,2S)-2-fluorocyclopropyl]-1,4-dihydro-5-hydroxy-4-oxoquinoline-3-carboxylate as a member of the compound represented by formula (VIII) can be synthesized in the following manner.

trifluoro-1-[(1R,2S)-2-fluorocyclopropyl]-1,4-dihydro-4-oxoquinoline-3-carboxylate. This reaction can be carried out in accordance with any known method in this field. Examples of the base useful in this reaction include sodium hydride, potassium carbonate, sodium hydroxide and potassium hydroxide.

When this compound is treated under an acidic condition, 6,7,8-trifluoro-1-[(1R,2S)-2-fluorocyclopropyl]-1,4-dihydro-5-hydroxy-4-oxoquinoline-3-carboxylate is obtained.

A member of the compound of formula (VIII) in which $R^1$ is amino group and $X^3$ is a lower alkyl group can be obtained in the same manner as described above, using 2,4,5-trifluoro-6-nitrobenzoic acid having a lower alkyl group on its 3-position, as a starting material which is obtained by subjecting 2,4,5-trifluorobenzoic acid having a lower alkyl group on its 3-position to nitration in the usual way.

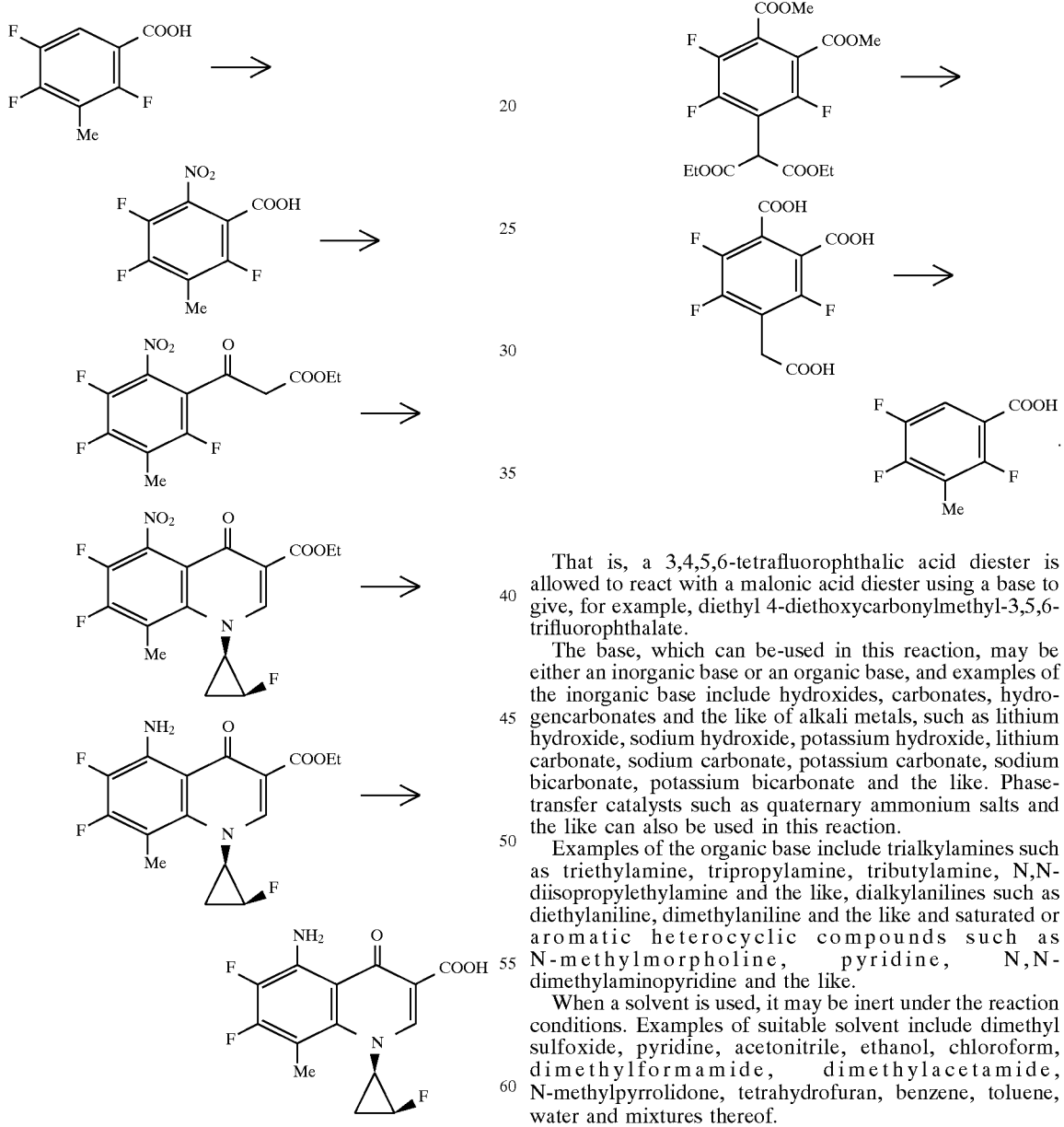

Though 3-methyl-2,4,5-trifluorobenzoic acid can be produced in accordance with the method disclosed in JP-A-61-205240 or JP-A-3-95176, it can be synthesized more easily by the following method.

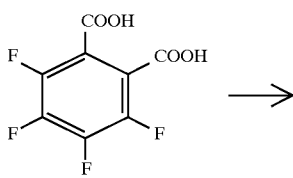

That is, a 3,4,5,6-tetrafluorophthalic acid diester is allowed to react with a malonic acid diester using a base to give, for example, diethyl 4-diethoxycarbonylmethyl-3,5,6-trifluorophthalate.

The base, which can be-used in this reaction, may be either an inorganic base or an organic base, and examples of the inorganic base include hydroxides, carbonates, hydrogencarbonates and the like of alkali metals, such as lithium hydroxide, sodium hydroxide, potassium hydroxide, lithium carbonate, sodium carbonate, potassium carbonate, sodium bicarbonate, potassium bicarbonate and the like. Phase-transfer catalysts such as quaternary ammonium salts and the like can also be used in this reaction.

Examples of the organic base include trialkylamines such as triethylamine, tripropylamine, tributylamine, N,N-diisopropylethylamine and the like, dialkylanilines such as diethylaniline, dimethylaniline and the like and saturated or aromatic heterocyclic compounds such as N-methylmorpholine, pyridine, N,N-dimethylaminopyridine and the like.

When a solvent is used, it may be inert under the reaction conditions. Examples of suitable solvent include dimethyl sulfoxide, pyridine, acetonitrile, ethanol, chloroform, dimethylformamide, dimethylacetamide, N-methylpyrrolidone, tetrahydrofuran, benzene, toluene, water and mixtures thereof.

The reaction can be carried out at a temperature of generally from 0° to 150° C., preferably from 25° to 100° C.

Next, diethyl 4-diethoxycarbonylmethyl-3,5,6-trifluorophthalate is hydrolyzed under-an acidic or basic condition to yield 4-carboxymethyl-3,5,6-trifluorophthalic acid.

Examples of the acid to be used in this reaction include concentrated sulfuric acid and concentrated hydrochloric acid. Examples of the base include inorganic bases such as hydroxides, carbonates, hydrogencarbonates and the like of alkali metals, including lithium hydroxide, sodium hydroxide, potassium hydroxide, lithium carbonate, sodium carbonate, potassium carbonate, sodium bicarbonate, potassium bicarbonate and the like.

The thus obtained 4-carboxymethyl-3,5,6-trifluorophthalic acid is heated in dimethyl sulfoxide in the presence of a base to give 3-methyl-2,4,5-trifluorobenzoic acid.

Examples of the organic base to be used in this reaction include trialkylamines such as triethylamine, tripropylamine, tributylamine, N,N-diisopropylethylamine and the like, dialkylanilines such as diethylaniline, dimethylaniline and the like and saturated or aromatic heterocyclic compounds such as N-methylmorpholine, pyridine, N,N-dimethylaminopyridine and the like.

The reaction can be carried out at a temperature of generally from 100° to 200° C., preferably from 100° to 150° C. The reaction may be carried out for 1 to 96 hours, but it will be completed generally within 5 to 48 hours.

This production process can be carried out in the same manner when 3,4,5,6-tetrafluorophthalonitrile is used instead of 3,4,5,6-tetrafluorophthalic acid diester as the starting material. Also, malononitrile may be used instead of malonic acid diester, and an alkylmalonic acid diester and an alkylmalononitrile are useful for the production of a 3-alkyl-2,4,5-trifluoro-6-nitrobenzoic acid which has an alkyl group other than methyl group.

Since the compound of the present invention shows strong antibacterial actions, it can be used as medicines for human, animals and fishes or preservatives of agricultural chemicals and food.

When the compound of the present invention is used as a medicine in human, its dose may be in the range of from 50 mg to 1 g, preferably from 100 mg to 300 mg, per adult per day.

When used in animals, its dose varies depending on the purpose of administration (treatment or prevention), kind and size of each animal to be treated, kind of infected pathogenic bacterium and degree of the infection, but is generally in the range of from 1 to 200 mg, preferably from 5 to 100 mg, per day per 1 kg of animal body weight.

The daily dose may be used once a day or divided into 2 to 4 doses per day. If necessary, the daily dose may exceed the range recited above.

Since the compound of the present invention is active upon a broad range of microorganisms which cause various types of infectious diseases, it can heal, prevent or alleviate diseases caused by these pathogenic microorganisms.

Examples of bacteria and bacterioidal microorganisms sensitive to the compound of the present invention include the genus Staphylococcus, *Streptococcus pyogenes, hemolytic streptococcus, enterococcus, pneumococcus*, the genus Peptostreptococcus, gonococcus, *Escherichia coli*, the genus Citrobacter, the genus Shigella, Friedlander's bacillus, the genus Enterobacter, the genus Serratia, the genus Proteus, *Psuedomonas aeruginosa, Haemophilus influenzae,* the genus Acinetobacter, the genus Campylobacter, *Chlamydia trachomatis* and the like.

Examples of diseases caused by these pathogenic microorganisms include folliculitis, furuncle, carbuncle, erysipelas, phlegmon, lymphangitis, felon, subcutaneous abscess, hidradenitis, acne, infectious atheroma, perirectal abscess, mastitis, superficial secondary infections such as of injury, burn injury, operative wound and the like, pharyngolaryngitis, acute bronchitis, tonsillitis, chronic bronchitis, bronchiectasis, diffuse panbronchiolitis, secondary infection of chronic respiratory disease, pneumonia, pyelonephritis, cystitis, prostatitis, epididymitis, gonococcal urethritis, non-gonococcal urethritis, cholecystitis, cholangitis, bacillary dysentery, enteritis, uterine adnexitis, intrauterine infection, bartholinitis, blepharitis, hordeolum, dacryocystitis, tarsadenitis, corneal ulcer, otitis media, sinusitis, periodontium inflammation, pericrown inflammation, jaw inflammation, peritonitis, endocarditis, sepsis, meningitis, dermal infection and the like.

The compound of the present invention is also effective against various microorganisms which cause infectious diseases in animals, such as those which belong to the genera Escherichia, Salmonella, Pasteurelle, Haemophilus, Bordetella, Staphylococcus, Mycoplasma and the like. Illustrative examples of such diseases include coli bacillosis, pullorum disease, chicken paratyphoid fever, fowl cholera, infectious coryza, staphylococcal infection, mycoplasma infection and the like in the case of birds, coli bacillosis, salmonellosis, pasteurellosis, haemophilus infection, atrophic rhinitis, exudative epidermis, mycoplasma infection and the like in the case of swine, coli bacillosis, salmonellosis, hemorrhagic sepsis, mycoplasma infection, bovine pleuropneumonia, bovine mastitis and the like in the case of cattle, coli sepsis, salmonella infection, hemorrhagic sepsis, uterine empyema, cystitis and the like in the case of dogs, and exudative pleurisy, cystitis, chronic rhinitis, haemophilus infection, kitten diarrhea, mycoplasma infection and the like in the case of cats.

The antibacterial agent, which comprises the compound of the present invention, can be prepared making use of various commonly used pharmaceutical drug preparation methods by selecting appropriate dosage form corresponding to each administration method. Examples of the dosage form of the antibacterial agent which contains the compound of the present invention as the active component include oral preparations such as tablets, powders, capsules, solutions, syrups, elixirs, oily or aqueous suspensions and the like.

When used as injections, the preparation may contain a stabilizing agent, an antiseptic agent and a solubilizing agent. As occasion demands, a solution which may contain such auxiliary substances may be packed in containers and made into a solid preparation by freeze-drying or the like means to be dissolved again before its use. Also, a container may be packed with a single dose or multiple doses.

The antibacterial agent of the present invention may also be made into preparations for external use such as solutions, suspensions, emulsions, ointments, gels, creams, lotions, sprays and the like.

Solid preparations contain pharmaceutically acceptable additives together with the active compound and can be produced by mixing these additives optionally selected, for example, from fillers, extenders, binders, disintegrating agents, solubilizing agents, moistening agents, lubricants and the like.

Liquid preparations include solutions, suspensions, emulsions and the like which may contain suspending agents, emulsifying agents and the like as additives.

When the compound of the present invention is applied to animals, it may be effected, for example, by a method in which the compound is orally administered directly or after adding it to feed, by another method in which the compound is made into a solution and then orally administered directly or after adding it to drinking water or feed or by injection.

When the compound of the present invention is administered to animals, it can be made optionally into powders, fine subtilaes, dissolvable powders, syrups or injections in accordance with usually used techniques in this field.

Examples of the formulation of pharmaceutical preparations are shown below.

PREPARATION EXAMPLE 1 (CAPSULES)

| | |
|---|---|
| Compound of Inventive Example 2 | 100.0 mg |
| Corn starch | 23.0 mg |
| CMC calcium | 22.5 mg |
| Hydroxymethylcellulose | 3.0 mg |
| Magnesium stearate | 1.5 mg |
| Total | 150.0 mg |

PREPARATION EXAMPLE 2 (SOLUTION)

| | |
|---|---|
| Compound of Inventive Example 2 | 1–10 g |
| Acetic acid or sodium hydroxide | 0.5–2 g |
| Ethyl paraoxybenzoate | 0.1 g |
| Purified water | 88.9–98.4 g |
| Total | 100 g |

PREPARATION EXAMPLE 3 (POWDER FOR FEED MIXING USE)

| | |
|---|---|
| Compound of Inventive Example 2 | 1–10 g |
| Corn starch | 98.5–89.5 g |
| Soft silicic anhydride | 0.5 g |
| Total | 100 g |

BEST MODE FOR CARRYING OUT INVENTION

The following Inventive and Reference Examples are provided to further illustrate the present invention, but not by way of limitation. The antibacterial activity of optically active compounds of interest was tested in accordance with the standard method designated by Japan Society of Chemotherapy. The results are shown in Table 1 as MIC ($\mu$g/ml).

Reference Example A-1

N-(2-Cyanoethyl)-N-[(1S)-phenylethyl]-3-amino-1,2-propanediol

Glycidol (37 g, 0.5 mol) was added to an ethanol (500 ml) solution of (S)-(–)-phenylethylamine (75 ml, 0.58 mmol) under ice cooling, and the mixture was stirred for 20 minutes at room temperature and then heated under reflux for 62 hours. After adding acrylonitrile (40 ml) thereto, the reaction mixture was heated under reflux for 45 hours and then concentrated. Thereafter, the resulting residue was applied to a silica gel column chromatography and eluted with 5% methanol-chloroform to yield 121 g (84%) of the title compound.

$^1$H-NMR (CDCl$_3$) δ: 1.41–1.48 (3H, m), 2.39–2.50 (2H, m), 2.60–3.25 (4H, m), 3.41–3.46 (1H, m), 3.68–3.78 (2H, m), 3.93–4.02 (1H, m), 7.27–7.40 (5H, m).

Reference Example A-2

N-(2-Cyanoethyl-N-[(1S)-phenylethyl]-3-amino-1,2-dibromopropane

To a solution of N-(2-cyanoethyl)-N-[(1S)-phenylethyl]-3-amino-1,2-propanediol (24.8 g, 0.1 mol) in benzene (400 ml) were added triphenylphosphine (57.71 g, 0.22 mol) and carbon tetrabromide (73 g, 0.22 mol). With stirring, the resulting mixture was heated to 90° C. After separating the supernatant fluid and evaporating the solvent, the resulting residue was applied to a silica gel column chromatography and eluted with n-hexane-ethyl acetate (4:1) to yield 38 g (100%) of the title compound.

$^1$H-NMR (CDCl$_3$) δ: 1.43–1.46 (3H, m), 2.35–2.44 (2H, m), 2.82∝2.96 (3H, m), 3.14–3.27 (1H, m), 3.67–4.15 (4H, m), 7.27–7.40 (5H, m).

Reference Example A-3

1-Cyano-3-[(1S)-phenylethyl]3-azabicyclo[3.1.0]hexane

To a solution of N-(2-cyanoethyl)-N-[(1S)-phenylethyl]-3-amino-1,2-dibromopropane (37.4 g, 0.1 mol) in toluene (700 ml) cooled in an ice bath was added dropwise 1M tetrahydrofuran solution of sodium (bistrimethylsilyl)amide (220 ml, 0.22 mol), followed by 20 minutes of stirring. After completion of the reaction, saturated ammonium chloride aqueous solution (100 ml) was added dropwise to the reaction solution which was subsequently warmed to room temperature. The organic layer was separated, washed with saturated brine and then dried over sodium sulfate. After evaporation of the solvent, the resulting residue was applied to a silica gel column chromatography and eluted with n-hexane-ethyl acetate (9:1) to yield 7.93 g (37%) of low polarity fraction (Fr. 1) of the title compound and then 7.85 g (36%) of high polarity fraction (Fr. 2) of the title compound.

Fr. 1;

$^1$H-NMR (CDCl$_3$) δ: 1.09 (1H, dd, J=4.5, 8.3 Hz), 1.29 (3H, d, J=6.4 Hz), 1.57 (1H, t, J=4.5 Hz), 1.95–1.99 (1H, m), 2.27 (1H, dd, J=3.9, 9.8 Hz), 2.61 (1H, d, J=8.8 Hz), 2.68 (1H, d, J=9.8 Hz), 3.33–3.38 (2H, m), 7.21–7.31 (5H, m).

Fr. 2;

$^1$H-NMR (CDCl$_3$) δ: 1.09 (1H, dd, J=4.9, 8.3 Hz), 1.29 (3H, d, J=6.4 Hz), 1.55–1.58 (1H, m), 2.04–2.09 (1H, m), 2.35 (1H, d, J=8.8 Hz), 2.53 (1H, dd, J=3.9, 9.3 Hz), 2.86 (1H, d, J=9.3 Hz), 3.18 (1H, d, J=9.3 Hz), 3.32–3.37 (1H, m), 7.21–7.32 (5H, m).

Reference Example A-4

3[(1S)-Phenylethyl]-3-azabicyclo[3.1.0]hexane-1-carboxylicacid (Fr. 1)

To a solution of 1-cyano-3-[(1S)-phenylethyl]-3-azabicyclo[3.1.0]hexane (Fr. 1, 5.6 g, 26.4 mmol) in methanol (500 ml) was added 2N sodium hydroxide aqueous solution (50 ml), followed by 30 hours of heating under reflux. After evaporation of methanol, the resulting residue was washed with chloroform (30 ml×2), adjusted to pH 3 with concentrated hydrochloric acid and then extracted with n-butanol (80 ml×3). The extract was dried over sodium sulfate and then the solvent was evaporated to give 6.11 g (100%) of the title compound in a crude form. This was directly used in the following reaction.

Reference Example A-5

3-[(1S)-Phenylethyl]-3-azabicyclo[3.1.0]hexane-1-carboxylicacid

Fr. 2 was also subjected to the same reaction.

Reference Example A-6

1Tert-butoxycarbonylamino-3-[(1S)-phenylethyl]-3-azabicyclo-[3.1.0]hexane (Fr. 1)

To a solution of 3-[(1S)-phenylethyl]-3-azabicyclo[3.1.0]hexane-1-carboxylic acid (Fr. 1, 6.11 g, 26.4 mmol) in tertiary butanol (200 ml) were added diphenylphosphoric acid azide (9.99 g, 34.3 mmol) and triethylamine (4.23 g, 36.9 mmol), followed by 4 hours of heating under reflux. After cooling the reaction solution, the solvent was evaporated and the resulting residue was mixed with 200 ml of ethyl acetate, washed with saturated brine (50 ml×2) and then dried over sodium sulfate. After evaporation of the solvent, the resulting residue was applied to a silica gel column chromatography and eluted with n-hexane-ethyl acetate (4:1) to give 3.19 g (40%) of the title compound.

$^1$H-NMR (CDCl$_3$) δ: 0.67–0.71 (1H, m), 1.25–1.31 (4H, m), 1.45 (9H, s), 1.60 (1H, brs.), 2.30–2.38 (1H, m), 2.51–2.58 (2H, m), 3.20–3.35 (2H, m), 4.96 (1H, brs.), 7.20–7.29 (5H, m).

Reference Example A-7

1-Tert-butoxycarbonylamino-3-[(1S)-phenylethyl]-3-azabicyclo-[3.1.0]hexane (Fr. 2)

$^1$H-NMR (CDCl$_3$) δ: 0.69–0.71 (1H, m), 1.25 (3H, d, J=6.4 Hz), 1.39 (9H, s), 1.50–1.72 (2H, m), 2.29 (1H, d, J=8.3 Hz), 2.58–2.82 (2H, m), 3.08–3.15 (1H, m), 3.30–3.38 (1H, m), 4.82 (1H, brs.), 7.19–7.37 (5H, m).

Reference Example A-8

1-Tert-butoxycarbonylamino-3-azabicyclo[3.1.0]hexane (Fr. 1)

To a solution of 1-tert-butoxycarbonylamino-3-[(1S)-phenylethyl]-3-azabicyclo[3.1.0]hexane (Fr. 1, 3.1 g, 10.26 mmol) in ethanol (50 ml) was added 10% palladium carbon (3 g), followed by 3 hours of catalytic hydrogenation under warming by a tungsten lamp and under a pressure of 4 atmospheres. After removing the catalyst by filtration, the solvent was evaporated to yield 2.04 g (100%) of the title compound.

$^1$H-NMR (CDCl$_3$) δ: 0.85–1.14 (2H, m), 1.44 (9H, s), 1.44–1.70 (1H, m), 2.95–3.34 (4H, m), 5.08 (1H, brs.).

Reference Example B-1

1-Cyclobutenecarboxylic acid

After stopping heating of a reflux solution of 85% potassium hydroxide and 125 ml of toluene, 10 g (48.31 mmol) of 1-bromocyclobutenecarboxylic acid ethyl ester was added dropwise to the solution at such a rate that the reflux was continued. After completion of the dropwise addition, the resulting mixture was again heated under reflux for 1 hour. After cooling to room temperature, water was added thereto, and the resulting water layer was separated. This was washed with hexane, acidified with 1N hydrochloric acid and then extracted with ether. The organic layer was washed with water and saturated brine and dried over anhydrous sodium sulfate. By evaporating the solvent, 4.1047 g (41.88 mmol, 86.7%) of the title compound was obtained as a crude product.

Reference Example B-2

1-Cyclobutenecarboxylic acid ethyl ester

To a solution of 3.2425 g (33.09 mmol) of 1-cyclobutenecarboxylic acid in 60 ml of dimethylformamide were added 12 ml (150 mmol) of ethyl iodide and 5.53 g (40 mmoL) of potassium carbonate, followed by 20 hours of stirring at room temperature. The reaction solution was poured into water and extracted with ether. The organic layer was washed with water and saturated brine and then dried over anhydrous sodium sulfate. By evaporating the solvent, 4.5267 g of the title compound was obtained as a mixture with ethyl iodide and ether.

$^1$H-NMR (400 MHz, CDCl$_3$) δ: 1.29 (3H, t, J=7.5 Hz), 2.47 (1H, dt, J=1.0, 3.0 Hz), 2.73 (1H, t, J=3.0 Hz), 4.19 (2H, q, J=7.5 Hz), 6.77 (1H, t, J=1.0 Hz).

Reference Example B-3

3-[(S)-Phenylethyl]-3-azabicyclo[3.2.0]heptane-1-carboxylic acid ethyl ester

With cooling in an ice bath, 0.116 ml (1.5 mmol) of trifluoroacetic acid was added dropwise to 4.5267 g (33.09 mmol) of the above mixture of 1-cyclobutenecarboxylic acid ethyl ester with ethyl iodide and ether, and a solution of 14.65 g (50 mmol) of azomethinylide in dichloromethane (100 ml), followed by 64 hours of stirring at room temperature. The reaction solution was poured into saturated sodium bicarbonate aqueous solution and extracted with chloroform. The organic layer was washed with water and saturated brine, and then dried on anhydrous sodium sulfate. After evaporation of the solvent, the resulting residue was purified by a silica gel column chromatography (n-hexane:ethyl acetate=10:1) to yield 4.1832 g (14.58 mmol, 44.1% for 2 steps from Reference Example B-2) of the title compound as a diastereomer mixture. This mixture was separated by a high performance liquid chromatography to yield 1.9203 g (6.69 mmol, 20.2% for 2 steps from Reference Example B-2) of a low porality substance (fr. 1) and 990.5 mg (3.45 mmol, 10.4% for 2 steps from Reference Example B-2) of a high porality substance (fr. 2).

Low porality substance (fr. 1)

$^1$H-NMR (400 MHz, CDCl$_3$) δ: 1.21 (3H, t, J=7.0 Hz), 1.40 (3H, d, J=6.5 Hz), 1.77–1.84 (1H, m), 1.97–2.05 (1H, m), 2.11–2.20 (1H, m), 2.29 (1H, dd, J=6.0, 9.0 Hz), 2.38 (1H, dt, J=6.5, 11.0 Hz), 2.69 (1H, d, J=9.0 Hz), 2.96 (1H, dt, J=5.0, 9.5 Hz), 3.07 (1H, d, J=9.0 Hz), 3.29 (1H, q, J=6.5 Hz), 4.10 (2H, q, J=7.0 Hz), 7.21–7.33 (3H, m), 7.39–7.41 (2H, m).

High porality substance (fr. 2)

$^1$H-NMR (400 MHz, CDCl$_3$) δ: 1.28 (3H, t, J=7.5 Hz), 1.40 (3H, d, J=6.5 Hz), 1.68–1.72 (1H, m), 2.02–2.18 (3H, m), 2.41 (1H, d, J=9.0 Hz), 2.45–2.50 (1H, m), 2.55 (1H, d, J=9.0 Hz), 2.82–2.87 (1H, m), 3.19 (1H, d, J=9.0 Hz), 3.29 (1H, q, J=6.5 Hz), 4.10 (2H, q, J=7.5 Hz), 7.21–7.41 (5H, m).

Reference Example B-4

3-Benzyloxycarbonyl-3-azabicyclo[3.2.0]heptane-1-carboxylicacid ethyl ester (fr. 1)

To a solution of 980 mg (3.41 mmol) of 3-[(S)-phenylethyl]-3-azabicyclo[3.2.0]heptane-1-carboxylic acid ethyl ester in dichloromethane (20 ml) was added dropwise 0.714 ml (5.0 mmol) of benzyl chloroformate under ice cooling, followed by 40 hours of stirring at room temperature. After evaporation of the solvent, the resulting residue was purified by a column chromatography (n-hexane:ethyl acetate=4:1) to give 921.5 mg (2.91 mmol, 85.3%) of the title compound.

Reference Example B-5

3-Benzyloxycarbonyl-3-azabicyclo[3.2.0]heptane-1-carboxylicacid ethyl ester (fr. 2)

To a solution of 863.8 mg (3.01 mmol) of 3-[(S)-phenylethyl]-3-azabicyclo[3.2.0]heptane-1-carboxylic acid ethyl ester in dichloromethane (15 ml) cooled in an ice bath was added dropwise 0.642 ml (4.5 mmol) of benzyl chloroformate, followed by 45 hours of stirring at room temperature. After evaporation of the solvent, the resulting residue was purified by a column chromatography (n-hexane:ethyl acetate=4:1) to give 829 mg (2.62 mmol, 87.0%) of the title compound.

$^1$H-NMR (400 MHz, CDCl$_3$) δ: 1.27 (3H, t, J=7.0 Hz), 1.72 (1H, br), 1.97 (1H, br), 2.22 (1H, br), 2.56 (1H, dt, J=8.0, 11.5 Hz), 3.10 (1H, dd, J=6.5, 14.5 Hz), 3.38–3.42 (1H, m), 3.66–3.84 (3H, m), 4.18 (2H, q, J=7.0 Hz), 5.18 (2H, s), 7.27–7.40 (5H, m).

Reference Example B-6

3-Benzyloxycarbonyl-3-azabicyclo[3.2.0]heptane-1-carboxylicacid (fr. 1)

To a solution of 920 mg (2.90 mmol) of 1-ethoxycarbonyl-3-benzyloxycarbonyl-3-azabicyclo[3.2.0]heptane in ethanol (10 ml) cooled in an ice bath was added 6 ml of 1N sodium hydroxide aqueous solution, followed by 2 hours of stirring at room temperature. After neutralization with 1N hydrochloric acid aqueous solution, ethanol was evaporated. The resulting residue was mixed with 1N hydrochloric acid aqueous solution and extracted with chloroform. The organic layer was washed with saturated brine and dried over anhydrous sodium sulfate. By evaporating the solvent, 847.2 mg (quantitative) of the title compound was obtained as a crude product.

Reference Example B-7

3-Benzyloxycarbonyl-3-azabicyclo[3.2.0]heptane-1-carboxylicacid (fr. 2)

To a solution of 825 mg (2.60 mmol) of 1-ethoxycarbonyl-3-benzyloxycarbonyl-3-azabicyclo[3.2.0]heptane in ethanol (10 ml) cooled in an ice bath was added 5 ml of 1N sodium hydroxide aqueous solution, followed by 2 hours of stirring at room temperature. After neutralization with 1N hydrochloric acid aqueous solution, ethanol was evaporated. The resulting residue was mixed with 1N hydrochloric acid aqueous solution and extracted with chloroform. The organic layer was washed with saturated brine and dried over anhydrous sodium sulfate. By evaporating the solvent, 776.6 mg (quantitative) of the title compound was obtained as a crude product.

$^1$H-NMR (400 MHz, CDCl$_3$) δ:

1.75 (1H, br), 2.00 (1H, br), 2.25 (1H, br), 2.59–2.66 (1H, m), 3.14–3.19 (1H, m), 3.39–3.44 (1H, m), 3.66–3.81 (2H, m), 3.84–3.91 (1H, m), 5.18 (2H, s), 7.29–7.39 (5H, m).

Reference Example B-8

1-Tert-butoxycarbonyl-3-benzyloxycarbonyl-3-azabicyclo[3.2.0]heptane (fr. 1)

To a solution of 3-benzyloxycarbonyl-3-azabicyclo[3.2.0]heptane-1-carboxylic acid (2.90mmol) in tertiary butanol (15 ml) were added 0.53 ml (3.8 mmol) of triethylamine and 0.819 ml (3.8 mmol) of diphenylphosphorylazide, followed by 9 hours of stirring at 70° C. After cooling to room temperature, the reaction solution was poured into saturated sodium bicarbonate and extracted with ethyl acetate. The organic layer was washed with water and saturated brine and dried over anhydrous sodium sulfate. After evaporation of the solvent, the resulting residue was purified by a silica gel column chromatography (n-hexane:ethyl acetate=4:1) to give 817.8 mg (2.27 mmol, 78.3% for 2 steps from Reference Example B-2) of the title compound.

Reference Example B-9

1-Tert-butoxycarbonyl-3-benzyloxycarbonyl-3-azabicyclo-[3.2.0]heptane (fr. 2)

To a solution of 3-benzyloxycarbonyl-3-azabicyclo[3.2.0]heptane-1-carboxylic acid (2.60 mmol) in tertiary butanol (15 ml) were added 0.474 ml (3.4 mmol) of triethylamine and 0.733 ml (3.4 mmol) of diphenylphosphorylazide, followed by 9 hours of stirring at 70° C. After cooling to room temperature, the reaction solution was poured into saturated sodium bicarbonate and extracted with ethyl acetate. The organic layer was washed with water and saturated brine and dried over anhydrous sodium sulfate. After evaporation of the solvent, the resulting residue was purified by a silica gel column chromatography (n-hexane:ethyl acetate=4:1) to give 642.2 mg (1.78 mmol, 68.4% for 2 steps from Reference Example B-7) of the title compound.

$^1$H-NMR (400 MHz, CDCl$_3$) δ: 1.43 (9H, s), 2.18 (3H, br), 2.85 (1H, br), 3.45–3.65 (3H, m), 3.87 (1H, br), 4.80 (1H, br), 5.16 (2H, s), 7.31–7.37 (5H, m).

Reference Example B-10

1-Tert-butoxycarbonyl-3-azabicyclo[3.2.0]heptane (fr. 1)

To a solution of 368 mg (1.02 mmol) of 1-tert-butoxycarbonyl-3-benzyloxycarbonyl-3-azabicyclo[3.2.0]heptane in methanol (20 ml) was added 400 mg of 20% palladium hydroxide-carbon, followed by vigorous stirring in an atmosphere of hydrogen gas. After removing insoluble material by filtration through celite, the resulting filtrate was concentrated to give 274.6 mg of the title compound as a crude product.

Reference Example B-11

1-Tert-butoxycarbonyl-3-azabicyclo[3.2.0]heptane (fr. 2)

To a solution of 360 mg (1.02 mmol) of 1-tert-butoxycarbonyl-3-benzyloxycarbonyl-3-azabicyclo[3.2.0]heptane in methanol (20 ml) was added 400 mg of 20% palladium hydroxide-carbon, followed by vigorous stirring in an atmosphere of hydrogen gas. After removing insoluble material by filtration through celite, the resulting filtrate was concentrated to give 243.8 mg of the title compound as a crude product.

$^1$H-NMR (400 MHz, CD$_3$OD) δ: 1.54 (9H, s), 1.76–1.83 (1H, m), 2.31–2.45 (3H, m), 3.07–3.22 (1H, m), 3.40–3.48 (1H, m), 3.51–3.67 (2H, m), 3.68–3.71 (1H, m).

Inventive Example 1

5-Amino-7-(1-amino-3-azabicyclo[3.1.0]hexan-3-yl)
6,8-difluoro-1-[(2S)-fluoro-(1R)-cyclopropyl]-1,4-
dihydro-4-oxoquinoline-3-carboxylic acid (fr. 1)

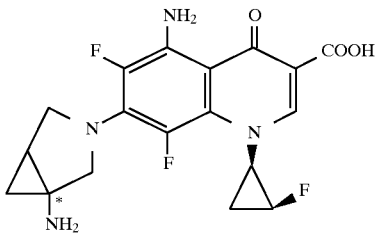

To a solution of 5-amino-6,7,8-trifluoro-1-[(2S)-fluoro-(1R)-cyclopropyl]-1,4-dihydro-4-oxoquinoline-3-carboxylic acid (316 mg, 1 mmol) in acetonitrile (15 ml) were added 1-tert-butoxycarbonylamino-3-azabicyclo[3.1.0]hexane (fr. 1) (396 mg, 2 mmol) and triethylamine (5 ml), followed by 2 hours of heating under reflux. After evaporation of the solvent, the resulting residue was mixed with chloroform (20 ml), washed with 10% citric acid (10 ml×2) and then dried over sodium sulfate, subsequently evaporating the solvent. The resulting residue was mixed with concentrated hydrochloric acid (5 ml) and stirred for 5 minutes at room temperature. The reaction solution was washed with chloroform (5 ml×2), adjusted to pH 7.3 with 20% sodium hydroxide aqueous solution and then extracted with chloroform (30 ml×3). After drying over sodium sulfate, the solvent was evaporated to yield 190 mg (48%) of the title compound as a crude product. Thereafter, 111 mg of the title compound was obtained by recrystallizing the crude product from chloroform-methanol-ethanol.

$^1$H-NMR (0.1 N-NaOD) δ: 0.61–0.64 (1H, m), 0.80–0.83 (1H, m), 1.21–1.83 (3H, m), 3.23–3.79 (5H, m), 4.87–4.98 (0.5H, m), 8.21 (1H, s).

Elementary analysis for $C_{18}H_{18}F_3N_4O_3 \cdot 0.25H_2O$: Calcd.: C, 54.07; H, 4.66; N, 14.01 Found: C, 53.98; H, 4.54; N, 13.82

Melting point (°C.): 191–203 (decomposition)

$[\alpha]_D$ +72.37° (T=22.4° C., c=0.665, 0.1 N-NaOH)

Inventive Example 2

7-(1-Amino-3-azabicyclo[3.1.0]hexan-3-yl)-6-
fluoro-1-[(2S)-fluoro-(1R )-cyclopropyl]-8-methyl-1,
4-dihydro-4-oxoquinoline-3-carboxylic acid (fr. 1)

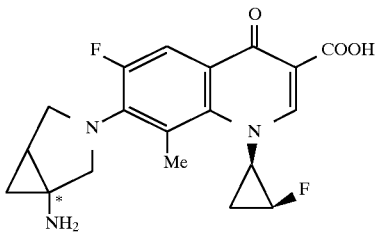

To a solution of 6,7-difluoro-1-[(2S)-fluoro-(1R)-cyclopropyl]-8-methyl-1,4-dihydro-4-oxoquinoline-3-carboxylic acid $BF_2$ chelate (345 mg, 1 mmol) in sulfolane (4 ml) were added 1-tert-butoxycarbonylamino-3-azabicyclo[3.1.0]hexane (fr. 1) (298 mg, 1.5 mmol) and triethylamine (0.2 ml), followed by 200 hours of stirring at room temperature. After evaporation of triethylamine, the resulting residue was mixed with water (10 ml) and stirred for 30 minutes at room temperature. The thus precipitated crystals were washed with water, collected by filtration and dissolved in a mixed solvent of ethanol:water=4:1 (50 ml), and the resulting solution was mixed with triethylamine (5 ml) and heated under reflux for 3 hours. After evaporation of the solvent, the resulting residue was mixed with chloroform (50 ml), washed with 10% citric acid (20 ml×2) and then dried over magnesium sulfate, subsequently evaporating the solvent. The resulting residue was mixed with concentrated hydrochloric acid (5 ml) and stirred for 5 minutes at room temperature. The reaction solution was washed with chloroform (5 ml×2), adjusted to pH 7.3 with 20% sodium hydroxide aqueous solution and then extracted with chloroform (30 ml×3). After drying over sodium sulfate, the solvent was evaporated. The resulting residue was subjected to separation purification by a preparative TLC (developed by the lower layer of chloroform:methanol:water=7:3:1) to yield 35 mg of the title compound as a crude product. Thereafter, 18 mg of the title compound was obtained by recrystallizing the crude product from chloroform-ethanol.

$^1$H-NMR (0.1 N-NaOD) δ: 0.78–0.83 (2H, m), 1.12–1.21 (1H, m), 1.38–1.39 (1H, m), 1.51–1.62 (1H, m), 2.36 (3H, s), 3.03 (1H, d, J=9.3 Hz), 3.31 (1H, d, J=9.3 Hz), 3.56 (1H, d, J=9.3 Hz), 3.72–3.74 (1H, m), 3.99–4.04 (1H, m), 5.00–5.08 (0.5H, m), 7.60 (1H, d, J=13.67 Hz), 8.44 (1H, d, J=2.4 Hz).

Elementary analysis for $C_{19}H_{19}F_2N_3O_3 \cdot 0.75 \, H_2O$: Calcd.: C, 58.68; H, 5.31; N, 10.81 Found: C, 59.01; H, 5.15; N, 10.65

Melting point (°C.): 189–210 (decomposition)

Inventive Example 3

7-(1-Amino-3-azabicyclo[3.1.0]hexan-3-yl)-6-
fluoro-1-[(2S)-fluoro-(1R)-cyclopropyl]-8-methyl-1,
4-dihydro-4-oxoquinoline-3-carboxylic acid (fr. 2)

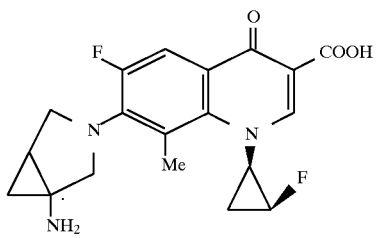

The titled compound was also synthesized in the same manner as described in Inventive Example 2 using fr. 2.

$^1$H-NMR (0.1 N-NaOD) δ: 0.75–0.83 (2H, m), 1.13–1.17 (1H, m), 1.39–1.41 (1H, m), 1.55–1.61 (1H, m), 2.39 (3H, s), 3.26 (1H, d, J=9.3 Hz), 3.35 (1H, d, J 9.3 Hz), 3.47–3.49 (1H, m), 3.55–3.60 (1H, m), 3.98–4.04 (1H, m), 5.01–5.08 (0.5H, m), 7.62 (1H, d, J=13.67 Hz), 8.45 (1H, d, J=1.9 Hz).

Elementary analysis for $C_{19}H_{19}F_2N_3O_3 \cdot 0.25H_2O$: Calcd.: C, 60.07; H, 5.17; N, 11.06 Found: C, 59.87; H, 5.33; N, 10.46

Melting point (°C.): 200–217 (decomposition)

Inventive Example 4

7-(1-Amino-3-azabicyclo[3.1.0]hexan-3-yl)-6-fluoro-1-[(2S)-fluoro-(1R)-cyclopropyl]-8-methoxy-1,4-dihydro-4-oxoquinoline-3-carboxylic acid (fr. 1)

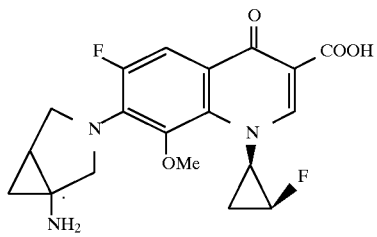

To a solution of 6,7-difluoro-1-[(2S)-fluoro-(1R)-cyclopropyl]-8-methoxy-1,4-dihydro-4-oxoquinoline-3-carboxylic acid BF$_2$ chelate (217 mg, 0.6 mmol) in dimethyl sulfoxide (2.5 ml) were added 1-tert-butoxycarbonylamino-3-azabicyclo-[3.1.0]hexane (fr. 1) (170 mg, 0.86 mmol) and triethylamine (0.2 ml), followed by 150 hours of stirring at room temperature. After evaporation of triethylamine, the resulting residue was mixed with water (10 ml) and stirred for 30 minutes at room temperature. The thus precipitated crystals were washed with water, collected by filtration and dissolved in a mixed solvent of ethanol:water=4:1 (20 ml), and the resulting solution was mixed with triethylamine (3 ml) and heated under reflux for 2 hours. After evaporation of the solvent, the resulting residue was mixed with chloroform (30 ml), washed with 10% citric acid (10 ml×2) and then dried over magnesium sulfate, subsequently evaporating the solvent. The resulting residue was mixed with concentrated hydrochloric acid (5 ml) and stirred for 5 minutes at room temperature. The reaction solution was washed with chloroform (5 ml×2), adjusted to pH 7.3 with 20% sodium hydroxide aqueous solution and then extracted with chloroform (30 ml×3). After drying on sodium sulfate, the solvent was evaporated to yield 175 mg (74%) of the title compound as a crude product. Thereafter, 80 mg of the title compound was obtained by recrystallizing the crude product from chloroformethanol-ether.

$^1$H-NMR (0.1 N-NaOD) δ: 0.67–0.69 (1H, m), 0.82–0.85 (1H, m), 1.40–1.66 (3H, m), 3.42–3.61 (4H, m), 3.54 (3H, s), 3.98–4.03 (1H, m), 4.98–5.05 (0.5H, m), 7.64 (1H, d, J=13.67 Hz), 8.47 (1H, s).

Elementary analysis for C$_{19}$H$_{19}$F$_2$N$_3$O$_4$.0.25H$_2$O: Calcd.: C, 57.65; H, 4.96; N, 10.61 Found: C, 57.53; H, 5.03; N, 10.57

Melting point (°C.): 188–185 (decomposition)

$[α]_D$+138.73° (c=0.395, 0.1 N-NaOH)

Inventive Example 5

7-(1-Amino-3-azabicyclo[3.1.0]hexan-3-yl)-6-fluoro-1-[(2S)-fluoro-(1R)-fluoro-(1R)-cyclopropyl 1-8-methoxy-1,4-dihydro-4-oxoquinoline-3-carboxylic acid (fr. 2)

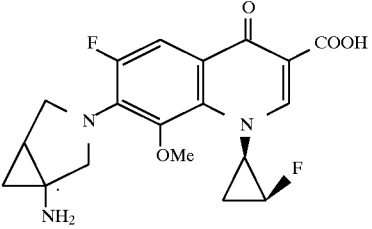

The titled compound was synthesized in the same manner as described in Inventive Example 4 using fr. 2.

$^1$H-NMR (0.1 N-NaOD) δ: 0.72–0.74 (1H, m), 0.86–0.89 (1H, m), 1.44–1.67 (3H, m), 3.39–3.44 (2H, m), 3.58 (3H, s), 3.72 (1H, d, J=7.8 Hz), 3.83 (1H, d, J=9.8 Hz), 4.01–4.06 (1H, m), 5.03–5.06 (0.5H, m), 7.66 (1H, d, J=14.16 Hz), 8.48 (1H, s).

Elementary analysis for C$_{19}$H$_{19}$F$_2$N$_3$O$_3$.0.25H$_2$O: Calcd.: C, 57.65; H, 4.96; N, 10.61 Found: C, 57.61; H, 4.93; N, 10.72

Melting point (°C.): 189–188 (decomposition)

$[α]_D$+45.52° (c=0.303, 0.1 N-NaOH)

Inventive Example 6

7-(1-Amino-3-azabicyclo[3.2.0]hept-3-yl)-6-fluoro-1-[2-(S)-fluoro-1-(R)-cyclopropyl]-8-methoxy-1,4-dihydro-4-oxoquinoline-3-carboxylic acid (fr. 1)

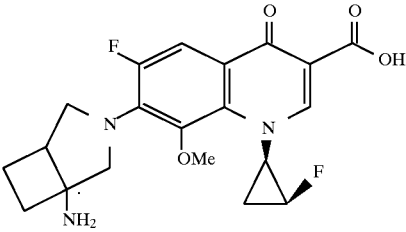

To a solution of 1-tert-butoxycarbonyl-3-azabicyclo[3.2.0]heptane (1.02 mmol) in dimethyl sulfoxide (1.5 ml) were added 180 mg (0.5 mmol) of difluoroboric acid ester of 1-[2-(S)-fluoro-1-(R)-cyclopropyl]-6,7-difluoro-8-methoxy-1,4-dihydro-4-oxoquinoline-3-carboxylic acid and 0.5 ml of triethylamine, followed by 110 hours of stirring at room temperature. After evaporation of triethylamine, the resulting residue was mixed with water, and the thus precipitated crystals were collected by filtration. To the thus collected crystals were added 15 ml of 90% methanol and 3 ml of triethylamine, subsequently carrying out 4 hours of reflux. This was cooled to room temperature and then concentrated. The resulting residue was mixed with 10% citric acid and extracted with chloroform. The organic layer was washed with water and saturated brine and dried on anhydrous sodium sulfate, subsequently evaporating the solvent. To the thus obtained residue dissolved in dichloromethane (5 ml) and cooled in an ice bath was added trifluoroacetic acid (5 ml), followed by 1 hour of stirring at room temperature. After concentration, the resulting residue was mixed with concentrated hydrochloric acid and washed with chloroform. The resulting solution was adjusted to pH 7.5 with concentrated sodium hydroxide aqueous solution and then extracted with chloroform. The extract was dried over anhydrous sodium sulfate, subsequently evaporating the solvent. By recrystallizing the resulting residue from ethanol, 75.9 mg of the title compound was obtained.

$^1$H-NMR (400 MHz, 0.1N NaOD) δ: 1.48–1.70 (3H, m), 2.03–2.24 (3H, m), 2.60 (1H, dd, J=5.5, 13.0 Hz), 3.22 (1H, d, J=10.5 Hz), 3.53 (1H, dd, J=5.5, 9.5 Hz), 3.65–3.71 (2H, m), 3.72 (3H, s), 4.07–4.12 (1H, m), 4.90–5.10 (1H, m), 7.74 (1H, d, J=13.5 Hz), 8.50 (1H, s).

Elementary analysis for $C_{20}H_{21}N_3O_4F_2 \cdot 1/4H_2O$: Calcd.: C, 58.604; H, 5.286; N, 10.251 Found: C, 58.51; H, 5.38; N, 9.94

Melting point (°C.): 233–236

Inventive Example 7

7-(1-Amino-3-azabicyclo[3.2.0[hept-3-yl)-6-fluoro-1-[2-(S)-fluoro-1-(R)-cyclopropyl]-8-methoxy-1,4-dihydro-4-oxoquinoline-3-carboxylic acid (fr. 2)

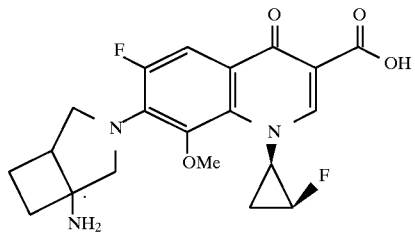

To a solution of 1-tert-butoxycarbonyl-3-azabicyclo-[3.2.0]heptane (0.778 mmol) in dimethyl sulfoxide (1.5 ml) were added 180 mg (0.5 mmol) of difluoroboric acid ester of 1-[2-(S)-fluoro-1-(R)-cyclopropyl]-6,7-difluoro-8-methoxy-1,4-dihydro-4-oxoquinoline-3-carboxylic acid ($BF_2$ chelate) and 0.5 ml of triethylamine, followed by 115 hours of stirring at room temperature. After evaporation of triethylamine, the resulting residue was mixed with water, and the thus precipitated crystals were collected by filtration. To the thus collected crystals were added 15 ml of 90% methanol and 3 ml of triethylamine, subsequently carrying out 4 hours of reflux. This was cooled to room temperature and then concentrated. The resulting residue was mixed with 10% citric acid and extracted with chloroform. The organic layer was washed with water and saturated brine, and dried over anhydrous sodium sulfate, subsequently evaporating the solvent. To the thus obtained residue dissolved in dichloromethane (5 ml) and cooled in an ice bath was added trifluoroacetic acid (5 ml), followed by 1 hour of stirring at room temperature. After concentration, the resulting residue was mixed with concentrated hydrochloric acid and washed with chloroform. The resulting solution was adjusted to pH 7.5 with concentrated sodium hydroxide aqueous solution and then extracted with chloroform. The extract was dried over anhydrous sodium sulfate, subsequently evaporating the solvent. By recrystallizing the resulting residue from ethanol, 101.6 mg of the title compound was obtained.

$^1$H-NMR (400 MHz, 0.1N NaOD) δ: 1.34–1.54 (3H, m), 1.89–2.02 (2H, m), 2.01–2.14 (2H, m), 2.44–2.47 (1H, m), 2.92 (1H, d, J=10.5 Hz), 3.35 (1H, d, J=10.5 Hz), 3.51–3.56 (4H, m), 3.74 (1H, d, J=10.5 Hz), 3.90–3.95 (1H, m), 4.70–4.91 (1H, m), 7.57 (1H, d, J=13.5 Hz), 8.34 (1H, s).

Elementary analysis for $C_{20}H_{21}N_3O_4F_2$: Calcd.: C, 59.236; H, 5.224; N, 10.369 Found: C, 59.28; H, 5.32; N, 10.17

Melting point (°C.): 238–240

Inventive Example 8

5-Amino-7-[(3R,1'S)-3-(1-aminoethyl)-1-pyrrolidinyl]-1-cyclopropyl-6-fluoro-1,4-dihydro-8-methyl-4-oxoquinoline-3-carboxylic acid A 626 mg (2.92 mmol) portion of (3R,1'S)-3-(1-tert-butoxycarbonylaminoethyl)pyrrolidine was suspended in 10 ml of dimethyl sulfoxide to which were subsequently added 437 mg (1.46 mmol) of 5-amino-1-cyclopropyl-6,7-difluoro-8-methyl-1,4-dihydro-4-oxoquinoline-3-carboxylic acid and 2.80 ml of triethylamine, followed by 21 hours of heating at 150°–160° C. in a stream of nitrogen. After evaporation of the solvent, the resulting residue was mixed with chloroform, washed with water, 10% citric acid aqueous solution and saturated brine in that order, and then dried over anhydrous sodium sulfate. After evaporation of the solvent, the thus obtained tertiary butylcarbamate compound was mixed with 4 ml of concentrated hydrochloric acid, and the mixture was stirred for 20 minutes at room temperature, washed with chloroform (50 ml×3), adjusted to pH 7.4 with sodium hydroxide aqueous solution and then extracted with chloroform. The extract was dried over anhydrous sodium sulfate and the solvent was evaporated. By recrystallizing the resulting residue from ethanol-ether, 369 mg (65%) of the title compound was obtained.

Melting point: 106°–107° C.

$[\alpha]_D^{25}$=–15.48 (c=0.394, 0.1N sodium hydroxide aqueous solution)

$^1$H-NMR (400 MHz, 0.1N NaOD) δ: 0.63 (1H, br s), 0.75 (1H, br s), 1.02–1.18 (5H, m), 1.54–1.58 (1H, m), 1.99–2.10 (2H, m), 2.29 (3H, s), 2.79 (1H, br s), 3.31–3.44 (3H, m), 3.58–3.60 (1H, m), 3.91 (1H, br s), 8.37 (1H, s).

Elementary analysis for $C_{20}H_{25}N_4O_3F \cdot 1/2 H_2O$: Calcd.: C, 60.44; H, 6.59; N, 14.10 Found: C, 60.35; H, 6.55; N, 14.30

Inventive Example 9

5-Amino-7-[(3R,1'S)-3-(1-aminoethyl)-1-pyrrolidinyl]-6-fluoro-1-[(1R,2S)-2-fluorocyclopropyl]-1,4-dihydro-8-methyl-4-oxoquinoline-3-carboxylic acid A 394 mg (1.84 mmol) portion of (3R,1'S)-3-(1-tert-butoxycarbonylaminoethyl)pyrrolidine was suspended in 10 ml of dimethyl sulfoxide to which were subsequently added 317 mg (1.00 mmol)of5-amino-6,7-difluoro-1-[(1R,2S)-2-fluorocyclopropyl]-8-methyl-1,4-dihydro-4-oxoquinoline-3-carboxylic acid and 2.00 ml of triethylamine, followed by 18 hours of heating at 150°–160° C. in a stream of nitrogen. After evaporation of the solvent, the resulting residue was mixed with chloroform, washed with water, 10% citric acid aqueous solution and saturated brine in that order, and then dried over anhydrous sodium sulfate. After evaporation of the solvent, the thus obtained tertiary butylcarbamate compound was mixed with 3 ml of concentrated hydrochloric acid, and the mixture was stirred for 10 minutes at room temperature, washed with chloroform (50 ml×3), adjusted to pH 7.4 with sodium hydroxide aqueous solution and then extracted with chloroform. The extract was dried over anhydrous sodium sulfate and the solvent was evaporated. The resulting residue was purified by a preparative TLC (chloroform:methanol:water=7:3:1), and the resulting crude product was recrystallized from ethanol to yield 118 mg (29%) of the title compound.

Melting point: 225°–226° C.

$[\alpha]_D^{25}$=−305.07 (c=0.276, 0.1N sodium hydroxide aqueous solution)

$^1$H-NMR (400 MHz, 0.1N NaOD) δ: 1.11–1.19 (4H, m), 1.48–1.59 (2H, m), 2.09–2.13 (2H, m), 2.29 (3H, s), 2.84 (1H, br s), 3.30 (1H, br s), 3.41 (1H, br s), 3.52 (1H, br s), 3.78 (1H, br s), 3.94 (1H, br s), 8.26 (1H, 2 s).

Elementary analysis for $C_{20}H_{22}N_4O_3F_2 \cdot 9/4H_2O$: Calcd.: C, 53.74; H, 6.43; N, 12.54 Found: C, 53.80; H, 6.02; N, 12.48

Reference Example C-1

(3R)-Ethyl 1-benzyloxycarbonylpyrrolidine-3-acetate

A 12 g (45.9 mmol) portion of (3R)-ethyl 1-[(R)-1-phenylethyl]pyrrolidine-3-acetate known in literatures was dissolved in 100 ml of dichloromethane to which was subsequently added dropwise 7.87 ml (55.1 mmol) of benzyl chloroformate at room temperature. After completion of the dropwise addition, the mixture was stirred for 16 hours at the same temperature. After completion of the reaction, the reaction mixture was concentrated. Thereafter, the resulting residue was applied to a silica gel column chromatography to yield 10.1 g (76%) of the title compound as an oily substance from the eluate of n-hexane:ethyl acetate=5:1.

$^1$H-NMR (400 MHz, CDCl$_3$) δ: 1.26 (3H, t, J=7.32 Hz), 1.53–1.64 (1H, m), 2.07–2.15 (1H, m), 2.36–2.42 (2H, m), 2.55–2.67 (1H, m), 3.01–3.07 (1H, m), 3.36–3.42 (1H, m), 3.49–3.62 (1H, m), 3.67–3.73 (1H, m), 4.14 (2H, q, J=7.32 Hz), 5.13 (2H, s), 7.29–7.38 (5H, m).

Reference Example C-2

Diethyl 1-benzyloxycarbonyl-3-(R)-pyrrolidinylmalonate

A 146 mg (0.5 mmol) portion of (3R)-ethyl 1-benzyloxycarbonylpyrrolidine-3-acetate was dissolved in 3 ml of tetrahydrofuran (THF) to which was subsequently added 1 ml (1 mmol) of 1 mol tetrahydrofuran solution of sodium (bistrimethylsilyl)amide at −78° C. After 30 minutes of stirring at the same temperature, 2 ml of tetrahydrofuran solution of 0.12 ml (1 mmol) ethyl chloroformate was added dropwise to the reaction solution at −78° C. and stirred for 2 hours at the same temperature. After completion of the reaction, 5 ml of 1N hydrochloric acid was added dropwise to the reaction solution which was subsequently warmed to room temperature. The reaction solution was mixed with 40 ml of ethyl acetate, washed with saturated sodium bicarbonate aqueous solution (50 ml×1) and saturated brine (50 ml×1) in that order, and then dried on magnesium sulfate. After evaporation of the solvent, the resulting residue was applied to a silica gel column chromatography to yield 150 mg (83%) of the title compound as an oily substance from the eluate of n-hexane:ethyl acetate=4:1.

$^1$H-NMR (400 MHz, CDCl$_3$) δ: 1.24–1.29 (6H, m), 1.60–1.75 (1H, m), 2.03–2.19 (1H, m), 2.79–2.91 (1H, m), 3.09–3.17 (1H, m), 3.28 (1H, d, J=9.76 Hz), 3.32–3.41 (1H, m), 3.55–3.65 (1H, m), 3.72–3.77 (1H, m), 4.17–4.24 (4H, m), 5.13 (2H, s), 7.28–7.59 (5H, m).

Reference Example C-3

Ethyl hydrogen 1-benzyloxycarbonyl-3-(R)-pyrrolidinylmalonate

A 177 mg (0.49 mmol) portion of diethyl 1-benzyloxycarbonyl-3-(R)-pyrrolidinemalonate was dissolved in 10 ml of ethanol. To the solution was added dropwise a solution of 32 mg (0.49 mmol) of potassium hydroxide (85 %) in 10 ml of ethanol under ice cooling. After completion of the dropwise addition, the reaction solution was stirred at room temperature for 18 hours. After completion of the reaction, 20 ml of water was added to the reaction solution and then ethanol was evaporated. The remaining aqueous layer was washed with dichloromethane (50 ml×2). The resulting aqueous layer was acidified with concentrated hydrochloric acid and then extracted with diethyl ether (50 ml×3). The organic layers were combined and dried over magnesium sulfate, and then the solvent was evaporated to yield 160 mg (97%) of the title compound as an oily substance.

$^1$H-NMR (400 MHz, CDCl$_3$) δ: 1.23–1.30 (3H, m), 1.63–1.71 (1H, m), 2.09–2.20 (1H, m), 2.79–2.90 (1H, m), 3.10–3.20 (1H, m), 3.28–3.43 (2H, m), 3.51–3.65 (1H, m), 3.71–3.84 (1H, m), 4.19–4.25 (2H, m), 5.13 (2H, s), 7.28–7.55 (5H, m).

Reference Example C-4

Ethyl 2-(1-benzyloxycarbonyl-3-(R)-pyrrolidinyl) acrylate

A 1.94 g (5.78 mmol) of ethyl hydrogen 1-benzyloxycarbonyl-3-(R)-pyrrolidinylmalonate and 2.18 g (11.56 mmol) of Eschenmoser's salt were dissolved in 200 ml of acetonitrile, and the solution was mixed with a catalytically effective amount of potassium acetate and heated under reflux for 12 hours. After completion of the reaction, acetonitrile was evaporated, and the resulting residue was mixed with 200 ml of ethyl acetate, washed with 10% citric acid (50 ml×1), 10% sodium sulfite aqueous solution (50 ml×1) and saturated brine (50 ml×1) in that order. After drying the organic layer over sodium sulfate, the solvent was evaporated. Thereafter, the resulting residue was applied to a silica gel column chromatography to yield 1.12 g (64%) of the title compound as an oily substance from the eluate of n-hexane:ethyl acetate=5:1.

$^1$H-NMR (400 MHz, CDCl$_3$) δ: 1.31 (3H, t, J=7.33 Hz), 1.53–1.62 (1H, m), 1.79–1.89 (1H, m), 2.11–2.21 (1H, m), 3.18–3.31 (2H, m), 3.38–3.48 (1H, m), 3.51–3.63 (1H, m), 4.22 (2H, q, J=7.33 Hz), 5.14 (2H, s), 5.58 (1H, s), 6.26 (1H, d, J=1.96 Hz), 7.29–7.38 (5H, m).

Reference Example C-5

Ethyl 1-(1-benzyloxycarbonyl-3-(R)-pyrrolidinyl) cyclopropanecarboxylate

To a mixture of 852 mg (2.8 mmol) of ethyl 2-(1-benzyloxycarbonyl-3-(R)-pyrrolidinyl)acrylate and 5 mg (0.02 mmol) of palladium acetate was added 100 ml of diethyl ether, followed by dropwise addition of a solution of excess (10 equivalents) diazomethane in diethyl ether while ice cooling. After completion of the dropwise addition, the reaction mixture was stirred at room temperature for 30 minutes. After completion of the reaction, the solvent was evaporated and the resulting residue was applied to a silica gel column chromatography to yield 890 mg (quantitative) of the title compound as an oily substance from the eluate of n-hexane:ethyl acetate=3:1.

$^1$H-NMR (400 MHz, CDCl$_3$) δ: 0.71–0.82 (2H, m), 1.19–1.28 (5H, m), 1.43–1.59 (1H, m), 1.84–1.95 (1H, m), 2.73–2.85 (1H, m), 2.93 (1H, dd, J=10.25Hz, 18.55 Hz), 3.28–3.39 (1H, m), 3.55–3.75 (2H, m), 4.09–4.15 (2H, m), 5.13 (2H, s), 7.28–7.36 (5H, m).

Reference Example C-6

1-(1-Benzyloxycarbonyl-3-(R)-pyrrolidinyl)cyclopropanecarboxylic acid

A 5.26 g (16.6 mmol) portion of ethyl 1-(1-benzyloxycarbonyl-3-(R)-pyrrolidinyl)cyclopropanecarboxylate was dissolved in 300 ml of ethanol, and the solution was cooled in an ice bath, mixed with 16.6 ml of 10N sodium hydroxide aqueous solution and then stirred at room temperature for 5 days. After completion of the reaction, ethanol was evaporated, and the remaining water layer was then acidified with hydrochloric acid and extracted with diethyl ether (50 ml×4). The organic layers were combined and dried over magnesium sulfate and then the solvent was evaporated to yield 4.95 g of the title compound quantitatively as an oily substance.

1-H-NMR (400 MHz, CDCl$_3$) δ: 0.75–0.85 (2H, m), 1.22–1.33 (2H, m), 1.45–1.61 (1H, m), 1.82–1.98 (1H, m), 2.69–2.78 (1H, m), 2.93–3.01 (1H, m), 3.25–3.36 (1H, m), 3.55–3.75 (2H, m), 5.12 (2H, s), 7.28–7.35 (5H, m), 11.09 (1H, br s).

Reference Example C-7

(3R)-1-Benzyloxycarbonyl-3-(1-tert-butoxycarbonylaminocyclopropyl)pyrrolidine

A 289 mg (1 mmol) portion of 1-(1-benzyloxycarbonyl-3-(R)-pyrrolidinyl)cyclopropanecarboxylic acid was dissolved in 10 ml of tert-butanol. To this solution were added dropwise 0.28 ml (1.3 mmol) of diphenylphosphoric acid azide and 0.24 ml (1.6 mmol) of triethylamine in that order at room temperature, followed by 2 hours of stirring at the same temperature. After confirming formation of the acid azide, the reaction temperature was increased to carry out 18 hours of heating under reflux. After completion of the reaction, the solvent was evaporated and the resulting residue was applied to a silica gel column chromatography to yield 263 mg (73%) of the title compound as an oily substance from the eluate of n-hexane:ethyl acetate=4:1.

$^1$H-NMR (400 MHz, CDCl$_3$) δ: 0.65–0.85 (4H, m), 1.41 (9H, s), 1.59–1.75 (1H, m), 1.95–2.00 (1H, m), 2.20–2.35 (1H, m), 3.07–3.15 (1H, m), 3.27–3.35 (1H, m), 3.51–3.65 (2H, m), 4.87 (1H, d, J=10.3 Hz), 5.13 (2H, s), 7.29–7.37 (5H, m).

$[\alpha]_D^{25}$=6.83, (c=0.731, CHCl$_3$)

This product was found to be a 4:1 enantiomer mixture (60% ee) when checked by an HPLC analysis using a chiral column.

Conditions for this analysis are shown below.

Column: DAICEL CHIRALCEL OD, 25 cm×0.46 cm
Mobile phase: n-hexane:isopropanol=95:5
Flow rate: 1.5 ml/min
Temperature: room temperature
Detection: UV (254 nm)
Retention times of the optical isomers are shown below.
(3R) Form: 13.06 min
(3S) Form: 15.65 min A 4 g portion of the 4:1 mixture was recrystallized from acetonitrile to afford 2.65 g of the (3R) form.
$[\alpha]_D^{25}$=10.00, (c=0.660, CHCl$_3$)

Reference Example D-1

Ethyl 1-acetylcyclopropanecarboxylate

A 204 ml (1.6 mol) portion of ethyl acetoacetate and 138 ml (1.6 mol) of 1,2-dibromoethane were dissolved in 3 liters of N,N-dimethylformamide, and the solution was mixed with 460 g (3.3 mol) of potassium carbonate at room temperature and stirred at the same temperature for 2 days. After completion of the reaction, insoluble material was removed by filtration and then N,N-dimethylformamide was evaporated under a reduced pressure of 50 mmHg. The resulting residue was mixed with 1.5 liters of diethyl ether, washed with water (500 ml×3) and then dried over anhydrous sodium sulfate. By evaporating diethyl ether, 113.43 g (45%) of the title compound was obtained as an oily substance.

$^1$H-NMR (400 MHz, CDCl$_3$) δ: 1.29 (3H, t, J=6.84 Hz), 1.47 (4H, s), 2.47 (3H, s), 4.21 (2H, q, J=6.84 Hz).

Reference Example D-2

Ethyl 1-ethoxycarbonyl-β-hydroxy-β-methyl-cyclopropanepropanoate

A 61.7 g (0.39 mol) portion of ethyl 1-acetylcyclopropanecarboxylate was dissolved in 500 ml of benzene to which were subsequently added 13 g of zinc powder and a catalytically effective amount of iodine. While heating under reflux, a solution of 56.2 ml (0.51 mol) of ethyl bromoacetate in 100 ml of benzene was added dropwise to the mixture above. When the reaction started to progress, the dropwise addition was suspended, 39 g of zinc powder was added in small portions and then the remaining ethyl bromoacetate benzene solution was added dropwise. After completion of the addition, the reaction solution was heated under reflux for another 2 hours. The reaction solution was cooled spontaneously, mixed with 500 ml of 1N hydrochloric acid and then filtered through celite. The organic layer was separated, washed with saturated brine (500 ml×2) and then dried over anhydrous sodium sulfate. By evaporating the solvent, 90.31 g (95%) of the title compound was obtained as an oily substance.

$^1$H-NMR (400 MHz, CDCl$_3$) δ: 1.08–1.18 (4H, m), 1.23 (3H, t, J=6.84 Hz), 1.27 (3H, t, J=7.33 Hz), 1.43 (3H, s), 2.91 (1H, d, J=15.14 Hz), 2.98 (1H, d, J=15.14 Hz), 4.09 (2H, q, J=6.84 Hz), 4.19 (2H, dq, J=1.95 Hz, J=6.84 Hz).

Reference Example D-3

(E)-Ethyl 3-(1-ethoxycarbonylcyclopropyl)-2-butenoate

A 90.31 g (0.37 mol) portion of ethyl 1-ethoxycarbonyl-β-hydroxy-β-methyl-cyclopropanepropanoate was dissolved in 182 ml of pyridine to which was subsequently added dropwise thionyl chloride at −10° C. to −5° C. After completion of the dropwise addition, this was stirred at the same temperature for 3 hours. After completion of the reaction, the reaction solution was poured into 1 liter of ice water and extracted with dichloromethane (300 ml×3). The organic layers were combined, washed with 1N hydrochloric acid (1 liter×1) and saturated brine (1 liter×1) in that order and then dried on anhydrous sodium sulfate. To the resulting dichloromethane solution was added dropwise 58 ml of 1,8-diazabicyclo[5,4,0]-7-undecene at 0° C., followed by 18 hours of stirring at room temperature. After completion of the reaction, the reaction solution was washed with 1N hydrochloric acid (1 liter×1) and saturated brine (1 liter×1) in that order, and then dried over anhydrous sodium sulfate. After evaporation of the solvent, the resulting residue was applied to a silica gel column chromatography to yield 56.57 g (68%) of the title compound as an oily substance from the eluate of n-hexane:ethyl acetate=9:1.

¹H-NMR (400 MHz, CDCl₃) δ: 1.01 (2H, dd, J=3.91 Hz, J=6.84 Hz), 1.24 (3H, t, J=7.32 Hz), 1.28 (3H, t, J=7.32 Hz), 1.40 (2H, dd, J=3.91 Hz, J=6.84 Hz), 2.29 (3H, d, J=1.46 Hz), 4.13 (2H, q, J=7.32 Hz), 4.16 (2H, q, J=7.32 Hz), 5.78 (1H, d, J=0.98 Hz).

Reference Example D-4

4-(1-Ethoxycarbonylcyclopropyl)-1-[(S)-1-phenylethyl]-3-pyrrolin-2-one

A 25.37 g (0.11 mol) portion of (E)-ethyl 3-(1-ethoxycarbonylcyclopropyl)-2-butenoate was dissolved in 300 ml of carbon tetrachloride to which were subsequently added 23.9 g (0.13 mol) of N-bromosuccinimide and a catalytically effective amount of azobisisobutyronitrile, followed by 5 hours of reflux under sunlight. After completion of the reaction, the reaction solution was filtered and the resulting filtrate was concentrated. The thus obtained residue was dissolved in 250 ml of ethanol and mixed with 18.83 g (0.22 mol) of sodium bicarbonate. Thereto was added dropwise 15.84 ml (0.12 mol) of (S)-phenylethylamine at a room temperature. After completion of the dropwise addition, this was stirred for 30 minutes at room temperature and then heated for 4 hours under reflux. After completion of the reaction, the solvent was evaporated and the resulting residue was mixed with 500 ml of ethyl acetate, washed with water (500 ml×1), 1N hydrochloric acid (500 ml×2) and saturated brine (500 ml×2) in that order, and then dried over anhydrous sodium sulfate. After evaporation of the solvent, the resulting residue was applied to a silica gel column chromatography to yield 13.1 g (39%) of the title compound as an oily substance from the eluate of n-hexane:ethyl acetate=1:1.

¹H-NMR (400 MHz, CDCl₃) δ: 1.13–1.15 (2H, m), 1.18 (3H, t, J=6.83 Hz), 1.60 (3H, d, J=7.32 Hz), 1.61–1.64 (2H, m), 3.80 (1H, d, J=19.53 Hz), 4.09 (2H, q, J=6.83 Hz), 4.13 (1H, d, J=19.53 Hz), 5.56 (1H, q, J=7.32 Hz), 5.85 (1H, t, J=1.47 Hz), 7.25–7.37 (5H, m).

Reference Example D-5

4-(1-Ethoxycarbonylcyclopropyl)-1-[(S)-1-phenylethyl1-2-pyrrolidone

A 13.1 g (43.8 mmol) portion of 4-(1-ethoxycarbonylcyclopropyl)-1-[(S)-1-phenylethyl]-3-pyrrolin-2-one was dissolved 300 ml of methanol, mixed with 400 mg of platinum oxide and then stirred in an atmosphere of hydrogen for 18 hours. After completion of the reaction, the reaction solution was filtered and concentrated to yield 13.0 g (99 %) of the titled compound as an oily substance.

This product was found to be a mixture of (4S):(4R)=3.5:1 when checked by an NMR analysis.

¹H-NMR (400 MHz, CDCl₃) δ: 0.63–0.65 and 0.71–0.73 (2H, m), 1.11–1.28 (5H, m), 1.51–1.60 (3H, m), 2.14–2.31 (1H, m), 2.43–2.52 [(S)-2H and (R)-1H, m], 2.64–2.76 [(S)-2H, m], 3.14 [(R)-2H, d, J=7.81 Hz], 3.48 [(S)-1H, t, J=8.79 Hz], 3.97–4.15 (2H, m), 5.49 and 5.52 (1H, each q, J=5.86 Hz and 6.84 Hz), 7.14–7.36 (5H, m).

Reference Example D-6

(4S)-4-(1-Ethoxycarbonylcyclopropyl)-1-[(S)-1-phenylethyl]-2-pyrrolidinethion

A 13.04 g (43.3 mmol) portion of 4-(1-ethoxycarbonylcyclopropyl)-1-[(S)-1-phenylethyl]-2-pyrrolidone was dissolved in 500 ml of benzene, mixed with 19.26 g (47.6 mmol) of Lawesson reagent and then heated under reflux for 1 hour. After completion of the reaction, the solvent was evaporated and the resulting residue was applied to a silica gel column chromatography to yield a diastereomer mixture from the eluate of n-hexane:ethyl acetate=3:1. By carrying out fractional recrystallization with n-hexane:isopropyl ether=1:1, 6.81 g (as 62% (4S) content) of the title compound was obtained as needle crystals.

¹H-NMR (400 MHz, CDCl₃) δ: 0.63 (2H, d, J=2.44 Hz), 1.11–1.23 (2H, m), 1.14 (3H, t, J=7.32 Hz), 1.59 (3H, d, J=6.83 Hz), 2.68 (1H, dd, J=8.79 Hz, J=17.48 Hz), 2.79 (1H, dq, J=8.30 Hz), 3.02 (1H, dd, J=7.32 Hz, J=11.23 Hz), 3.09 (1H, dd, J=8.79 Hz, J=17.48 Hz), 3.76 (1H, dd, J=8.30 Hz, J=11.23 Hz), 4.01 (2H, q, J=7.32 Hz), 6.39 (1H, q, J=6.83 Hz), 7.30–7.36 (5H, m).

Reference Example D-7

(3R)-1-Benzyloxycarbonyl-(1-ethoxycarbonylcyclopropyl)pyrrolidine

A 6.81 g (21 mmol) portion of (4S)-4-(1-ethoxycarbonylcyclopropyl)-1-[(S)-1-phenylethyl]-2-pyrrolidinethion was dissolved in 40 ml of ethanol, mixed with 21 ml of Raney nickel and then heated under reflux for 6 hours. After completion of the reaction, the reaction solution was filtered and then ethanol was evaporated. The resulting residue was dissolved in 400 ml of chloroform, washed with 10% aqueous ammonia (500 ml×2), 0.5N hydrochloric acid (500 ml×2) and saturated brine (500 ml×2) in that order, and then dried over anhydrous sodium sulfate. After evaporation of the solvent, the resulting residue was dissolved in 200 ml of dichloromethane to which was subsequently added dropwise 4.57 ml (32 mmol) of benzyl chloroformate. After completion of the dropwise addition, the reaction solution was heated under reflux for 20 hours. After completion of the reaction, the solvent was evaporated and the resulting residue was applied to a silica gel column chromatography to yield 3.62 g (54%) of the title compound as an oily substance from the eluate of n-hexane:ethyl acetate=4:1.

¹H-NMR (400 MHz, CDCl₃) δ: 0.71–0.82 (2H, m), 1.19–1.28 (2H, m), 1.43–1.59 (1H, m), 1.84–1.95 (1H, m), 2.73–2.85 (1H, m), 2.93 (1H, dd, J=10.25Hz, J=18.55 Hz), 3.28–2.39 (1H, m), 3.55–3.75 (2H, m), 4.09–4.15 (2H, m), 5.13 (2H, s), 7.28–7.36 (5H, m).

Reference Example E-1

(3R)-1-Benzyloxycarbonyl-3-1-(N-tert-butoxycarbonyl-N-methyl)aminocyclopropyl] pyrrolidine A 1.27 g (3.52 mmol) portion of (3R)-1-benzyloxycarbonyl-3-(1-tert-butoxycarbonylaminocyclopropyl)pyrrolidine was dissolved in a solvent mixture composed of 22 ml of methyl iodide and 2 ml of N,N-dimethylformamide, mixed with 8.2 g (35.2 mmol) of silver oxide and then heated at 80° C. in a sealed tube for 7 hours. After completion of the reaction, the reaction solution was filtered and the resulting filtrate was concentrated. The resulting residue was applied to a silica gel column chromatography to yield 1.22 g (93%) of the title compound as an oily substance from the eluate of n-hexane:ethyl acetate=3:1.

¹H-NMR (400 MHz, CDCl₃) δ: 0.55–1.00 (4H, m), 1.42, 1.44 and 1.47 (9H, each s), 1.50–1.69 (1H, m), 1.80–1.95

(1H, m), 2.25–2.55 (1H, m), 2.81 and 2.84 (3H, each s), 2.98–3.12 (1H, m), 3.24–3.34 (1H, m), 3.51–3.65 (2H, m), 5.12 (2H, s), 7.30–7.36 (5H, m).

Reference Example E-2

(3R)-1-Benzyloxycarbonyl-3-[1-(N-tert-butoxycarbonyl-N-ethyl)aminocyclopropyl]pyrrolidine A 1.04 g (2.89 mmol) portion of (3R)-1-benzyloxycarbonyl-3-(1-tert-butoxycarbonylaminocyclopropyl)pyrrolidine was dissolved in a solvent mixture composed of 11.6 ml of ethyl iodide and 1 ml of N,N-dimethylformamide, mixed with 6.7 g (28.9 mmol) of silver oxide and then heated at 80° C. in a sealed tube for 4 hours. After completion of the reaction, the reaction solution was mixed with diethyl ether and filtered though celite, and the resulting filtrate was concentrated. The resulting residue was applied to a silica gel column chromatography to yield 831 mg (74%) of the title compound as an oily substance from the eluate of n-hexane:ethyl acetate=4:1.

$^1$H-NMR (400 MHz, CDCl$_3$) δ: 0.5–0.98 (4H, m), 1.05–1.18 (3H, br s), 1.43 and 1.46 (9H, each s), 1.47–1.61 (1H, m), 1.76–1.93 (1H, m), 2.34–2.53 (1H, m), 2.83–3.43 (4H, m), 3.48–3.62 (2H, m), 5.12 (2H, s), 7.32–7.36 (5H, m).

Reference Example E-3

(3R)-3-1-(Benzyloxyacetyl)aminocyclopropyl]-1-benzyloxycarbonylpyrrolidine

To 1.8 g (5.0 mmol) of (3R)-1-benzyloxycarbonyl-3-(1-tert-butoxycarbonylaminocyclopropyl)pyrrolidine cooled in an ice bath was added dropwise 10 ml of trifluoroacetic acid, subsequently stirring the mixture at room temperature for 1 hour. After evaporation of trifluoroacetic acid, the resulting residue was mixed with 80 ml of -tetrahydrofuran and 3.48 ml (25 mmol) of triethylamine. Thereto was added dropwise 0.86 ml (5.5 mmol) of benzyloxyacetyl chloride dissolved in 20 ml of tetrahydrofuran under ice cooling. After 1 hour of stirring at the same temperature, the reaction solution was washed with water (100 ml×1), 10% citric acid (100 ml×1), saturated sodium bicarbonate aqueous solution (100 ml×1) and saturated brine (100 ml×1) in that order. The organic layer was dried over magnesium sulfate and then the solvent was evaporated. The thus obtained crude amide product was immediately used in the next reaction.

Reference Example E-4

(3R)-1-Benzyloxycarbonyl-3-[1-(N-2-benzyloxyethyl-N-tert-butoxycarbonyl aminocyclopropyl]pyrrolidine A 5 mmol portion of (3R)-3-[1-(benzyloxyacetyl)aminocyclopropyl]-1-benzyloxycarbonylpyrrolidine was dissolved in 10 ml of tetrahydrofuran. Thereto was added dropwise 30 ml (30 mmol) of 1 mol tetrahydrofuran solution of boranetetrahydrofuran complex under ice cooling. After completion of the dropwise addition, saturated sodium bicarbonate aqueous solution was added dropwise to the reaction solution to hydrolyze excess borane-tetrahydrofuran complex. When foaming was ceased, 100 ml of saturated sodium bicarbonate aqueous solution and 50 ml of water were added thereto, and the mixture was stirred for 4 days. The tetrahydrofuran layer of the reaction solution was separated, and the water layer was extracted with diethyl ether (100 ml×3). The organic layers were combined and dried over magnesium sulfate, and the solvent was evaporated. The resulting residue was dissolved in 50 ml of acetonitrile, mixed with 1.6 g (7.5 mmol) of di-tert-butyl carbonate and then stirred at room temperature for 18 hours. After completion of the reaction, the solvent was evaporated. The resulting residue was applied to a silica gel column chromatography to yield 1.31 g (53%) of the title compound as an oily substance from the eluate of n-hexane:ethyl acetate=5:1.

$^1$H-NMR (400 MHz, CDCl$_3$) δ: 1.48–1.11 (4H, m), 1.21–1.35 (1H, m), 1.39 and 1.47 (9H, each s), 1.79–1.89 (1H, m), 2.24–2.69 (1H, m), 2.83–3.69 (8H, m), 4.47 (2H, s), 5.12 (2H, s), 7.29–7.36 (5H, m).

Reference Example E-5

(3R)-1-[1-(N-tert-Butoxycarbonyl-N-(2-hydroxyethyl)amino)cyclopropyl]pyrrolidine A 772 mg (1.56 mmol) portion of (3R)-1-benzyloxycarbonyl-3-[1-(N-2-benzyloxyethyl-N-tert-butoxycarbonyl)aminocyclopropyl]pyrrolidine was dissolved in 20 ml of methanol, mixed with 200 mg of 5% palladium-carbon and then subjected to 36 hours of hydrogenation at 10 kg/cm$^2$ under warming by an infrared lamp. After completion of the reaction, 5% palladium-carbon was removed by filtration and then methanol was evaporated to yield 413 mg (98%) of the title compound. This product was immediately used in the substitution reaction.

Reference Example F-1

Ethyl 1-tert-butoxycarbonylaminocyclobutanecarboxylate

A 1.72 g (10.0 mmol) portion of ethyl hydrogen 1,1-cyclobutanedicarboxylate was dissolved in 20 ml of tert-butanol, mixed with 3.30 g (1.2 mmol) of diphenylphosphoric acid azide and 1.67 ml (1.2 mmol) of triethylamine, and then heated overnight under reflux. After evaporation of the solvent, the resulting residue was purified by a silica gel column chromatography (SiO$_2$ 120 ml, hexane:ethyl acetate=20:1→4:1) to yield 2.11 g (87%) of the title compound.

$^1$H-NMR (CDCl$_3$) δ: 1.28 (3H, t), 1.43 (9H, s), 2.00–2.04 (2H, m), 2.31 (2H, brs), 4.22 (2H, dd).

Reference Example F-2

1-tert-Butoxycarbonylaminocyclobutanecarboxylic acid

A 64.28 g (264 mmol) portion of ethyl 1-tert-butoxycarbonylaminocyclobutanecarboxylate was dissolved in 400 ml of methanol, mixed with 400 ml of 1N sodium hydroxide aqueous solution and then stirred overnight at room temperature. After evaporation of the solvent, the resulting residue was mixed with 20% citric acid aqueous solution-chloroform. The resulting organic layer was dried over anhydrous sodium sulfate and the solvent was evaporated to yield 55.29 g (97%) of the title compound.

$^1$H-NMR (CDCl$_3$) δ: 1.45 (9H, s), 2.02–2.08 (2H, m), 2.26 (2H, brs), 2.67 (2H, brs), 5.20 (1H, brs).

Reference Example F-3

Ethyl 1-tert-butoxycarbonylamino-β-oxocyclobutanepropanoate

To a 100.0 ml portion of ethanol were added 5.0 g (0.21 mmol) of magnesium and 15.0 ml of carbon tetrachloride in that order, followed by 1 hour of stirring at room temperature. Thereto was added dropwise ethyl hydrogen malonate. After 1 hour of stirring at room temperature, the solvent was evaporated to yield magnesium malonate as a colorless foamy substance. Separately, 55.29 g (0.26 mmol) of 1-tert-butoxycarbonylaminocyclobutanecarboxylic acid was dissolved in 450.0 ml of THF, mixed with 45.81 g (0.28 mmol) of 1,1'-carbonyldiimidazole and then stirred at room temperature for 1.5 hours. To this was added dropwise 450.0 ml of THF solution of the above magnesium salt in 30 minutes, followed by 2 days of stirring at room temperature. After evaporation of the solvent, the resulting residue was distributed between 10% citric acid aqueous solution and ethyl acetate. The resulting organic layer was washed with saturated sodium bicarbonate aqueous solution and saturated brine and then dried over anhydrous sodium sulfate. By evaporating the solvent, the title compound was obtained quantitatively.

$^1$H-NMR (CDCl$_3$) δ: 1.26–1.30 (2H, m), 1.43 (9H, s), 1.87–2.08 (4H, m), 2.66–2.70 (2H, m), 3.54 (2H, s), 4.20 (2H, q), 5.22 (1H, brs).

Reference Example F-4

Ethyl 1-tert-butoxycarbonylamino-β-hydroxycyclobutanepropanoate

A 70.21 g (257 mmol) portion of ethyl 1-tert-butoxycarbonylamino-β-oxocyclobutanepropanoate was dissolved in 500.0 ml of ethanol. Thereto was added 4.86 g (514 mmol) of sodium borohydride in small portions under ice cooling. After 2 hours of stirring at the same temperature, water was added and the solvent was evaporated. The resulting residue was extracted with chloroform, washed with saturated brine and then dried over anhydrous sodium sulfate. By evaporating the solvent, 65.25 g (93%) of the title compound was obtained.

$^1$H-NMR (CDCl$_3$) δ: 1.28 (3H, t), 1.44 (9H, s), 1.84–2.57 (8H, m), 4.17 (2H, q).

Reference Example F-5

Ethyl 1-tert-butoxycarbonylaminocyclobutanepropenoate

A 65.25 g (238 mmol) portion of ethyl 1-tert-butoxycarbonylamino-β-hydroxycyclobutanepropanoate was dissolved in 1,000 ml of methylene chloride and mixed with 66.30 g (476 mmol) of triethylamine. Thereto was added dropwise 23.93 ml (7.04 mmol) of methanesulfonyl chloride with cooling in ice water-brine, followed by 1 hour of stirring at the same temperature. To this solution was added dropwise 78.25 ml (523.6 mmol) of 1,8-diazabicyclo[5,4,0]undec-7-ene, then, raising the temperature gradually, and followed by subsequent 5 hours of stirring at room temperature. This was washed with 10% citric acid aqueous solution and saturated brine, and dried over anhydrous sodium sulfate. By evaporating the solvent, 40.95 g (64%) of the title compound was obtained as a pale yellow oily substance.

$^1$H-NMR (CDCl$_3$) δ: 1.28 (3H, t), 1.43 (9H, s), 1.91–2.05 (2H, m), 2.27 (4H, brs), 4.20 (2H, q), 5.88 (1H, d, J=15.6 Hz), 7.16 (1H, d, J=15.6 Hz).

Reference Example F-6

Ethyl 3-(1-tert-butoxycarbonylaminocyclobutyl)-4-nitrobutanoate

A 40.95 g (152 mmol) portion of ethyl 1-tert-butoxycarbonylaminocyclobutanepropenoate was dissolved in 210.0 ml of nitromethane, mixed with 57.2 ml (456 mol) of diphenylphosphoric acid azide and 1.67 ml (1.2 mmol) of tetramethylguanidine, and then stirred at room temperature for 2 days. After evaporation of the solvent, the resulting residue was purified by a silica gel column chromatography (silica gel 1,500 ml, hexane:ethyl acetate=20:1–3:1) to yield 26.60 g (41%) of the title compound.

$^1$H-NMR (CDCl$_3$) δ: 1.26 (3H, t), 1.43 (9H, s), 1.75–2.22 (6H, m), 2.42 (1H, dd, J=15.6, 7.8 Hz), 2.56 (1H, dd, J=15.6, 4.8 Hz), 4.12 (2H, q), 4.21 (1H, dd, J=14.1, 7.3 Hz), 4.45 (1H, dd, J=13.1, 8.3 Hz), 4.70 (1H, brs).

Reference Example F-7

4-(1-tert-Butoxycarbonylaminocyclobutyl-2-pyrrolidone

A 20.6 g (62.5 mmol) portion of ethyl 3-(1-tert-butoxycarbonylaminocyclobutyl)-4-nitrobutanoate was dissolved in 500.0 ml of ethanol, mixed with 40.0 ml of Raney nickel (R-100, after washing with water and ethanol) and then stirred overnight at room temperature with bubbling of hydrogen gas. After removal of the catalyst by filtration, the solvent was evaporated. The resulting residue was dissolved in 200.0 ml of toluene and heated overnight under reflux. After spontaneous cooling, the solvent was evaporated to yield 15.13 g (95%) of the title compound.

$^1$H-NMR (CDCl$_3$) δ: 1.43 (9H, s), 1.7–2.6 (8H, m), 3.1–3.5 (3H, m), 4.84 (1H, brs), 6.20 (1H, brs).

Reference Example F-8

1-Benzyl-4-(1-tert-butoxycarbonylaminocyclobutyl)-2-pyrrolidone

A 15.13 g (59.5 mmol) portion of 4-(1-tert-butoxycarbonylaminocyclobutyl)-2-pyrrolidone was dissolved in 30.0 ml of N,N-dimethylformamide, cooled in an ice bath, mixed with 2.62 g (65.44 mmol) of sodium hydride (60% oil suspension) and then stirred at room temperature for 30 minutes. This was mixed with 7.78 ml (65.44 mmol) of benzyl bromide and stirred overnight at room temperature. Since the starting material partially remained, 1.19 g (29.74 mmol) of sodium hydride and 3.54 ml (29.74 mmol) of benzyl bromide were further added and stirred for additional 5 hours at room temperature. After evaporation of the solvent, the resulting residue was mixed with water, extracted with ethyl acetate and washed with saturated brine. After drying over anhydrous sodium sulfate, the solvent was evaporated. Thereafter, the resulting residue was purified by a silica gel column chromatography (silica gel 800 ml, ethyl acetate:hexane=10:1→1:1→2:1) to yield 5.65 g (28%) of the title compound.

$^1$H-NMR (CDCl$_3$) δ: 1.41 (9H, s), 1.69–1.71 (1H, m), 1.95–2.19 (5H, m), 2.36 (1H, dd, J=17.0, 7.8 Hz), 2.52 (1H, dd, J=17.0, 9.2 Hz), 2.95–3.29 (3H, m), 4.43 (2H, AB-q, J=14.6 Hz), 4.77 (1H, brs), 7.22–7.34 (5H, m).

Reference Example F-9

4-(1-Aminocyclobutyl)-1-benzyl-2-pyrrolidone trifluoroacetate

To 5.65 g (16.40 mmol) of 1-benzyl-4-(1-tert-butoxycarbonylaminocyclobutyl)-2-pyrrolidone cooled in an ice bath was added dropwise 50.0 ml of trifluoroacetic acid, followed by 1 hour of stirring at room temperature. Excess reagent was evaporated, and the resulting residue was mixed with toluene and subjected to azeotropic heating to yield the title compound quantitatively as a pale yellow oily substance.

$^1$H-NMR (CDCl$_3$) δ: 1.73–2.35 (6H, m), 2.55 (1H, dd, J=17.5, 7.3 Hz), 2.72 (1H, dd, J=17.5, 9.7 Hz), 2.83–2.92 (1H, m), 3.33 (1H, dd, J=10.7, 6.3 Hz), 3.44–3.49 (1H, m), 4.43 (2H, AB-q, J=14.6 Hz), 7.14–7.35 (5H, m).

Reference Example F-10

1-Benzyl-4-[1-[N'-p-toluenesulfonyl-2-(R)-pyrrolidinecarbonyl]-aminocyclobutyl]-2-pyrrolidone (fr. 1) (fr. 2)

A 5.87 g (16.40 mmol) portion of 4-(1-aminocyclobutyl)-1-benzyl-2-pyrrolidone trifluoroacetate was dissolved in 30.0 ml of methylene chloride (stabilizing agent free) and mixed with 13.26 ml of pyridine. Thereto was added dropwise a solution of 7.07 g (24.6 mol) of D-(R)-N-p-toluenesulfonylpyrophosphoric acid chloride in 30.0 ml of methylene chloride under ice cooling. After overnight stirring at room temperature, the solvent and excess pyridine were evaporated, and the resulting residue was mixed with 1N hydrochloric acid and extracted with chloroform. The extract was washed with saturated sodium bicarbonate aqueous solution and saturated brine, and then dried over anhydrous sodium sulfate. After evaporation of the solvent, the resulting residue was purified by a silica gel column chromatography (silica gel 1 kg, ethyl acetate→ethyl acetate:isopropyl ether=50:1) to yield 3.16 g (39%) of (fr.1) and 3.33 g (41%) of (fr.2).

Low porality substance (fr.1)

$^1$H-NMR (CDCl$_3$) δ: 1.55–2.37 (12H, m), 2.45 (3H, s), 2.57 (1H, dd, J=17.0, 9.2 Hz), 2.90–2.98 (1H, m), 3.10–3.17 (1H, m), 3.25 (1H, t, J=9.7 Hz), 3.36 (1H, dd, J=9.7, 5.8 Hz), 3.51–3.56 (1H, m), 3.85 (1H, dd, J=8.3, 2.9 Hz), 4.41 (2H, AB-q, J=14.6 Hz), 7.22–7.36 (7H, m), 7.72 (2H, d, J=8.3 Hz).

High porality substance (fr.2)

$^1$H-NMR (CDCl$_3$) δ: 1.50–2.44 (12H, m), 2.45 (3H, s), 2.52 (1H, dd, J=17.0, 9.2 Hz), 3.03–3.18 (3H, m), 3.36 (1H, dd, J=9.7, 8.3 Hz), 3.51–3.56 (1H, m), 3.88 (1H, dd, J=8.7, 2.9 Hz), 4.48 (2H, AB-q, J=14.6 Hz), 7.22–7.36 (7H, m), 7.71 (2H, d, J=8.3 Hz).

Reference Example F-11

1-Benzyl-4-(1-aminocyclobutyl)-2-pyrrolidone (fr. 1)

A 2.40 g (4.84 mmol) portion of 1-benzyl-4-[1-[N'-p-toluenesulfonyl-2-(R)-pyrrolidinecarbonyl] aminocyclobutyl]-2-pyrrolidone (fr. 1) was mixed with 15 ml of water and 15 ml of concentrated hydrochloric acid, and then heated under reflux for 2 days. After cooling, the reaction solution was mixed with 100 ml of water, washed with chloroform and then made alkaline with sodium hydroxide aqueous solution. This was extracted with chloroform (150 ml×4), washed with saturated brine and dried over anhydrous sodium sulfate. By evaporating the solvent, 1.01 g (85%) of the title compound was obtained.

$^1$H-NMR (CDCl$_3$) δ: 1.44 (2H, brs), 1.58–1.99 (6H, m), 2.30–2.38 (1H, m), 2.49–2.56 (2H, m), 3.03–3.07 (1H, m), 3.28–3.32 (1H, m), 4.45 (2H, AB-q, J=14.6 Hz), 7.22–7.35 (5H, m).

Reference Example F-12

1-Benzyl-4-(1-aminocyclobutyl)-2-pyrrolidone (fr. 2)

A 2.84 g (5.73 mmol) portion of 1-benzyl-4-[1-[N'-p-toluenesulfonyl-2-(R)-pyrrolidinecarbonyl] aminocyclobutyl]-2-pyrrolidone (fr. 2) was mixed with 20 ml of water and 20 ml of concentrated hydrochloric acid, and then heated under reflux for 2 days. After cooling, the reaction solution was mixed with 100 ml of water, washed with chloroform and then made alkaline with sodium hydroxide aqueous solution. This was extracted with chloroform (150 ml×4), washed with saturated brine and dried over anhydrous sodium sulfate. By evaporating the solvent, the title compound was obtained quantitatively.

$^1$H-NMR (CDCl$_3$) δ: 1.25 (2H, brs), 1.59–1.99 (6H, m), 2.30–2.37 (1H, m), 2.48–2.58 (2H, m), 3.03–3.07 (1H, m), 3.26–3.32 (1H, m), 4.45 (2H, AB-q, J=14.6 Hz), 7.22–7.35 (5H, m, Ar-H).

Reference Example F-13

1-Benzyl-3-(1-tert-butoxycarbonylaminocyclobutyl) pyrrolidine (fr. 1)

A 1.01 g (4.13 mmol) portion of 1-benzyl-4-(1-aminocyclobutyl)-2-pyrrolidone (fr. 1) was dissolved in 150.0 ml of tetrahydrofuran. Thereto was subsequently added 627 mg (16.52 mmol) of lithium aluminum hydride in small portions under ice cooling. After 12 hours of stirring with heating under reflux, the reaction solution was cooled in an ice bath and mixed with 627 µl of water in small portions, 627 µl of 15% sodium hydroxide aqueous solution and 627 µl of water in that order. After 30 minutes of stirring at room temperature, insoluble material was removed by filtration and the solvent was evaporated. To the thus obtained syrup were added 50.0 ml of acetonitrile and then 1.14 ml (4.96 mmol) of di-tert-butylcarbonate at room temperature, followed by overnight stirring. After evaporation of the solvent, the resulting residue was purified by a silica gel column chromatography (230–400 mesh silica gel 100 ml, 5% methanol-chloroform) to yield 212 mg (16%) of the title compound.

$^1$H-NMR (CDCl$_3$) δ: 1.45–1.98 (15H, m), 2.06–2.20 (2H, m), 2.47–2.52 (1H, m), 2.75–3.01 (4H, m), 3.57 (2H, s), 5.15 (1H, brs), 7.22–7.37 (5H, m).

Reference Example F-14

1-Benzyl-3-(1-tert-butoxycarbonylaminocyclobutyl) pyrrolidine (fr. 2)

A 1.50 g (6.14 mmol) portion of 1-benzyl-4-(1-aminocyclobutyl)-2-pyrrolidone (fr. 2) was dissolved in 200.0 ml of tetrahydrofuran to which, with cooling in an ice bath, was subsequently added 932 mg (24.56 mmol) of lithium aluminum hydride in small portions. After 12 hours of stirring with heating under reflux, the reaction solution was cooled in an ice bath and mixed with 932 µl of water in small portions, 932 µl of 15% sodium hydroxide aqueous solution and 932 µl of water in that order. After 30 minutes of stirring at room temperature, insoluble material was removed by filtration and the solvent was evaporated. To the thus obtained syrup were added 70.0 ml of acetonitrile and then 1.69 ml (7.37 mmol) of di-tert-butylcarbonate at room temperature, followed by overnight stirring. After evaporation of the solvent, the resulting residue was purified by a silica gel column chromatography (230–400 mesh silica gel 150 ml, 5% methanol-chloroform) to yield 525 mg (26%) of the title compound.

$^1$H-NMR (CDCl$_3$) δ: 1.45–1.96 (15H, m), 2.06–2.20 (2H, m), 2.47–2.52 (1H, m), 2.75–3.01 (4H, m), 3.57 (2H, s), 4.21 (1H, brs), 7.25–7.37 (5H, m).

Reference Example F-15

3-(1-tert-Butoxycarbonylaminocyclobutyl) pyrrolidine (fr. 1)

A 212 mg (0.65 mmol) portion of 1-benzyl-3-(1-tert-butoxycarbonylaminocyclobutyl)pyrrolidine (fr. 1) was dissolved in 20.0 ml of ethanol, mixed with 200 mg of 10% palladium-carbon and stirred for 3 hours under a hydrogen pressure of 4 atm with warming by an infrared lamp. After removing the catalyst by filtration, the solvent was evaporated to yield 136 mg (88%) of the title compound.

Reference Example F-16

3-(1-tert-Butoxycarbonylaminocyclobutyl) pyrrolidine (fr. 2)

A 525 mg (1.59 mmol) portion of 1-benzyl-3-(1-tert-butoxycarbonylaminocyclobutyl)pyrrolidine (fr. 2) was dissolved in 50.0 ml of ethanol, mixed with 500 mg of 10% palladium-carbon and stirred for 3 hours under a hydrogen pressure of 4 atm with warming by an infrared lamp. After removing the catalyst by filtration, the solvent was evaporated to yield quantitative amount of the title compound.

Reference Example G-1

1-Benzhydryl-3-(p-toluenesulfonyloxy)azetidine

To 2.39 g (10 mmol) of 1-benzhydryl-3-hydroxyazetidine dissolved in 20 ml of pyridine were added 1.46 g (12 mmol) of dimethylaminopyridine. Thereto was added 12.10 g (11 mmol) of p-toluenesulfonyl chloride at −40° C., followed by gradual increase in the temperature and subsequent 1 day of stirring at room temperature. This was mixed with 150 ml of water, extracted with chloroform (100 ml×3) and then dried over anhydrous sodium sulfate. After evaporation of the solvent, the resulting residue was purified by a silica gel column chromatography (250 ml, ethyl acetate:hexane 1:2) to yield 2.88 g (73%) of the title compound.

$^1$H-NMR (CDCl$_3$) δ: 2.42 (3H, s), 3.02–3.06 (2H, m), 3.43–3.47 (2H, m), 4.32 (1H, s), 4.86–4.89 (1H, m), 7.15–7.76 (14H, m).

Reference Example G-2

Diethyl (1-benzhydryl-3-azetidinyl)malonate

To 17.90 g (111.80 mmol) of diethyl malonate dissolved in 250 ml of tetrahydrofuran was added 4.07 g (101.75 mmol) of 60% sodium hydride at room temperature, followed by 2 hours of stirring. Thereafter, thereto was added 20 g (50.82 mmol) of 1-benzhydryl-3-(p-toluenesulfonyloxy)azetidine which has been dissolved in 90 ml of tetrahydrofuran, followed by 1 week of heating under reflux. The reaction solution was mixed with 10% citric acid aqueous solution and then tetrahydrofuran was evaporated. The resulting residue was mixed with saturated sodium bicarbonate aqueous solution, extracted with chloroform (200 ml×3) and dried over anhydrous sodium sulfate. After evaporation of the solvent, the resulting residue was purified by a silica gel column chromatography (230–400 mesh silica gel 450 ml, ethyl acetate:hexane 1:3) to yield quantitative amount of the title compound.

$^1$H-NMR (CDCl$_3$) δ: 1.21 (6H, t, J=7.3 Hz), 2.89–2.92 (2H, m), 2.97–3.05 (1H, m), 3.35–3.39 (2H, m), 3.64 (1H, d, J=10.2 Hz), 4.14 (4H, dd), 4.32 (1H, s), 7.14–7.38 (10H, m).

Reference Example G-3

Diethyl (1-benzyloxycarbonyl-3-azetidinyl)malonate

To 3.40 g (8.91 mmol) of diethyl (1-benzhydryl-3-azetidinyl)malonate dissolved in 30 ml of dichloromethane was added 1.91 ml (13.36 mmol) of benzyl chloroformate, followed by overnight stirring at room temperature. After evaporation of the solvent, the resulting residue was purified by a silica gel column chromatography (250 ml, 3–5% methanol-dichloromethane) to yield 2.64 g (84%) of the title compound.

$^1$H-NMR (CDCl$_3$) δ: 1.25 (6H, t), 3.16–3.19 (1H, m), 3.62 (1H, d, J=11.7 Hz), 3.79–3.83 (2H, m), 4.16–4.22 (4H, m), 5.08 (2H, s), 7.31–7.35 (5H, m).

Reference Example G-4

Ethyl hydrogen (1-benzyloxycarbonyl-3-azetidinyl) malonate

To 13.43 g (38.33 mmol) of diethyl (1-benzyloxycarbonyl-3-azetidinyl)malonate dissolved in 130 ml of ethanol was added 38.44 ml of 1N potassium hydroxide ethanol solution, followed by overnight stirring at room temperature. After evaporation of the solvent, the resulting residue was mixed with 10% citric acid aqueous solution, extracted with chloroform (200 ml×3) and then dried over anhydrous sodium sulfate. By evaporating the solvent, quantitative amount of the title compound was obtained.

$^1$H-NMR (CDCl$_3$) δ: 1.27 (3H, t), 3.17–3.22 (1H, m), 3.66 (1H, d, J=10.7 Hz), 3.83 (2H, dd, J=5.8, 8.7 Hz), 4.17–4.24 (4H, m), 5.09 (2H, s), 7.33–7.34 (5H, m).

Reference Example G-5

Ethyl 2-(1-benzyloxycarbonyl-3-azetidinyl)acrylate

To 732 mg (2.28 mmol) of ethyl hydrogen (1-benzyloxycarbonyl-3-azetidinyl)malonate dissolved in 70 ml of acetonitrile were added 1.05 g (5.67 mmol) of Eshenmoser's salt and a catalytically effective amount of potassium acetate, followed by 4.5 hours of heating under reflux. After evaporation of the solvent, the resulting residue was mixed with 100 ml of ethyl acetate, washed with 10% citric acid aqueous solution, 10% sodium sulfite aqueous solution and saturated brine in that order, and then dried over anhydrous sodium sulfate. By evaporating the solvent, 569 mg (86%) of the title compound was obtained.

$^1$H-NMR (CDCl$_3$) δ: 1.29 (3H, t), 3.60–3.64 (1H, m), 3.91–3.95 (2H, m), 4.18–4.25 (4H, m), 5.09 (2H, s), 5.66 (1H, d, J=1.9 Hz), 6.36 (1H, d, J=1.4 Hz), 7.29–7.36 (5H, m).

Reference Example G-6

Ethyl 1-(1-benzyloxycarbonyl-3-azetidinyl) cyclopropanecarboxylate

To 1.27 g (5.76 mmol) of trimethylsulfoxonium iodide dissolved in 10 ml of dimethyl sulfoxide was added 192 mg (4.80 mmol) of 60% sodium hydride, followed by 15 minutes of stirring at room temperature. Thereto was then added 1.39 g (4.80 mmol) of ethyl 2-(1-benzyloxycarbonyl-3-azetidinyl)acrylate which has been dissolved in 10 ml of dimethyl sulfoxide. The resulting mixture was stirred at room temperature for 4 hours and then at 100° C. for 1 hour. The reaction solution was mixed with 200 ml of saturated brine and extracted with ethyl acetate (100 ml×3), and the organic layer was washed with saturated brine (100 ml×2) and dried over anhydrous sodium sulfate. After evaporation of the solvent, the resulting residue was purified by a silica gel column chromatography (100 ml, ethyl acetate:hexane= 1:2) to yield 536 mg (37%) of the title compound.

$^1$H-NMR (CDCl$_3$) δ: 0.84 (2H, s), 1.20–1.25 (5H, m), 3.26–3.28 (1H, m), 3.54 (2H, brs), 4.05–4.13 (4H, m), 5.08 (2H, s), 7.32–7.35 (5H, m).

Reference Example G-7

1-(1-Benzyloxycarbonyl-3-azetidinyl)cyclopropanecarboxylic acid

To 2.68 g (8.83 mmol) of ethyl 1-(1-benzyloxycarbonyl-3-azetidinyl)cyclopropanecarboxylate dissolved in 27 ml of ethanol was added 27 ml of 1N sodium hydroxide aqueous solution, followed by overnight stirring at room temperature. After evaporation of the solvent, the resulting residue was mixed with 10% citric acid aqueous solution, extracted with chloroform (50 ml×3) and then dried over anhydrous sodium sulfate. By evaporating the solvent, 2.35 g (97%) of the title compound was obtained.

$^1$H-NMR (CDCl$_3$) δ: 0.93 (2H, s), 1.31 (2H, d, J=2.4 Hz), 3.24–3.28 (1H, m), 3.54 (2H, brs), 4.06 (2H, brs), 5.08 (2H, s), 7.30–7.37 (5H, m).

Reference Example G-8

1-Benzyloxycarbonyl-3-(1-tert-butoxycarbonylaminocyclopropyl)azetidine

A 2.35 g (8.54 mmol) portion of 1-(1-benzyloxycarbonyl-3-azetidinyl)cyclopropanecarboxylic acid was dissolved in 40 ml of tert-butanol and mixed with 3.52 g (12.7 mmol) of diphenylphosphoric acid azide and 2.38 ml (17.07 mmol) of triethylamine, and the mixture was then heated overnight under reflux. After evaporation of the solvent, the resulting residue was purified by a silica gel column chromatography (silica gel 600 ml, hexane:ethyl acetate 2:3) to yield 1.84 g (62%) of the title compound.

$^1$H-NMR (CDCl$_3$) δ: 0.75 (2H, S), 0.83 (2H, s), 1.41 (9H, s), 2.82–2.89 (1H, m), 3.71 (2H, brs), 4.22 (2H, t, J=8.7 Hz), 5.06 (1H, brs), 5.08 (2H, s), 7.28–7.34 (5H, m).

Reference Example G-9

3-(1-tert-Butoxycarbonylaminocyclopropyl)azetidine

To 1.84 g (5.31 mmol) of 1-benzyloxycarbonyl-3-(1-tert-butoxycarbonylaminocyclopropyl)azetidine dissolved in 100 ml of ethanol was added 1.5 g of 10% palladium-carbon, followed by overnight catalytic hydrogenation at room temperature under normal pressure. After removal of the catalyst by filtration, the solvent was evaporated to yield quantitative amount of the title compound.

$^1$H-NMR (CDCl$_3$) δ: 0.79 (2H, brs), 0.87 (2H, s), 1.44 (9H, s), 1.78 (1H, brs), 3.00 (1H, brs), 4.01 (4H, d, J=7.8 Hz), 5.29 (1H, brs).

Reference Example H-1

Dimethyl 3,4,5,6-tetrafluorophthalate

To 300 g (1.26 mol) of 3,4,5,6-tetrafluorophthalic acid dissolved in methanol and cooled in an ice bath was added 300 ml of sulfuric acid, followed by 3 days of reflux. After cooling to room temperature, the precipitated crystals were collected by filtration. After evaporating methanol from the filtrate, the resulting residue was mixed with 2 liters of ice water to collect precipitated crystals. The combined crystals were washed with water and then dried to yield 294.86 g of the title compound as a partially purified product.

$^1$H-NMR (400 MHz, CDCl$_3$) δ: 0.95 (6H, s).

Reference Example H-2

Dimethyl 4-diethoxycarbonylmethyl-3,5,6-trifluorophthalate

To 286.4 g (1.077 mol) of dimethyl 3,4,5,6-tetrafluorophthalate dissolved in 750 ml of dimethylformamide were added 164 ml (1.08 mol) of diethyl malonate and 414.63 g (3 mol) of potassium carbonate, followed by 26 hours of stirring at room temperature. The reaction mixture was filtered, and the filtrate was poured into 1,200 ml of 4N hydrochloric acid and extracted with ether (1 liter×2). The resulting organic layer was washed with water (1 liter×2) and saturated brine (1 liter) and then dried over anhydrous sodium sulfate. By evaporating the solvent, 433.61 g (1.068 mol, 99.2%) of the title compound was obtained as a partially purified product.

$^1$H-NMR (400 MHz, CDCl$_3$) δ: 1.29 (6H, t, J=7.5 Hz), 3.92 (3H, s), 3.96 (3H, s), 4.28 (4H, q, J=7.5 Hz), 4.98 (1H, s).

Reference Example H-3

4-Carboxymethyl-3,5,6-trifluorophthalic acid

Two liters of 60% sulfuric acid was added to 433.6 g (1.068 mol) of dimethyl 4-diethoxycarbonylmethyl-3,5,6-trifluorophthalate, followed by stirring for 40 hours at 110° C.. After cooling to room temperature, this was poured into 1 liter of water and extracted with ethyl acetate (1 liter×3). The organic layer was washed with 1 liter of water and 1 liter of saturated brine, and then dried over sodium sulfate. By evaporating the solvent, 304.35 g of the title compound was obtained as a partially purified product.

$^1$H-NMR (400 MHz, D$_2$O) δ: 3.77 (2H, s).

Reference Example H-4

2,4,5-Trifluoro-3-methylbenzoic acid

To 304.35 g of 4-carboxymethyl-3,5,6-trifluorophthalic acid dissolved in 1.5 liters of dimethyl sulfoxide was added 0.5 liter of triethylamine, followed by 64 hours of stirring at 140° C. After cooling to room temperature, dimethyl sulfoxide was evaporated. The resulting residue was mixed with 1 liter of 1N hydrochloric acid and extracted with ether (1 liter×3). The organic layer was washed with 1 liter of water and 1 liter of saturated brine, and then dried over sodium sulfate. By evaporating the solvent, 177.94 g (0.64 mol, 60%) of the title compound was obtained as a partially purified product.

$^1$H-NMR (400 MHz, CDCl$_3$) δ: 2.29 (3H, t, J=1.5 Hz), 7.70 (1H, dt, J=6.5, 9.5 Hz).

Reference Example H-5

2,4,5-Trifluoro-3-methyl-6-nitrobenzoic acid

A 43.4 g (0.21 mol) portion of 2,4,5-trifluoro-3-methylbenzoic acid was added to 120 ml of concentrated sulfuric acid under ice cooling. Thereto was added dropwise fuming nitric acid (d 1.52) in such a manner that the reaction temperature did not exceed 30° C. After completion of the dropwise addition, this was stirred for 1 hour at room temperature. After completion of the reaction, the reaction solution was poured into 1.5 liters of ice water to collect the formed crystals by filtration. The thus obtained crystals were washed with water (100 ml×3) and dissolved in 500 ml of ethyl acetate, and the solution was dried over anhydrous sodium sulfate. The filtrate obtained above was extracted with chloroform (300 ml×4) and dried over anhydrous sodium sulfate. Thereafter, the organic layers were combined and concentrated to yield 50.3 g (quantitative) of the title compound.

$^1$H-NMR (400 MHz, CDCl$_3$) δ: 2.36 (3H, t, J=2.44 Hz).

Reference Example H-6

Ethyl 2,4,5-trifluoro-3-methyl-6-nitrobenzoylacetate 2,4,5-Trifluoro-3-methyl-6-nitrobenzoic acid was suspended in 490 ml of benzene to which was subsequently added dropwise 30.4 ml (0.42 mol) of thionyl chloride at room temperature. After completion of the dropwise addition, the reaction solution was heated under reflux for 22 hours. After evaporation of benzene, the resulting residue was subjected twice to azeotropic treatment with 200 ml of benzene to yield crude 2,4,5-trifluoro-3-methyl-6-nitrobenzoyl chloride. A 6.13 g (0.25 mol) portion of magnesium was mixed with 200 ml of ethanol. Thereto was added dropwise 10 ml of carbon tetrachloride at room temperature, followed by 6 hours of stirring at the same temperature. When magnesium was dissolved, 44 ml (0.29 mol) of diethyl malonate dissolved in 150 ml of tetrahydrofuran was added dropwise thereto, spending 1 hour. After completion of the dropwise addition, the mixture was stirred for 2 hours at room temperature. After completion of the reaction, the solvent was evaporated and the resulting residue was dried under a reduced pressure. The thus obtained solid matter was mixed with 300 ml of tetrahydrofuran to which was subsequently added dropwise 150 ml of tetrahydrofuran solution of the acid chloride obtained above in 1.5 hours. After completion of the dropwise addition, the reaction solution was stirred for 2 hours at room temperature. After completion of the reaction, the reaction solution was mixed with 400 ml of ethyl acetate and washed with 10% citric acid (500 ml×1), water (500 ml×1) and saturated brine (500 ml×1) in that order. The organic layer was dried over anhydrous sodium sulfate and the solvent was evaporated. The resulting residue was mixed with 1.5 liters of water and 1.5 g of p-toluenesulfonic acid, and heated under reflux for 1.5 hours. After completion of the reaction, the reaction solution was spontaneously cooled and extracted with benzene (500 ml×5). The organic layers were combined, washed with 500 ml of saturated brine and dried over anhydrous sodium sulfate. After evaporation of the solvent, the resulting residue was subjected to a silica gel column chromatography to yield 37.65 g (44%) of the title compound from the eluate of hexane:ethyl acetate=95:5.

$^1$H-NMR (400 MHz, CDCl$_3$) δ: 1.26 and 1.34 (3H, each t, J=7.33 Hz), 2.33 and 2.35 (3H, each t, J=2.44 Hz), 3.90 (1.35H, s), 4.20 and 4.28 (2H, each q, J=7.33 Hz), 5.48 (0.325H, s), 12.34 (0.325H, s).

Reference Example H-7

Ethyl 6,7-difluoro-1-[(1R,2S)-2-fluorocyclopropyl] 1,4-dihydro-8-methyl-5-nitro-4-oxoquinoline-3-carboxylate To 16.4 g (53.8 mmol) of ethyl 2,4,5-trifluoro-3-methyl-6-nitrobenzoylacetate were added 17.9 ml (107.6 mmol) of ethyl orthoformate and 29 ml of acetic anhydride, followed by 2 hours of stirring at 100° C. The solvent was evaporated, and the resulting residue was dissolved in 200 ml of toluene and mixed with 16 g (64.7 mmol) of p-toluenesulfonic acid salt of (1R,2S)-2-fluorocyclopropylamine. With cooling in an ice bath, thereto was added dropwise 10.87 ml (78 mmol) of triethylamine dissolved in 30 ml of toluene. After completion of the dropwise addition, this was stirred for 2 hours at the same temperature. The reaction solution was mixed with 200 ml of ethyl acetate and washed with water (500 ml×1) and saturated brine (500 ml×2) in that order. The organic layer was dried over anhydrous sodium sulfate and the solvent was evaporated. The resulting residue was dissolved in 150 ml of 1,4-dioxane. Thereto was subsequently added 3.23 g (80.7 mmol) of sodium hydride in small portions under ice cooling. After 1 hour of stirring at room temperature, the reaction solution was poured into 0.5N hydrochloric acid which was cooled in an ice bath. The thus formed crystals were collected by filtration, washed with water (100 ml×3) and then recrystallized from chloroform-ethanol to yield 13.9 g (70%) of the title compound.

Melting point: 230°–231° C.

$^1$H-NMR (400 MHz, CDCl$_3$) δ: 1.38 (3H, t, J=7.33 Hz), 1.35–1.45 (1H, m), 1.58–1.70 (1H, m), 2.75 (3H, d, J=3.42 Hz), 3.85–3.93 (1H, m), 4.37 (2H, q, J=7.33 Hz), 4,80–4.83 and 4.95–4.99 (1H, m), 8.57 (1H, d, J=2.93 Hz).

Reference Example H-8

Ethyl 5-amino-6,7-difluoro-[(1R,2S)-2-fluorocyclopropyl]-1,4-dihydro-8-methyl-4-oxoquinoline-3-carboxylate A 3.91 g (37.6 mmol) portion of ethyl 6,7-difluoro-1-[(1R,2S)-2-fluorocyclopropyl]-1,4-dihydro-8-methyl-5-nitro-4-oxoquinoline-3-carboxylate was suspended in 1 liter of a 1:1 mixture of methanol and 1,4-dioxane. This was mixed with 200 ml of Raney nickel and stirred for 10 minutes at room temperature. After completion of the reaction, the reaction solution was filtered and the resulting filtrate was concentrated. The resulting residue was dissolved in 300 ml of chloroform and filtered through celite. By concentrating the filtrate, 12.5 g (98%) of the title compound was obtained.

$^1$H-NMR (400 MHz, CDCl$_3$) δ: 1.25–1.38 (1H, m), 1.39 (3H, t, J=7.33 Hz), 1.45–1.59 (1H, m), 2.46 (3H, d, J=2.44 Hz), 3.73–3.79 (1H, m), 4.38 (2H, q, J=7.33 Hz), 4.73–4.75 and 4.88–4.92 (1H, m), 6.99 (2H, br s), 8.40 (1H, d, J=3.42 Hz).

Elementary analysis for $C_{16}H_{13}F_3N_2O_5 \cdot 1/4H_2O$: Calcd.: C 51.28 H 3.63 N 7.47 Found: C 51.51 H 3.58 N 7.43

Reference Example H-9

5-Amino-6,7-difluoro-[(1R,2S)-2-fluorocyclopropyl]-1,4-dihydro-8-methyl-4-oxoquinoline-3-carboxylic acid A 10.43 g (30.6 mmol) portion of ethyl 5-amino-6,7-difluoro-[(1R,2S)-2-fluorocyclopropyl]-1,4-dihydro-8-methyl-4-oxoquinoline-3-carboxylate was mixed with 150 ml of acetic acid and 150 ml of concentrated hydrochloric acid and then heated under reflux for 1 hour. After completion of the reaction, the reaction solution was spontaneously cooled and mixed with 700 ml of water. The thus formed crystals were collected by filtration, washed with water (100 ml×2), ethanol (300 ml×1) and ether (300 ml×1) in that order and then dried to yield 7.52 g (79%) of the title compound.

Melting point: 293°–297° C. (decomposition).

$^1$H-NMR (400 MHz, 0.1N NaOD) δ:

1.31–1.42 (1H, m), 1.53–1.68 (1H, m), 2.52 (3H, s), 4.03–4.10 (1H, m), 4.85–4.93 and 5.05–5.10 (1H, m), 8.32 (1H, s).

Reference Example I-1

Ethyl 2,3,4,5,6-pentafluorobenzoylacetate

A mixture consisting of 100 g (0.47 mol) of pentafluorobenzoic acid, 900 ml of benzene and 350 ml (4.80 mol) of thionyl chloride was heated under reflux for 40 hours. After completion of the reaction, the reaction solution was concentrated under a reduced pressure. After repetition of evaporation with benzene (900 ml×2), the resulting residue was dissolved in 500 ml of ether. A mixture consisting of 11.5 g (0.47 mol) of magnesium, 450 ml of ethanol and 20 ml of carbon tetrachloride was stirred at room temperature for 1 hour, and 71.6 ml (0.47 mol) of diethyl malonate dissolved in 900 ml of ether was added dropwise thereto. After 17 hours of stirring at the same temperature, the reaction solution was evaporated to dryness under a reduced pressure, and the residue was dissolved in 1,500 ml of ether. To this was added dropwise the above acid chloride at room temperature, followed by 63 hours of stirring at the same temperature. After completion of the reaction, the reaction solution was washed with 10% citric acid and water in that order, and then dried over anhydrous sodium sulfate, subsequently evaporating the solvent. The residue was mixed with 300 ml of water and 1.00 g (5.81 mol) of p-toluenesulfonic acid, heated under reflux for 6 hours, mixed with 2,500 ml of benzene and then washed with water. The organic layer was dried over anhydrous sodium sulfate and the solvent was evaporated. The resulting residue was purified by distillation under a reduced pressure (10 mmHg, 118°–120° C.) to yield 89.7 g (67%) of the title compound.

Reference Example I-2

Ethyl 5,6,7,8-tetrafluoro-1-[(1R,2S)-2-fluorocyclopropyl]-1,4-dihydro-4-oxoquinoline-3-carboxylate A 14.4 g (51.0 mmol) portion of ethyl 2,3,4,5,6-pentafluorobenzoylacetate was dissolved in 150 ml of benzene, mixed with 28.8 ml (204 mmol) of N,N-dimethylformamide dimethylacetal and then heated under reflux for 3 hours. After completion of the reaction, the solvent was evaporated. The resulting residue was mixed with 120 ml of toluene and 12.6 g (51.0 mmol) of (1R,2S)-2-fluoropropylamine p-toluenesulfonic acid salt and cooled in an ice bath, to which was subsequently added dropwise toluene (39 ml) solution of 8.54 ml (61.2 mmol) triethylamine. After completion of the dropwise addition, this was stirred for 1 hour at room temperature. After completion of the reaction, the reaction solution was filtered by suction, the filtrate was washed with water (50 ml×3) and then the water layer was extracted with ethyl acetate (100 ml×3). The organic layers were combined, washed with saturated brine and then dried over anhydrous sodium sulfate, followed by evaporation of the solvent. The residue was mixed with 100 ml of 1,4-dioxane, cooled in an ice bath and mixed with 2.04 g (51.0 mmol) of 60% sodium hydride, followed by 2 hours of stirring at room temperature. After completion of the reaction, the reaction solution was poured into 10% citric acid and extracted with dichloromethane (200 ml×2). The organic layer was washed with saturated brine and dried over anhydrous sodium sulfate, subsequently evaporating the solvent. The resulting residue was crystallized from dichloromethane-isopropyl ether. The thus obtained crystals were collected by filtration, washed thoroughly with ether and then dried under a reduced pressure to yield 12.6 g (71%) of the title compound.

$^1$H-NMR (400 MHz, CDCl$_3$) δ: 8.46 (1H, s), 5.02–4.80 (1H, m), 4.37 (2H, q, J=7.32 Hz), 3.83–3.75 (1H, m), 1.75–1.55 (2H, m), 1.40 (3H, t, J=7.32 Hz).

Reference Example I-3

Ethyl 5-benzyloxy-6,7,8-trifluoro1-[(1R,2S)-2-fluorocyclopropyl]-1,4-dihydro-4-oxoquinoline-3-carboxylate A 2.35 g (6.77 mmol) portion of ethyl 5,6,7,8-tetrafluoro-1-[(1R,2S)-2-fluorocyclopropyl]-1,4-dihydro-4-oxoquinoline-3-carboxylate was dissolved in 20 ml of toluene and mixed with 0.70 ml (6.77 mmol) of benzyl alcohol. After cooling to 0° C., this was further mixed with 280 mg (6.99 mmol) of 60% sodium hydride which has been suspended in 10 ml of toluene, and the mixture was stirred at the same temperature for 2 hours and then at room temperature for 2 hours. After completion of the reaction, the reaction solution was mixed with 10% citric acid and extracted with chloroform (100 ml×2). The organic layer was dried over anhydrous sodium sulfate and the solvent was evaporated. The resulting residue was purified by a silica gel column chromatography (hexane:ethyl acetate=1:1) to yield 1.68 g (57%) of the title compound.

$^1$H-NMR (400 MHz, CDCl$_3$) δ: 8.41 (1H, s), 7.62–7.28 (5H, m), 5.25 and 5.19 (2H, AB d, J=10.25Hz), 5.00–4.77 (1H, m), 4.39 (2H, q, J=7.33 Hz), 3.82–3.72 (1H, m), 1.70–1.53 (2H, m), 1.39 (3H, t, J=7.33 Hz).

Reference Example I-4

6,7,8-Trifluoro-1-[(1R,2S)-2-fluorocyclopropyl]-1,4-dihydro-5-hydroxy-4-oxoquinoline-3-carboxylate A 1.68 g (3.86 mmol) portion of ethyl 5-benzyloxy-6,7,8-trifluoro-1-[(1R,2S)-2-fluorocyclopropyl]-1,4-dihydro-4-oxoquinoline-3-carboxylate was mixed with 15 ml of a acetic acid-water-sulfuric acid mixture (8:6:1) and heated for 1 hour at 100° C. The reaction solution was cooled to room temperature and mixed with 20 ml of water, and the thus formed crystals were collected by filtration, washed thoroughly with water and then dried under a reduced pressure to yield 1.04 g (85%) of the title compound.

$^1$H-NMR (400 MHz, CDCl$_3$) δ: 13.11 (1H, s), 13.10–12.75 (1H, br), 8.82 (1H, s), 5.09–4.83 (1H, m), 3.99–3.88 (1H, m), 1.86–1.69 (2H, m).

Inventive Example 10

5-Amino-7-[(3R)-3-(1-aminocyclopropyl)-1-pyrrolidinyl]-6,8-difluoro-1-[(1R,2S)-2-fluorocyclopropyl]-1,4-dihydro-4-oxoquinoline-3-carboxylic acid hydrochloride

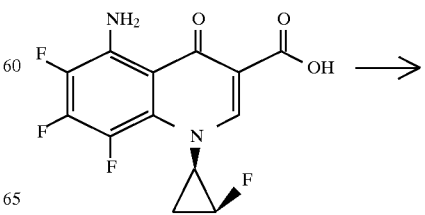

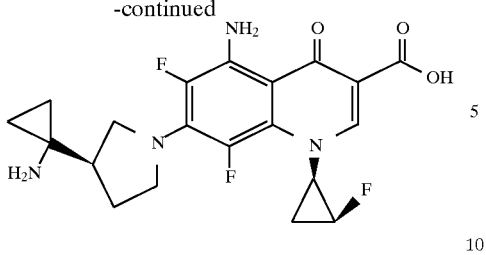

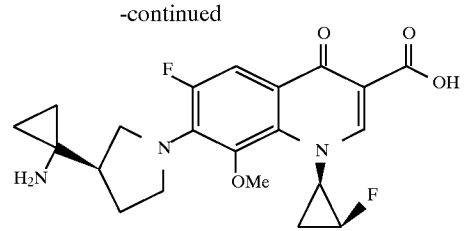

A 278.8 mg (1.25 mmol) portion of 1-benzyloxycarbonyl-3-(1-tert-butoxycarbonylaminocyclopropyl)pyrrolidine was suspended in 10 ml of acetonitrile to which were subsequently added 194.8 mg (0.62 mmol) of 5-amino-6,7,8-trifluoro-[(1R,2S)-2-fluorocyclopropyl]-1,4-dihydro-4-oxoquinoline-3-carboxylic acid and 0.60 ml (4.30 mmol) of triethylamine, followed by 11 hours of heating under reflux. After evaporation of the solvent, the resulting residue was mixed with chloroform, washed with water, 10% citric acid aqueous solution and saturated brine in that order, and then dried over anhydrous sodium sulfate, subsequently evaporating the solvent. The resulting residue was developed twice by a silica gel thin layer chromatography (lower layer of chloroform:methanol:water=7:3:1) to yield a mixture of yellow oil and solid. The thus obtained tert-butylcarbamate compound was cooled in a sodium chloride-ice bath, and 8.0 ml of trifluoroacetic acid was added dropwise thereto. After 20 minutes of stirring at the same temperature, trifluoroacetic acid was evaporated, and the resulting residue was washed three times by decantation after addition of ether. The thus obtained pale yellowish brown powder was dissolved in 1N sodium hydroxide aqueous solution, and the solution was adjusted to pH 7.4 with hydrochloric acid, extracted with chloroform-methanol (10:1) and then dried over anhydrous sodium sulfate, subsequently evaporating the solvent. The resulting residue was mixed with ether, and the thus formed powder was dissolved in ethanol, mixed with hydrochloric acid-diethyl ether and then stirred at room temperature. After evaporation of the solvent, the resulting residue was washed three times by decantation after addition of ether, and the resulting yellow solid was recrystallized from ethanol to yield 55.7 mg (26.2%) of the title compound as yellow powder.

Melting point: 240.0°–260.0° C.

$^{1}$H-NMR (D$_{2}$O) δ: 0.75–0.95 (4H, m), 1.22–1.60 (3H, m), 1.86–2.02 (1H, m), 2.40–2.62 (1H, m), 3.18–3.40 (1H, m), 3.40–3.82 (4H, m), 4.65–4.98 (1H, m), 8.20 (1H, s).

Inventive Example 11

7-[(3R)-3-(1-Aminocyclopropyl)-1-pyrrolidinyl]-6-fluoro-1-[(1R,2S)-2-fluorocyclopropyl]-1,4-dihydro-8-methoxy-4-oxoquinoline-3-carboxylic acid

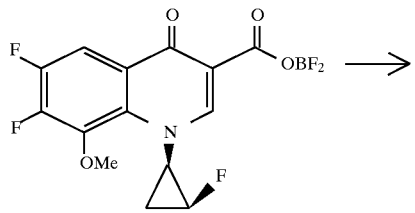

A 433 mg (1.2 mmol) portion of (3R)-1-benzyloxycarbonyl-3-(1-tert-butoxycarbonyl-aminocyclopropyl)pyrrolidine was dissolved in 10 ml of methanol to which was subsequently added 100 mg of 5% palladium-carbon to carry out 2 hours of hydrogenation under normal pressure with warming by an infrared lamp. After completion of the reaction, 5% palladium-carbon was removed by filtration and methanol was evaporated. The resulting residue was dissolved in 10 ml of dimethyl sulfoxide (DMSO) to which were subsequently added 0.174 ml (1.25 mmol) of triethylamine and 217 mg (0.6 mmol) of 6,7-difluoro-[(1R,2S)-2-fluorocyclopropyl]-1,4-dihydro-8-methoxy-4-oxoquinoline-3-carboxylic acid BF$_{2}$ chelate, followed by 25 hours of stirring at room temperature. After completion of the reaction, DMSO was evaporated, the resulting residue was mixed with water, and the thus formed crystals were collected by filtration and washed with water (10 ml×4). The thus obtained crystals were dissolved in 20 ml of methanol and 5 ml of water, and the solution was mixed with 0.3 ml of triethylamine and heated under reflux for 4.5 hours. After completion of the reaction, the reaction solution was mixed with 50 ml of water, methanol was evaporated and then the resulting residue was extracted with chloroform (50 ml×2). The organic layers were combined and dried over sodium sulfate, and the solvent was evaporated. A 10 ml portion of concentrated hydrochloric acid was added dropwise to the resulting residue which was cooled in an ice bath, followed by 10 minutes of stirring at the same temperature. After completion of the reaction, the reaction solution was adjusted to pH 12 with sodium hydroxide aqueous solution and then to pH 7.4 with hydrochloric acid, followed by extraction with chloroform (100 ml×5). The organic layers were combined and dried over anhydrous sodium sulfate, and then the solvent was evaporated. Thereafter, the resulting residue was recrystallized from methanol-2-propanol to yield 181 mg (72%) of the title compound.

Melting point: 195°–197° C.

$[\alpha]_{D}^{25}$=−123.10, (c=0.515, 1N sodium hydroxide aqueous solution)

$^{1}$H-NMR (400 MHz, 0.1N NaOD) δ: 0.60 (4H, s), 1.34–1.60 (2H, m), 1.71–1.82 (1H, m), 1.99–2.07 (1H, m), 2.20–2.29 (1H, m), 3.46–3.65 (2H, m), 3.60 (3H, s), 3.69–3.78 (1H, m), 3.98–4.07 (1H, m), 4.93–4.96 and 5.12–5.15 (1H, m), 7.60 (1H, d, J=13.67 Hz), 8.43 (1H, d, J=2.93 Hz).

Elementary analysis for C$_{21}$H$_{23}$F$_{2}$N$_{3}$O$_{4}$ Calcd.: C 60.14 H 5.53 N 10.02 Found: C 60.02 H 5.45 N 9.92

Inventive Example 12

7-[(3R)-3-(1-Aminocyclopropyl)-1-pyrrolidinyl]-6-fluoro-1-[(1R,2S)-2-fluorocyclopropyl]-1,4-dihydro-8-methyl-4-oxoquinoline-3-carboxylic acid

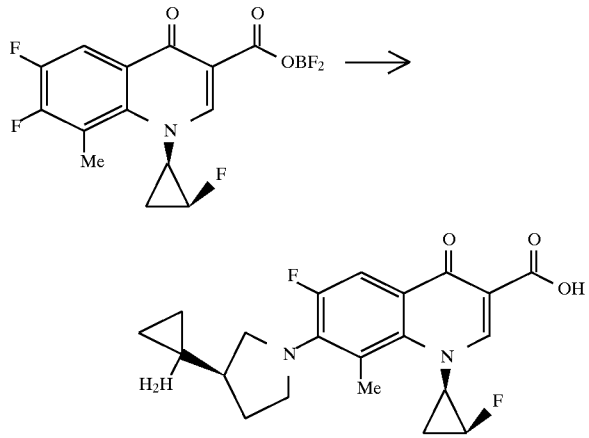

A 322 mg (0.89 mmol) portion of (3R)-1-benzyloxycarbonyl-3-(1-tert-butoxycarbonylamino-cyclopropyl)pyrrolidine was dissolved in 10 ml of methanol to which was subsequently added 100 mg of 5% palladium-carbon to carry out 2 hours of hydrogenation under normal pressure with warming by an infrared lamp. After completion of the reaction, 5% palladium-carbon was removed by filtration and methanol was evaporated. The resulting residue was dissolved in 3 ml of sulfolane to which were subsequently added 0.124 ml (0.89 mmol) of triethylamine and 172 mg (0.5 mmol) of 6,7-difluoro-[(1R,2S)-2-fluorocyclopropyl]-1,4-dihydro-8-methyl-4-oxoquinoline-3-carboxylic acid $BF_2$ chelate, followed by 6 days of stirring at room temperature. After completion of the reaction, the reaction solution was mixed with 100 ml of a solution of ethyl acetate:diethyl ether=1:1, washed with 10% citric acid (100 ml×2) and then dried on sodium sulfate. After evaporation of the solvent, the thus obtained residue was dissolved in a mixture solvent consisting of 50 ml of methanol and 10 ml of water, and the solution was mixed with 1 ml of triethylamine and heated under reflux for 4 hours. After completion of the reaction, methanol was evaporated and the resulting residue was mixed with 100 ml of diethyl ether and washed with 10% citric acid (100 ml×3). The organic layer was dried over magnesium sulfate, and the solvent was evaporated. The resulting residue was subjected to a silica gel thin layer chromatography (methanol:chloroform=1:9), and the resulting silica gel was collected and extracted with a solvent system of methanol:chloroform=1:9. A 10 ml portion of concentrated hydrochloric acid was added dropwise to the thus obtained compound which was cooled in an ice bath, followed by 30 minutes of stirring at the same temperature. After completion of the reaction, the reaction solution was adjusted to pH 12 with sodium hydroxide aqueous solution and then to pH 7.4 with hydrochloric acid, followed by extraction with chloroform (100 ml×4). The organic layers were combined and dried over anhydrous sodium sulfate, and then the solvent was evaporated. Thereafter, the resulting residue was recrystallized from 2-propanol to yield 81 mg (40%) of the title compound.

Melting point: 195°–197° C.

$[\alpha]_D^{25}$=−320.00, (c=0.270, 0.1N sodium hydroxide aqueous solution)

$^1$H-NMR (400 MHz, 0.1N NaOD) δ: 0.58 (4H, s), 1.21–1.38 (1H, m), 1.60–1.82 (2H, m), 2.01–2.07 (1H, m)), 2.22–2.32 (1H, m), 2.53 (3H, s), 3.38–3.43 (2H, m), 3.52–3.59 (1H, m), 3.75–3.83 (1H, m), 4.10–4.14 (1H, m), 4.93–4.96 and 5.09–5.14 (1H, m), 7.71 (1H, d, J=14.16 Hz), 8.45 (1H, d, J=2.44 Hz).

Elementary analysis for $C_{21}H_{23}F_2N_3O_3$ Calcd.: C 62.52 H 5.75 N 10.42 Found: C 62.48 H 5.78 N 10.25

Inventive Example 13

7-[(3R)-3-(1-Aminocyclopropyl)-1-pyrrolidinyl]-6-fluoro-1-[(1R,2S)-2-fluorocyclopropyl]-1,4-dihydro-4-oxoquinoline-3-carboxylic acid

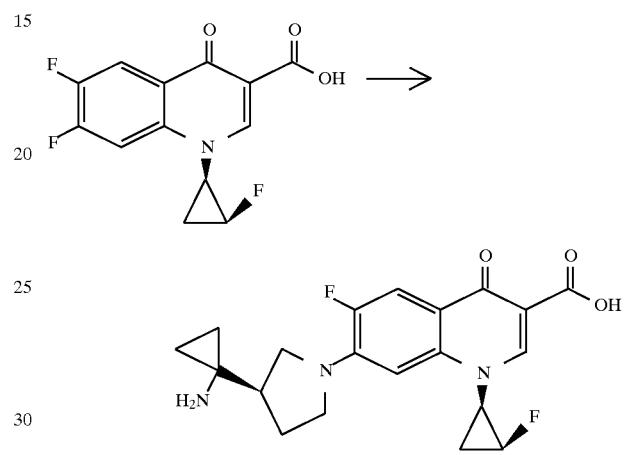

A 322 mg (0.89 mmol) portion of (3R)-1-benzyloxycarbonyl-3-(1-tert-butoxycarbonylamino-cyclopropyl)pyrrolidine was dissolved in 10 ml of methanol to which was subsequently added 100 mg of 5% palladium-carbon to carry out 2 hours of hydrogenation under normal pressure with warming by an infrared lamp. After completion of the reaction, 5% palladium-carbon was removed by filtration and methanol was evaporated. The resulting residue was dissolved in 5 ml of acetonitrile to which were subsequently added 0.5 ml of triethylamine and 113 mg (0.4 mmol) of 6,7-difluoro-[(1R,2S)-2-fluorocyclopropyl]-1,4-dihydro-4-oxoquinoline-3-carboxylic acid, followed by 18 hours of heating under reflux. After completion of the reaction, the reaction solution was spontaneously cooled to collect the thus formed crystals by filtration. With cooling in an ice bath, to the thus obtained crystals was added dropwise 5 ml of concentrated hydrochloric acid, followed by 30 minutes of stirring at the same temperature. After completion of the reaction, the reaction solution was adjusted to pH 12 with sodium hydroxide aqueous solution and then to pH 7.4 with hydrochloric acid, followed by extraction with chloroform (50 ml×3). The organic layers were combined and dried on sodium sulfate, and then the solvent was evaporated. Thereafter, the resulting residue was recrystallized from liquid ammonia-ethanol to yield 120 mg (77%) of the title compound.

Melting point: 240°–242° C.

$[\alpha]_D^{25}$=−32.30, (c=0.260, 0.1N sodium hydroxide aqueous solution)

$^1$H-NMR (400 MHz, 0.1N NaOD) δ: 0.57 (4H, s), 1.68–1.83 (3H, m), 2.01–2.10 (1H, m), 2.19–2.25 (1H, m), 3.29–3.35 (1H, m), 3.48–3.65 (4H, m), 5.12–5.17 and 5.28–5.33 (1H, m), 6.80 (1H, d, J=7.32 Hz), 7.76 (1H, d, J=15.13 Hz), 8.39 (1H, s).

Elementary analysis for $C_{20}H_{21}F_2N_3O_3$ Calcd.: C 61.69 H 5.44 N 10.79 Found: C 60.64 H 5.27 N 10.59

Inventive Example 14

7-[(3R)-3-(1-Aminocyclopropyl)-1-pyrrolidinyl]-6-fluoro-1-[(1R,2S)-2-fluorocyclopropyl]-1,4-dihydro-4-oxo-1,8-naphthyridine-3-carboxylic acid

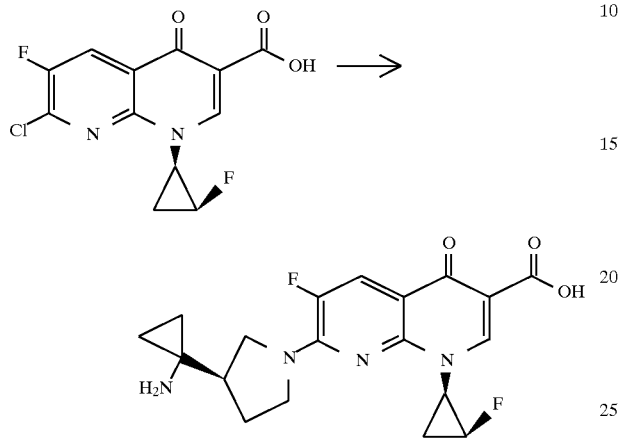

A 180 mg (0.5 mmol) portion of (3R)-1-benzyloxycarbonyl-3-(1-tert-butoxycarbonylamino-cyclopropyl)pyrrolidine was dissolved in 10 ml of methanol to which was subsequently added 100 mg of 5% palladium-carbon to carry out 2 hours of hydrogenation under normal pressure with warming by an infrared lamp. After completion of the reaction, 5% palladium-carbon was removed by filtration and methanol was evaporated. The resulting residue was dissolved in 5 ml of acetonitrile to which were subsequently added 0.5 ml of triethylamine and 144 mg (0.48 mmol) of 7-chloro-6-fluoro-[(1R,2S)-2-fluorocyclopropyl]-1,4-dihydro-4-oxo-1,8-naphthylidine-3-carboxylic acid, followed by 1 hour of heating under reflux and subsequent 18 hours of stirring at room temperature. After completion of the reaction, the reaction solution was spontaneously cooled, and the thus formed crystals were collected by filtration. A 5 ml portion of concentrated hydrochloric acid was added dropwise to the thus obtained crystals under ice cooling, followed by 30 minutes of stirring at the same temperature. After completion of the reaction, the reaction solution was adjusted to pH 12 with sodium hydroxide aqueous solution and then to pH 7.4 with hydrochloric acid, followed by extraction with chloroform (50 ml×3). The organic layers were combined and dried over sodium sulfate, and then the solvent was evaporated. Thereafter, the resulting residue was recrystallized from liquid ammonia-ethanol to yield 79 mg (42%) of the title compound.

Melting point: 232°–234° C.

$[\alpha]_D^{25}$ =58.33, (c=0.120, 0.1N sodium hydroxide aqueous solution)

$^1$H-NMR (400 MHz, 0.1N NaOD) δ: 0.58 (4H, s), 1.60–1.87 (3H, m), 2.05–2.15 (1H, m), 2.20–2.31 (1H, m), 3.48–3.79 (3H, m), 3.95–4.07 (2H, m), 5.02–5.09 and 5.19–5.23 (1H, m), 7.8(1H, d, J=13.19 Hz), 8.37 (1H, s).

Elementary analysis for $C_{19}H_{20}F_2N_4O_3$ Calcd.: C 58.46 H 5.16 N 14.35 Found: C 59.39 H 4.97 N 14.27

Inventive Example 15

7-[3-(1-Aminocyclobutyl)-1-pyrrolidinyl]-6-fluoro-1-[(1R,2S)-2-fluorocyclopropyl]-1,4-dihydro-8-methyl-4-oxoquinoline-3-carboxylic acid (fr. 2)

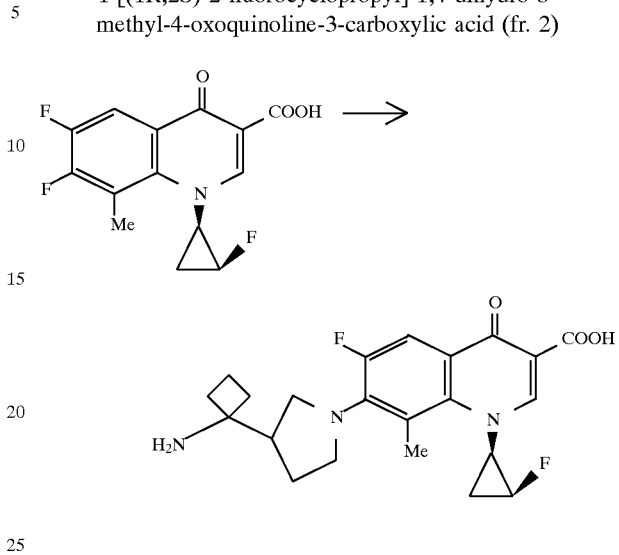

To 446 mg (1.30 mmol) of 6,7-difluoro-[(1R,2S)-2-fluorocyclopropyl]-1,4-dihydro-8-methyl-4-oxoquinoline-3-carboxylic acid $BF_2$ chelate dissolved in 6 ml of sulfolane were added 530 mg (2.20 mmol) of 3-(1-tert-butoxycarbonylaminocyclobutyl)pyrrolidine (fr.2) and 0.54 ml of triethylamine, followed by 12 days of stirring at room temperature. After evaporation of triethylamine, the resulting residue was mixed with 10 ml of water and stirred at room temperature for 30 minutes. The thus formed crystals were washed with water, collected by filtration and then dissolved in 20 ml of a mixed solvent of methanol:water= 9:1, and the solution was mixed with 4 ml of triethylamine and heated under reflux for 3 hours. After evaporation of the solvent, the resulting residue was mixed with 50 ml of chloroform, washed with 10% citric acid (20 ml×2) and dried on magnesium sulfate, and the solvent was then evaporated. A 5 ml portion of concentrated hydrochloric acid was added to the resulting residue and stirred at the room temperature for 2 hours, and then the reaction solution was washed with chloroform (5 ml×2). The reaction solution was adjusted to pH 7.3 with 20% sodium hydroxide aqueous solution and extracted with chloroform (30 ml×3). The organic layers were combined and dried over sodium sulfate, and then the solvent was evaporated. The resulting residue was separated and purified by a preparative TLC (developed by the lower layer of chloroform:methanol:water=7:3:1) and recrystallized from ethanol to yield 220 mg (41%) of the title compound.

Melting point: 140°–143° C.

$^1$H-NMR (400 MHz, 0.1N NaOD) δ: 1.06–1.21 (1H, m), 1.55–1.71 (3H, m), 1.81–1.85 (3H, m), 1.91–2.08 (3H, m), 2.33–2.48 (4H, m, 3.17–3.24 (2H, m), 3.44–3.48 (1H, m), 3.67–3.68 (1H, m), 4.02–4.05 (1H, m), 7.64 (1H, d, J=14.16 Hz), 8.44 (1H, s).

$[\alpha]_D^{23}$ =−318.47, (c=0.184, methanol/chloroform 2/1)

Elementary analysis for $C_{19}H_{19}N_4O_3F_3 \cdot 1/4H_2O$ Calcd.: C 60.68 H 6.25 N 9.65 Found: C 60.41 H 6.20 N 9.58

Inventive Example 16

5-Amino-6,8-difluoro-1-[(1R,2S)-2-fluorocyclopropyl]-1,4-dihydro-7-[(3R)-(1-methylaminocyclopropyl)-1-pyrrolidinyl]-4-oxoquinoline-3-carboxylic acid

Inventive Example 17

6-Fluoro-1-[(1R,2S)-2-fluorocyclopropyl]-1,4-dihydro-8-methoxy-7-[(3R)-3-(1-methylaminocyclopropyl)-1-pyrrolidinyl]-4-oxoquinoline-3-carboxylic acid

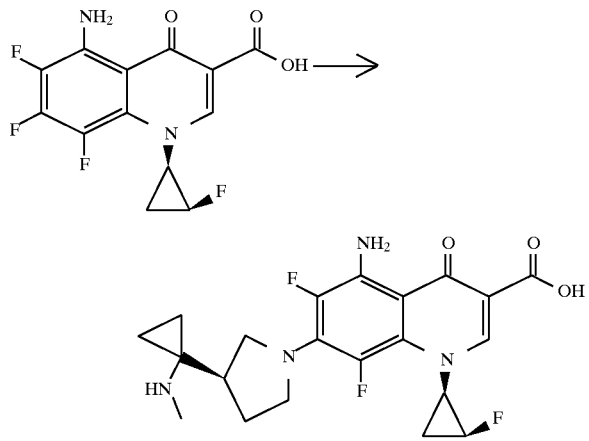

A 310 mg (0.83 mmol) portion of (3R)-1-benzyloxycarbonyl-3-[1-(N-tert-butoxycarbonyl-N-methyl)aminocyclopropyl]pyrrolidine was dissolved in 10 ml of methanol to which was subsequently added 200 mg of 5% palladium-carbon to carry out 1 hour of hydrogenation under normal pressure with warming by an infrared lamp. After completion of the reaction, 5% palladium-carbon was removed by filtration and methanol was evaporated. The resulting residue was dissolved in 10 ml of acetonitrile to which were subsequently added 1.24 ml of 1,8-diazabicyclo[5.4.0]undec-7-ene (DBU) and 190 mg (0.6 mmol) of 5-amino-6,7,8-trifluoro-[(1R,2S)-2-fluorocyclopropyl]-1,4-dihydro-4-oxoquinoline-3-carboxylic acid, followed by 18 hours of heating under reflux. After completion of the reaction, acetonitrile was evaporated and the resulting residue was mixed with 200 ml of chloroform and washed with 10% citric acid (100 ml×1). The organic layer was dried over sodium sulfate, and the solvent was evaporated. The resulting residue was subjected twice to a silica gel thin layer chromatography (methanol:chloroform=5:95), and the resulting silica gel was collected and extracted with a solvent system of methanol:chloroform=1:9. A 5 ml portion of concentrated hydrochloric acid was added dropwise to the thus obtained compound under ice cooling, followed by 10 minutes of stirring. After completion of the reaction, the reaction solution was adjusted to pH 12 with sodium hydroxide aqueous solution and then to pH 7.4 with hydrochloric acid, followed by extraction with chloroform (50 ml×3). The organic layers were combined and dried over sodium sulfate, and then the solvent was evaporated. Thereafter, the resulting residue was recrystallized from liquid ammonia-2-propanol to yield 96 mg (37%) of the title compound.

Melting point: 180°–181° C.

$[\alpha]_D^{25}$=−242.26, (c=0.265, 1N sodium hydroxide aqueous solution)

$^1$H-NMR (400 MHz, 0.1N NaOD) δ: 0.54–0.65 (4H, m), 1.37–1.64 (3H, m), 1.88–1.98 (1H, m), 2.33 (3H, s), 2.75–2.87 (1H, m), 3.29–3.48 (1H, m), 3.51–3.64 (2H, m), 3.71–3.83 (2H, m), 4.80–4.91 and 5.03–5.07 (1H, m), 8.18 (1H, s).

Elementary analysis for $C_{21}H_{23}F_2N_4O_3$ Calcd.: C 56.63 H 5.43 N 12.58 Found: C 56.57 H 5.31 N 12.44

A 449 mg (1.2 mmol) portion of (3R)-1-benzyloxycarbonyl-3-[1-(N-tert-butoxycarbonyl-N-methyl)aminocyclopropyl]-pyrrolidine was dissolved in 10 ml of methanol to which was subsequently added 100 mg of 5% palladium-carbon to carry out 1 hour of hydrogenation under normal pressure with warning by an infrared lamp light. After completion of the reaction, 5% palladium-carbon was removed by filtration and methanol was evaporated. The resulting residue was dissolved in 10 ml of dimethyl sulfoxide to which were subsequently added 0.174 ml (1.25 mmol) of triethylamine and 217 mg (0.6 mmol) of 6,7-difluoro-[(1R,2S)-2-fluorocyclopropyl]-1,4-dihydro-8-methoxy-4-oxoquinoline-3-carboxylic acid $BF_2$ chelate, followed by 5 hours of stirring at room temperature. After completion of the reaction, dimethyl sulfoxide was evaporated, the resulting residue was mixed with water, and the thus formed crystals were collected by filtration and washed with water (10 ml×3). The thus obtained crystals were dissolved in a mixed solvent consisting of 20 ml of methanol and 5 ml of water, and the solution was mixed with 0.3 ml of triethylamine and heated under reflux for 15.5 hours. After completion of the reaction, methanol was evaporated, and the reaction solution was mixed with 50 ml of water and extracted with chloroform (20 ml×2). The organic layers were combined, washed with 10% citric acid (100 ml×2) and dried over sodium sulfate, and the solvent was evaporated. A 5 ml portion of concentrated hydrochloric acid was added dropwise to the resulting residue under ice cooling, followed by 10 minutes of stirring at the same temperature. After completion of the reaction, the reaction solution was adjusted to pH 12 with sodium hydroxide aqueous solution and then to pH 7.4 with hydrochloric acid, followed by extraction with chloroform (50 ml×5). The organic layers were combined and dried over sodium sulfate, and then the solvent was evaporated. Thereafter, the resulting residue was recrystallized from methanol-ethanol to yield 215 mg (83%) of the title compound.

Melting point: 208°–209° C.

$[\alpha]_D^{25}$=−123.42, (c=0.525, 0.1N sodium hydroxide aqueous solution)

$^1$H-NMR (400 MHz, 0.1N NaOD) δ: 0.53–0.69 (4H, m), 1.32–1.59 (3H, m), 1.91–2.02 (1H, m), 2.34 (3H, s), 2.85–2.95 (1H, m), 3.29–3.38 (1H, m), 3.51–3.62 (2H, m), 3.57 (3H, s), 3.70–3.79 (1H, m), 3.98–4.07 (1H, m), 4.95–4.98 and 5.09–5.13 (1H, m), 7.66 (1H, d, J=14.23 Hz), 8.39 (1H, d, J=2.93).

Elementary analysis for $C_{22}H_{25}F_2N_3O_4$ Calcd.: C 60.96 H 5.81 N 9.69 Found: C 60.79 H 5.73 N 9.55

Inventive Example 18

6-Fluoro-1-[(1R,2S)-2-fluorocyclopropyl]-1,4-dihydro-8-methyl-7-[(3R)-3-(1-methylaminocyclopropyl)-1-pyrrolidinyl]-4-oxoquinoline-3-carboxylic acid

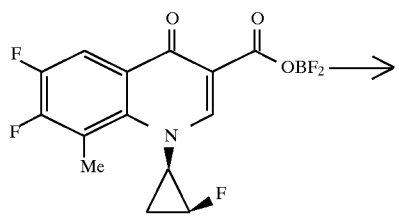

A 749 mg (2.0 mmol) portion of (3R)-1-benzyloxycarbonyl-3-[1-(N-tert-butoxycarbonyl-N-methyl)aminocyclopropyl]-pyrrolidine was dissolved in 10 ml of methanol to which was subsequently added 200 mg of 5% palladium-carbon to carry out 1 hour of hydrogenation under normal pressure with warming by an infrared lamp light. After completion of the reaction, 5% palladium-carbon was removed by filtration and methanol was evaporated. The resulting residue was dissolved in 5 ml of sulfolane to which were subsequently added 0.279 ml (2.0 mmol) of triethylamine and 345 mg (1.0 mmol) of 6,7-difluoro-[(1R,2S)-2-fluorocyclopropyl]-1,4-dihydro-8-methyl-4-oxoquinoline-3-carboxylic acid $BF_2$ chelate, followed by 11 days of stirring at room temperature. After completion of the reaction, the reaction solution was mixed with 50 ml of water, and the thus formed crystals were collected by filtration and washed with water (10 ml×2). The thus obtained crystals were dissolved in 32 ml of methanol and 8 ml of water, and the solution mixed with 0.5 ml of triethylamine and heated under reflux for 18 hours. After completion of the reaction, methanol was evaporated and the resulting residue was mixed with 200 ml of chloroform and washed with 10% citric acid (100 ml×1). The organic layer was dried over sodium sulfate, and the solvent was evaporated. The resulting residue was subjected to a silica gel thin layer chromatography (methanol:chloroform=1:9), and the resulting silica gel was collected and extracted with a mixed solvent of methanol:chloroform=1:9. A 5 ml portion of concentrated hydrochloric acid was added dropwise to the thus obtained compound under ice cooling, followed by 30 minutes of stirring at the same temperature. After completion of the reaction, the reaction solution was adjusted to pH 12 with sodium hydroxide aqueous solution and then to pH 7.4 with hydrochloric acid, followed by extraction with chloroform (100 ml×3). The organic layers were combined and dried on sodium sulfate, and then the solvent was evaporated. Thereafter, the resulting residue was recrystallized from methanol-ethanol to yield 124 mg (30%) of the title compound.

Melting point: 211°–212° C.

$[\alpha]_D^{25} = -330.18°$ (c=0.275, methanol)

$^1$H-NMR (400 MHz, 0.1N NaOD) δ: 0.51–0.67 (4H, m), 1.20–1.35 (1H, m), 1.43–1.68 (2H, m), 1.94–2.02 (1H, m), 2.32 (3H, s), 2.46 (3H, s), 2.89–2.98 (1H, m), 3.30–3.42 (3H, m), 3.75–3.83 (1H, m), 4.05–4.13 (1H, m), 4.90–4.93 and 5.03–5.10 (1H, m), 7.66 (1H, d, J=14.65 Hz), 8.41 (1H, d, J=3.42 Hz).

Elementary analysis for $C_{22}H_{25}F_2N_3O_3$ Calcd.: C 63.30 H 6.04 N 10.07 Found: C 62.97 H 6.25 N 9.91

Inventive Example 19

5-Amino-7-[(3R)-3-(1-ethylaminocyclopropyl)-1-pyrrolidinyl)]-6,8-difluoro-1-[(1R,2S)-2-fluorocyclopropyl]-1,4-dihydro-4-oxoquinoline-3-carboxylic acid

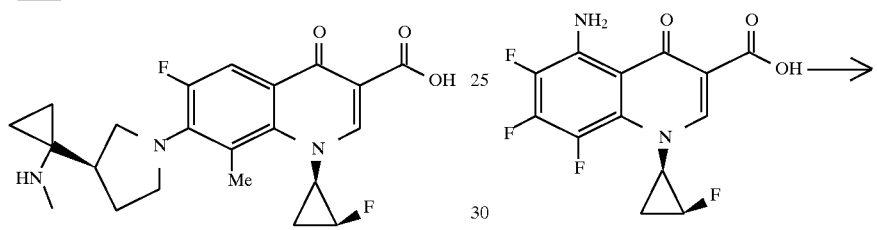

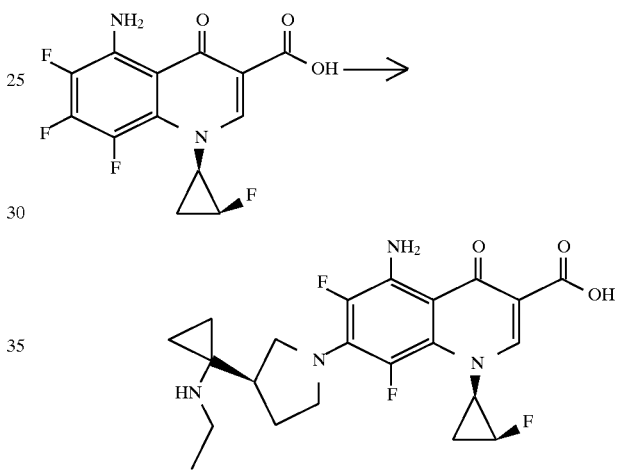

A 414 mg (1.07 mmol) portion of (3R)-1-benzyloxycarbonyl-3-[1-(N-tert-butoxycarbonyl-N-ethyl)aminocyclopropyl]pyrrolidine was dissolved in 15 ml of methanol to which was subsequently added 200 mg of 5% palladium-carbon to carry out 1.5 hours of hydrogenation under normal pressure with warming by an infrared lamp. After completion of the reaction, 5% palladium-carbon was removed by filtration and methanol was evaporated. The resulting residue was dissolved in 10 ml of acetonitrile to which were subsequently added 1 ml of triethylamine and 225 mg (0.71 mmol) of 5-amino-6,7,8-trifluoro-[(1R,2S)-2-fluorocyclopropyl]-1,4-dihydro-4-oxoquinoline-3-carboxylic acid, followed by 18 hours of heating under reflux. After completion of the reaction, acetonitrile was evaporated, and the resulting residue was mixed with 100 ml of chloroform and washed with 10% citric acid (100 ml×1). The organic layer was dried over sodium sulfate, and the solvent was evaporated. A 5 ml portion of concentrated hydrochloric acid was added dropwise to the resulting residue under ice cooling, followed by 1 hour of stirring. After completion of the reaction, the reaction solution was mixed with 10 ml of water and washed with dichloromethane (15 ml×1). The aqueous layer was adjusted to pH 12 with sodium hydroxide aqueous solution and then to pH 7.4 with hydrochloric acid, followed by extraction with chloroform (50 ml×3). The organic layers were combined and dried over sodium sulfate, and then the solvent was evaporated. Thereafter, the resulting residue was recrystallized from liquid ammonia-2-propanol to yield 243 mg (76%) of the title compound.

Melting point: 151°–152° C.

$[\alpha]_D^{25}$=−116.82, (c=0.315, 0.1N sodium hydroxide aqueous solution)

$^1$H-NMR (400 MHz, 0.1N NaOD) δ: 0.51–0.69 (4H, m), 1.04 (3H, t, J=7.32 Hz), 1.37–1.62 (3H, m), 1.92–1.99 (1H, m), 2.71 (2H, q, J=7.32 Hz), 2.78–2.88 (1H, m), 3.30–3.39 (1H, m), 3.53–3.64 (2H, m), 3.72–3.85 (2H, m), 4.85–4.92 and 5.03–5.07 (1H, m), 8.19 (1H, s).

Elementary analysis for $C_{22}H_{25}F_3N_4O_3 \cdot 1/4H_2O$ Calcd.: C 58.08 H 5.65 N 12.31 Found: C 58.23 H 5.89 N 11.98

Inventive Example 20

5-Amino-6,8-difluoro-1-[(1R,2S)-2-fluorocyclopropyl]-1,4-dihydro-7-[(3R)-3-[1-(2-hydroxyethyl)aminocyclopropyl]-1-pyrrolidinyl]-4-oxoquinoline-3-carboxylic acid

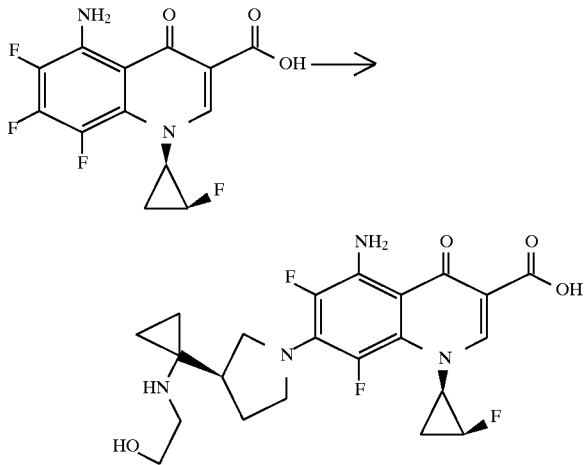

A 332 mg (0.67 mmol) portion of (3R)-1-benzyloxycarbonyl-3-[1-[N-(2-benzyloxyethyl)-N-tert-butoxycarbonyl]-aminocyclopropyl]pyrrolidine was dissolved in 20 ml of methanol to which was subsequently added 100 mg of 5% palladium-carbon to carry out 24 hours of hydrogenation under a pressure of 7 kg/cm² with warming by an infrared lamp light. After completion of the reaction, 5% palladium-carbon was removed by filtration and methanol was evaporated. The resulting residue was dissolved in 10 ml of acetonitrile to which were subsequently added 1 ml of triethylamine and 177 mg (0.56 mmol) of 5-amino-6,7,8-trifluoro-[(1R,2S)-2-fluorocyclopropyl]-1,4-dihydro-4-oxoquinoline-3-carboxylic acid, followed by 23 hours of heating under reflux. After completion of the reaction, acetonitrile was evaporated and the resulting residue was mixed with 100 ml of chloroform and washed with 10% citric acid (100 ml×1). The organic layer was dried on sodium sulfate, and the solvent was evaporated. The resulting residue was subjected to a silica gel thin layer chromatography (methanol:chloroform=1:9), and the resulting silica gel was collected and extracted with a solvent system of methanol:chloroform=1:9. A 10 ml portion of concentrated hydrochloric acid was added dropwise to the thus obtained compound under ice cooling, followed by 30 minutes of stirring. After completion of the reaction, the reaction solution was washed with dichloromethane (10 ml×2). The aqueous layer was adjusted to pH 12 with sodium hydroxide aqueous solution and then to pH 7.4 with hydrochloric acid, followed by extraction with chloroform (100 ml×3). The organic layers were combined and dried on sodium sulfate, and then the solvent was evaporated. Thereafter, the resulting residue was recrystallized from liquid ammonia-ethanol to yield 97 mg (36%) of the title compound.

Melting point: 198°–200° C.

$[\alpha]_D^{22.5}$=−141.49, (c=0.335, 0.1N sodium hydroxide aqueous solution)

$^1$H-NMR (400 MHz, 0.1N NaOD) δ: 0.58–0.66 (4H, m), 1.45–1.60 (3H, m), 1.92–1.97 (1H, m), 2.82–2.88 (3H, m), 3.31–3.38 (1H, m), 3.55–3.69 (4H, m), 3.75–3.83 (2H, m), 4.85–4.92 and 5.03–5.08 (1H, m), 8.19 (1H, s).

Elementary analysis for $C_{22}H_{25}F_3N_4O_4 \cdot 1/4H_2O$ Calcd.: C 56.11 H 5.46 N 11.90 Found: C 56.38 H 5.37 N 11.75

Inventive Example 21

6-Fluoro-1-[(1R,2S)-2-fluorocyclopropyl]-1,4-dihydro-7-[(3R)-3-[1-(2-hydroxyethyl)aminocyclopropyl]-1-pyrrolidinyl]-8-methoxy-4-oxoquinoline-3-carboxylic acid

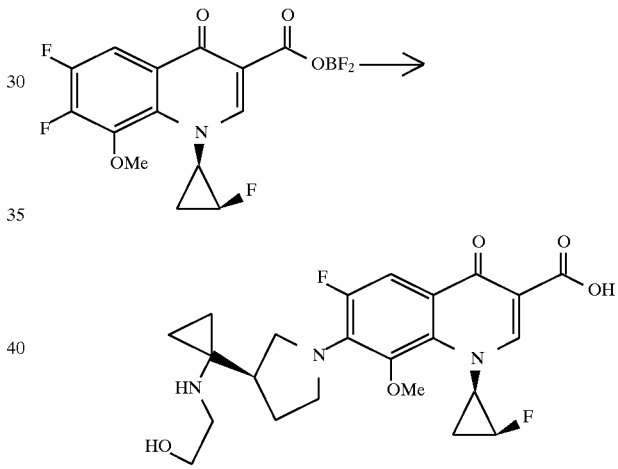

A 210 mg (0.78 mmol) portion of (3R)-3-[1-(2-hydroxyethyl)aminocyclopropyl]pyrrolidine was dissolved in 10 ml of dimethyl sulfoxide to which was subsequently added 0.109 ml (0.78 mmol) of triethylamine and 231 mg (0.64 mmol) of 6,7-difluoro-[(1R,2S)-2-fluorocyclopropyl]-1,4-dihydro-8-methoxy-4-oxoquinoline-3-carboxylic acid $BF_2$ chelate, followed by 20 hours of stirring at room temperature. After completion of the reaction, dimethyl sulfoxide was evaporated, the resulting residue was mixed with water and the thus formed crystals were collected by filtration and washed with water (10 ml×2). The thus obtained crystals were dissolved in 16 ml of methanol and 4 ml of water, and the solution was mixed with 1 ml of triethylamine and heated under reflux for 3 hours. After completion of the reaction, methanol was evaporated and the resulting residue was mixed with 100 ml of chloroform and washed with 10% citric acid (100 ml×2). The organic layer was dried over sodium sulfate, and the solvent was evaporated. The resulting residue was subjected to a silica gel thin layer chromatography (methanol:chloroform=1:9), and the resulting silica gel was collected and extracted with a solvent system of methanol:chloroform=1:9. A 5 ml portion of concentrated hydrochloric acid was added dropwise to the thus obtained compound under ice cooling, followed by 30 minutes of stirring at the same temperature. After completion of the reaction, the reaction solution was washed with dichloromethane (20 ml×1). The aqueous layer was adjusted to pH 12 with sodium hydroxide aqueous solution and then to pH 7.4 with hydrochloric acid, followed by extraction with chloroform (50 ml×3). The organic layers were combined and dried over sodium sulfate, and then the solvent was evaporated. Thereafter, the resulting residue was recrystallized from liquid ammonia-2-propanol to yield 120 mg (40%) of the title compound.

Melting point: 153°–155° C.

$[\alpha]_D^{25.4}$=–106.66, (c=0.270, 0.1N sodium hydroxide aqueous solution)

$^1$H-NMR (400 MHz, 0.1N NaOD) δ: 0.55–0.67 (4H, m), 1.33–1.43 (1H, m), 1.48–1.62 (2H, m), 1.94–2.04 (1H, m), 2.82–2.94 (3H, m), 3.29–3.36 (1H, m), 3.51–3.61 (2H, m), 3.57 (3H, s), 3.66 (2H, t, J=5.86 Hz), 3.66–3.78 (1H, m), 3.98–4.05 (1H, m), 4.91–4.95 and 5.07–5.11 (1H, m), 7.65 (1H, d, J=14.16 Hz), 8.39 (1H, d, J=2.93 Hz).

Elementary analysis for $C_{23}H_{27}F_2N_3O_5$ Calcd.: C 59.60 H 5.87 N 9.07 Found: C 59.34 H 6.03 N 8.84

Inventive Example 22

6-Fluoro-1-[(1R,2S)-2-fluorocyclopropyl]-1,4-dihydro-7-[(3R)-3-[1-(2-hydroxyethyl)aminocyclopropyl]-1-pyrrolidinyl]-8-methyl-4-oxoquinoline-3-carboxylic acid

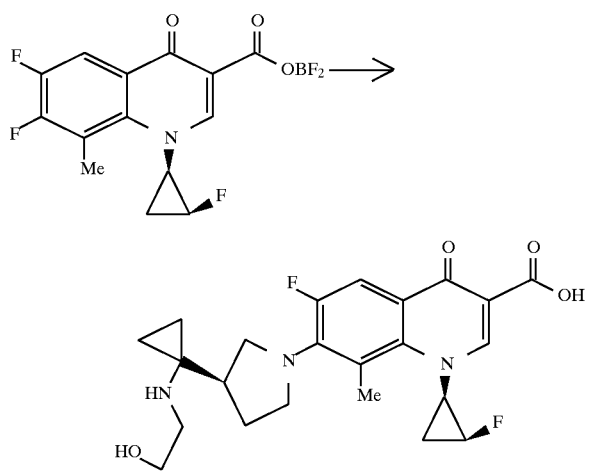

A 203 mg (0.74 mmol) portion of (3R)-3-[1-(2-hydroxyethyl)aminocyclopropyl]pyrrolidine was dissolved in 2 ml of sulfolane to which was subsequently added 0.082 ml (0.6 mmol) of triethylamine and 206 mg (0.6 mmol) of 6,7-difluoro-[(1R,2S)-2-fluorocyclopropyl]-8-methyl-1,4-dihydro-4-oxoquinoline-3-carboxylic acid $BF_2$ chelate, followed by 7 days of stirring at room temperature. After completion of the reaction, the reaction mixture was mixed with 100 ml of chloroform and washed with 10% citric acid (100 ml×1). The organic layer was dried over sodium sulfate, and the solvent was evaporated. The resulting residue was dissolved in 16 ml of methanol and 4 ml of water, and the solution was mixed with 1 ml of triethylamine and heated under reflux for 3 hours. After completion of the reaction, methanol was evaporated and the resulting residue was mixed with 100 ml of chloroform and washed with 10% citric acid (100 ml×1). The organic layer was dried over sodium sulfate, and the solvent was evaporated. The resulting residue was subjected to a silica gel thin layer chromatography (methanol:chloroform=1:9), and the resulting silica gel was collected and extracted with a solvent system of methanol:chloroform=1:9. A 2 ml portion of concentrated hydrochloric acid was added dropwise to the thus obtained compound under ice cooling, followed by 30 minutes of stirring at the same temperature. After completion of the reaction, the reaction solution was washed with dichloromethane (20 ml×1). The water layer was adjusted to pH 12 with sodium hydroxide aqueous solution and then to pH 7.4 with hydrochloric acid, followed by extraction with chloroform (50 ml×3). The organic layers were combined and dried over sodium sulfate, and then the solvent was evaporated. Thereafter, the resulting residue was recrystallized from liquid ammonia-ethanol to yield 63 mg (23%) of the title compound.

Melting point: 168°–170° C.

$[\alpha]_D^{25.2}$=–236.47, (c=0.170, 0.1N sodium hydroxide aqueous solution)

$^1$H-NMR (400 MHz, 0.1N NaOD) δ: 0.55–0.67 (4H, m), 1.18–1.25 (1H, m), 1.42–1.69 (2H, m), 1.92–1.99 (1H, m), 2.43 (3H, s), 2.82–2.94 (3H, m), 3.22–3.34 (3H, m), 3.65 (2H, t, J=5.86 Hz), 3.69–3.79 (1H, m), 4.03–4.09 (1H, m), 4.90–4.95 and 5.07–5.11 (1H, m), 7.65 (1H, d, J=14.16 Hz), 8.43 (1H, d, J=2.93 Hz).

Elementary analysis for $C_{23}H_{27}F_2N_3O_4$ Calcd.: C 61.74 H 6.08 N 9.39 Found: C 61.68 H 6.19 N 9.31

Inventive Example 23

5-Amino-7-[3-(1-aminocyclobutyl)-1-pyrrolidinyl]-6,8-difluoro-1-[(1R,2S)-2-fluorocyclopropyl]-1,4-dihydro-4-oxoquinoline-3-carboxylic acid (fr. 1)

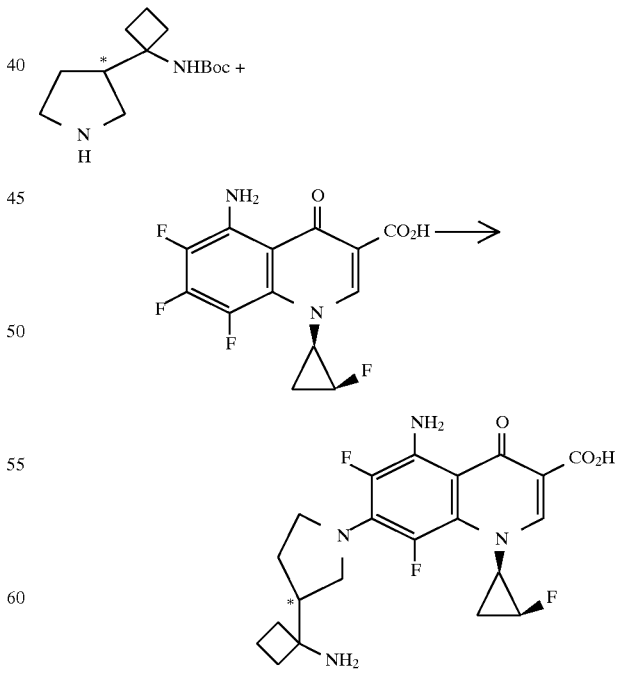

A 136 mg (0.57 mmol) portion of 3-(1-tert-butoxycarbonylaminocyclopropyl)pyrrolidine (fr.1) was suspended in 10.0 ml of acetonitrile to which was subsequently added 120 mg (0.38 mmol) of 5-amino-6,7,8-trifluoro-[(1R,2S)-2-fluorocyclopropyl]-1,4-dihydro-4-oxoquinoline-3-carboxylic acid and 0.79 ml (3.79 mmol) of triethylamine, followed by overnight heating under reflux. After evaporation of the solvent, the resulting residue was mixed with chloroform, washed with water, 10% citric acid aqueous solution and saturated brine in that order, and then dried over anhydrous sodium sulfate, followed by evaporation of the solvent. To this was added 2 ml of concentrated hydrochloric acid, followed by 2 hours of stirring at room temperature. The reaction solution was mixed with 10 ml of water, washed with chloroform and then neutralized with sodium hydroxide aqueous solution. This was extracted with chloroform and dried over sodium sulfate, and then the solvent was evaporated. Thereafter, the resulting residue was recrystallized from 2-propanol to yield 29 mg (15%) of the title compound as a yellow solid.

Melting point: 181°–183° C. (decomposition)

$^1$H-NMR (0.1 N-NaOD) δ: 1.53–1.72 (4H, m), 1.81–1.91 (3H, m), 1.98–2.13 (3H, m), 2.25–2.33 (1H, m), 3.42–3.60 (3H, m), 3.68–3.80 (2H, m), 4.81–5.03 (1H, m), 8.25 (1H, s).

Elementary analysis for $C_{21}H_{23}F_3N_4O_3 \cdot 1/4H_2O$ Calcd.: C 57.20 H 5.37 N 12.71 Found: C 57.09 H 5.34 N 12.38

Inventive Example 24

5-Amino-7-[3-(1-aminocyclobutyl)-1-pyrrolidinyl]-6,8-difluoro-1-[(1R,2S)-2-fluorocyclopropyl]-1,4-dihydro-4-oxoquinoline-3-carboxylic acid (fr. 2)

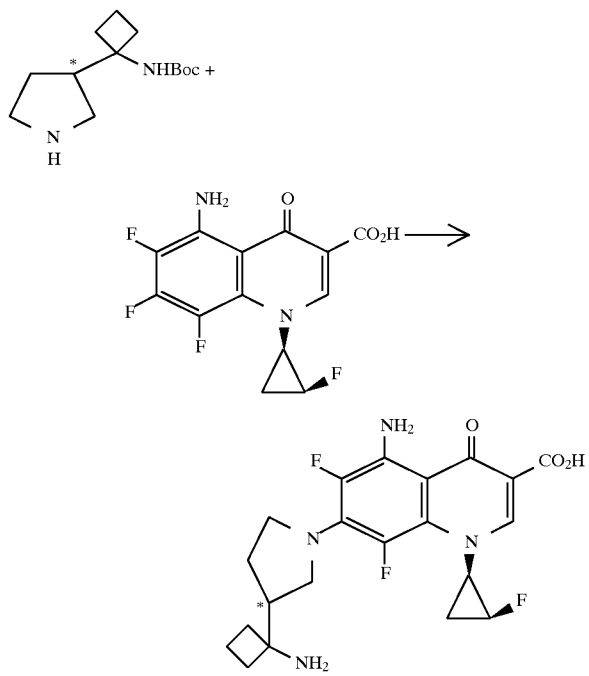

A 242 mg (1.00 mmol) portion of 3-(1-tert-butoxycarbonylaminocyclopropyl)pyrrolidine (fr.2) was suspended in 10.0 ml of acetonitrile to which was subsequently added 212 mg (0.67 mmol) of 5-amino-6,7,8-trifluoro-[(1R,2S)-2-fluorocyclopropyl]-1,4-dihydro-4-oxoquinoline-3-carboxylic acid and 1.40 ml (6.70 mmol) of triethylamine, followed by overnight heating under reflux. After evaporation of the solvent, the resulting residue was mixed with chloroform, washed with water, 10% citric acid aqueous solution and saturated brine in that order, and then dried over anhydrous sodium sulfate, followed by evaporation of the solvent. Thereto was added 2 ml of concentrated hydrochloric acid, followed by 2 hours of stirring at room temperature. The reaction solution was mixed with 10 ml of water, washed with chloroform and then neutralized with sodium hydroxide aqueous solution. This was extracted with chloroform and dried over sodium sulfate, and then the solvent was evaporated. Thereafter, the resulting residue was recrystallized from ethanol-diisopropyl ether to yield 292 mg (37%) of the title compound as a yellow solid.

Melting point: 133°–139° C.

$^1$H-NMR (0.1 N-NaOD) δ: 1.46–1.68 (4H, m), 1.81–1.86 (3H, m), 1.94–1.99 (1H, m), 2.05–2.10 (2H, m), 2.27–2.31 (1H, m), 3.47–3.54 (3H, m), 3.67–3.71 (2H, m), 3.86–5.02 (1H, m), 8.19 (1H, s).

Elementary analysis for $C_{21}H_{23}F_3N_4O_3 \cdot H_2O$ Calcd.: C 55.50 H 5.54 N 12.33 Found: C 55.76 H 5.33 N 11.85

Inventive Example 25

7-[3-(1-Aminocyclobutyl-1-pyrrolidinyl]-6,8-difluoro-1-[(1R,2S)-2-fluorocyclopropyl]-1,4-dihydro-8-methoxy-4-oxoquinoline-3-carboxylic acid (fr. 2)

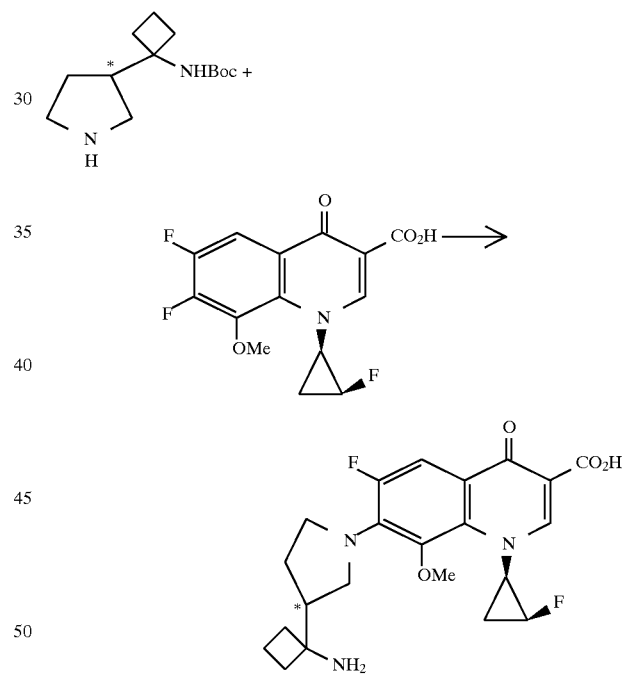

A 215 mg (0.89 mmol) portion of 3-(1-tert-butoxycarbonylaminocyclopropyl)pyrrolidine (fr.2) was suspended in 2.0 ml of dimethyl sulfoxide to which was subsequently added 215 mg (0.60 mmol) of 6,7,8-trifluoro-[(1R,2S)-2-fluorocyclopropyl]-1,4-dihydro-4-oxoquinoline-3-carboxylic acid and 249 μl (1.80 mmol) of triethylamine, followed by overnight stirring at room temperature. After evaporation of triethylamine, the resulting residue was mixed with water to collect the thus formed precipitate by filtration. This was dissolved in 10 ml of 90% methanol aqueous solution, and the solution was mixed with 2 ml of triethylamine and heated under reflux for 2 hours. After evaporation of the solvent, the resulting residue was mixed with chloroform, washed with 10% citric acid aqueous solution and saturated brine in that order, and then dried over anhydrous sodium sulfate, followed by evaporation of the solvent. To this was added 2 ml of concentrated hydrochloric acid, followed by 2 hours of stirring at room temperature. The reaction solution was mixed with 10 ml of water, washed with chloroform and then neutralized with sodium hydroxide aqueous solution. This was extracted with chloroform and dried over sodium sulfate, and then the solvent was evaporated. Thereafter, the resulting residue was recrystallized from ethanol-diisopropyl ether to yield 71 mg (27%) of the title compound as a yellow solid.

Melting point: 123°–139° C.

$^1$H-NMR (0.1 N-NaOD) δ: 1.33–1.40 (1H, m), 1.50–1.60 (1H, m), 1.68–1.79 (2H, m), 1.86–1.88 (3H, m), 2.03–2.07 (1H, m), 2.14 (2H, brs), 2.40–2.49 (1H, m), 3.50–3.52 (3H, m), 3.56 (3H, s), 3.67–3.71 (1H, m), 3.98–4.03 (1H, m), 7.66 (1H, d, J=14.6 Hz), 8.42 (1H, 2s).

Elementary analysis for $C_{22}H_{25}F_2N_3O_4 \cdot 3/4H_2O$ Calcd.: C 50.12 H 5.98 N 9.40 Found: C 58.94 H 5.70 N 9.13

Inventive Example 26

5-Amino-7-[3-(1-aminocyclopropyl-1-azetidinyl]-6,8-difluoro-1-[(1R,2S)-2-fluorocyclopropyl]-1,4-dihydro-4-oxoquinoline-3-carboxylic acid

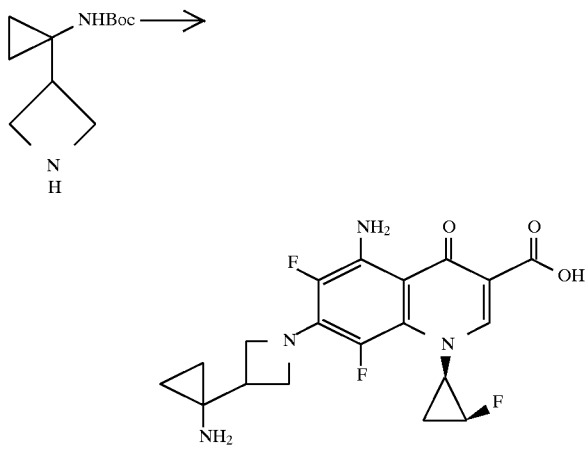

A 212 mg (1.00 mmol) portion of 3-(1-tert-butoxycarbonylaminocyclopropyl)azetidine was suspended in 10.0 ml of acetonitrile to which was subsequently added 210 mg (0.66 mmol) of 5-amino-6,7,8-trifluoro-[(1R,2S)-2-fluorocyclopropyl]-1,4-dihydro-4-oxoquinoline-3-carboxylic acid and 0.92 ml (6.60 mmol) of triethylamine, followed by 22 hours of heating under reflux. After evaporation of the solvent, the resulting residue was mixed with chloroform, washed with water, 10% citric acid aqueous solution and then dried over anhydrous sodium sulfate, followed by evaporation of the solvent. Thereto was added 2 ml of concentrated hydrochloric acid, followed by 2 hours of stirring at room temperature. The reaction solution was neutralized with sodium hydroxide aqueous solution and extracted with chloroform. The extract was dried over sodium sulfate and the solvent was evaporated. Thereafter, the resulting residue was purified by a preparative TLC (developed by the lower layer of chloroform:methanol:water=7:3:1), recrystallized from concentrated liquid ammonia-ethanol, and then washed with water and diethyl ether in that order to yield 108 mg (40%) of the title compound as a yellow solid.

Melting point: 188°–191° C. (decomposition)

$[α]_D^{25}$=36.44, (c=0.225, 1N sodium hydroxide aqueous solution)

$^1$H-NMR (0.1 N-NaOD) δ: 0.58 (4H, 2s), 1.54–1.61 (2H, m), 2.84–2.87 (1H, m), 3.78 (1H, m), 3.99(2H, m), 4.32 (2H, m), 8.1 (1H, s).

Elementary analysis for $C_{19}H_{19}F_3N_4O_3 \cdot 1/2\ H_2O$ Calcd.: C 54.68 H 4.83 N 13.42 Found: C 54.39 H 4.74 N 13.22

Inventive Example 27

5-Amino-7-[(3R)-3-(1-aminocyclopropyl)-1-pyrrolidinyl]-6-fluoro-1-[(1R,2S)-2-fluorocyclopropyl]-1,4-dihydro-8-methyl-4-oxoquinoline-3-carboxylic acid

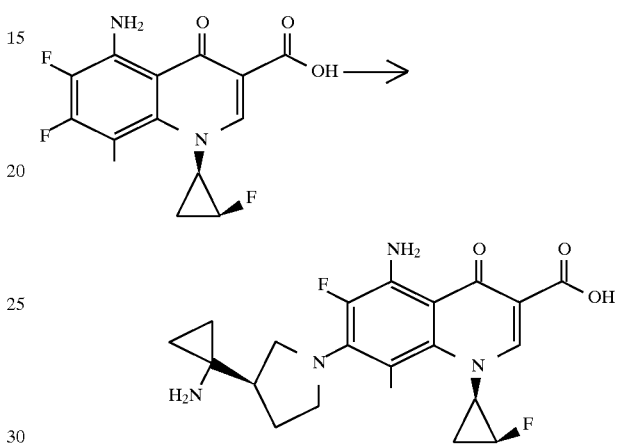

A 649 mg (1.8 mmol) portion of (3R)-1-benzyloxycarbonyl-3-(1-tert-butoxycarbonylaminomethyl-cyclopropyl)pyrrolidine was dissolved in 20 ml of methanol to which was subsequently added 200 mg of 5% (v/v) palladium-carbon to carry out 2 hours of hydrogenation under normal pressure with warming by an infrared lamp. After completion of the reaction, 5% (v/v) palladium-carbon was removed by filtration and methanol was evaporated. The resulting residue was dissolved in 20 ml of dimethyl sulfoxide to which were subsequently added 2 ml of triethylamine and 312 mg (1 mmol) of 5-amino-6,7-difluoro-[(1R,2S)-2-fluorocyclopropyl]-1,4-dihydro-8-methyl-4-oxoquinoline-3-carboxylic acid, followed by 18 hours of stirring at 150° C. After completion of the reaction, dimethyl sulfoxide was evaporated, and the resulting residue was mixed with 100 ml of chloroform and washed with 10% citric acid (100 ml×1) and saturated brine (100 ml×1) in that order. The organic layer was dried over anhydrous sodium sulfate, and the solvent was evaporated. A 10 ml portion of concentrated hydrochloric acid was added dropwise to the resulting residue under ice cooling, followed by 1 hour of stirring at room temperature. After completion of the reaction, the reaction solution was washed with dichloromethane (20 ml×1). The aqueous layer was adjusted to pH 12 with sodium hydroxide aqueous solution and then to pH 7.4 with hydrochloric acid, followed by extraction with chloroform (100 ml×4). The organic layers were combined and dried over anhydrous sodium sulfate, and then the solvent was evaporated. The resulting residue was subjected to a silica gel thin layer chromatography, and the silica gel collected after development by the lower layer of a mixture solvent system of chloroform:methanol:water=7:3:1 was extracted with the same solvent. Thereafter, the thus obtained crude product was recrystallized from chloroform-isopropyl ether to afford 101.5 mg (24%) of the title compound.

Melting point: 215°–216° C.

$[\alpha]_D^{25}$=−406.96, (c=0.115, 0.1N sodium hydroxide aqueous solution)

$^1$H-NMR (400 MHz, 0.1 N-NaOD) δ: 0.55 (4H, s), 1.09–1.18 (1H, m), 1.45–1.57 (1H, m), 1.61–1.74 (1H, m), 1.95–2.05 (1H, m), 2.16–2.25 (1H, m), 2.27 (3H, s), 3.24–3.37 (2H, m), 3.45–3.57 (1H, m), 3.68–3.80 (1H, m), 3.89–3.98 (1H, m), 4.85–4.91 and 5.02–5.07 (1H, m), 8.26 (1H, d, J=2.93 Hz).

Elementary analysis for $C_{21}H_{24}F_2N_4O_3 \cdot 1/2\ H_2O$ Calcd.: C 59.01 H 5.89 N 13.39 Found: C 59.35 H 5.85 N 12.83

Inventive Example 28

7-[(3R)-3-(1-Aminocyclopropyl)-1-pyrrolidinyl]-6,8-difluoro-1-[(1R,2S)-2-fluorocyclopropyl]-1,4-dihydro-5-hydroxy-4-oxoquinoline-3-carboxylic acid

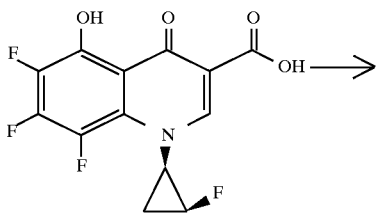

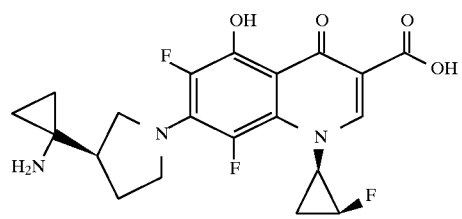

A 360 mg (1.00 mmol) portion of (R)-1-benzyloxycarbonyl-3-(1-tert-butoxycarbonylaminomethyl-cyclopropyl)pyrrolidine was dissolved in 10 ml of methanol to which was subsequently added 125 mg of 5% (v/v) palladium-carbon to carry out 3.5 hours of stirring at room temperature in a stream of hydrogen. After filtration through celite, methanol was evaporated. The resulting residue was mixed with 1 ml of triethylamine and 159 mg (0.50 mmol) of 6,7,8-trifluoro-[(1R,2S)-2-fluorocyclopropyl]-1,4-dihydro-5-hydroxy-4-oxoquinoline-3-carboxylic acid which has been dissolved in 10 ml of acetonitrile, and the thus prepared mixture was heated under reflux for 1 hour. After completion of the reaction, the reaction solution was mixed with 10% citric acid and extracted with chloroform (50 ml×3). The organic layer was dried over anhydrous sodium sulfate, and the solvent was evaporated. A 5 ml portion of concentrated hydrochloric acid was added dropwise to the resulting residue, followed by 1.5 hours of stirring at room temperature. After completion of the reaction, the reaction solution was adjusted to pH 12 with sodium hydroxide aqueous solution and then to pH 7.4 with hydrochloric acid, and the thus precipitated crystals were collected by filtration. The resulting filtrate was extracted with chloroform (100 ml×3). The organic layer was dried over anhydrous sodium sulfate and the solvent was evaporated. Thereafter, the resulting residue and the collected crystals were combined, and recrystallized from ethanol-liquid ammonia to yield 227 mg (82%) of the title compound.

Melting point: 199°–201° C.

$^1$H-NMR (400 MHz, 0.1N NaOD) δ: 0.55 (4H, s), 1.76–0.64 (3H, m), 2.05–1.94 (1H, m), 2.27–2.14 (1H, m), 3.58–3.38 (3H, m), 3.76–3.65 (1H, m), 3.87–3.76 (1H, m), 5.07–4.81 (1H, m), 8.12 (1H, s).

$[\alpha]_D^{21}$=−159.33 (c=0.625, 0.1N sodium hydroxide aqueous solution)

Elementary analysis for $C_{20}H_{20}F_3N_3O_4 \cdot 1/3 C_2H_5OH \cdot 3/4 H_2O$ Calcd.: C 54.89 H 5.24 N 9.29 Found: C 54.94 H 5.35 N 9.32

Inventive Example 29

5-Amino-6-fluoro-1-[2-(S)-fluoro-1-(R)-cyclopropyl]-8-methyl-7-[3-(R)-(1-methylaminocyclopropyl)-1-pyrrolidinyl]-1,4-dihydro-4-oxoquinoline-3-carboxylic acid hydrochloride

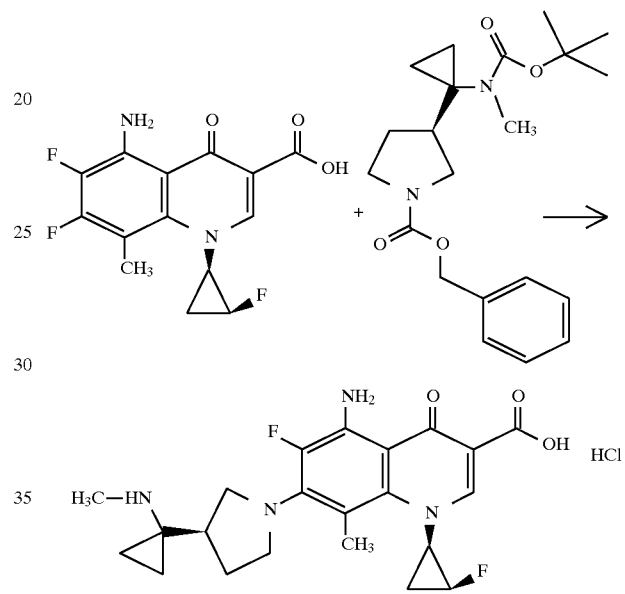

To a solution of 1-benzyloxycarbonyl-3-(R)-[1-(N-tert-butoxycarbonyl-N-methyl)amino-cyclopropyl]pyrrolidine (1.015 g, 2.710 mmol) in ethanol (40 ml) was added 5% palladium on activated carbon catalyst (moisture content 55.6%, 1.0 g). The mixture was stirred for 3 hr at room temperature under an initial hydrogen pressure of 4.5 kg/cm$^2$, and was then filtered through celite with ethanol to remove catalyst. The filtrate was concentrated in vacuo. To a solution of the resulting amorphous residue in dimethyl sulfoxide (7.5 ml) was added triethylamine (3.8 ml) and 5-amino-6,8-difluoro-1-(2-(S)-fluoro-1-(R)-cyclopropyl]-1,4-dihydro-4-oxoquinoline-3-carboxylic acid (351.1 mg, 1.124 mmol). The mixture was stirred at 150° C. for 15 hr under a nitrogen atmosphere. After cooling, the resulting mixture was concentrated in vacuo to remove dimethyl sulfoxide, and was then dissolved in chloroform (100 ml). The solution was washed with 10% aqueous citric acid (100 ml) and saturated aqueous sodium chloride (100 ml), dried over anhydrous magnesium sulfate, and subsequently concentrated in vacuo. To the resulting residue, at 0° C., was added 35% hydrochloric acid (10 ml) dropwise. The mixture was stirred at room temperature for 1 hr, and was then washed with dichloromethane (50 ml×2). The aqueous layer was adjusted to pH 7.4 with 1N sodium hydroxide solution, and was then extracted with chloroform (100 ml×4). The combined organic layers were dried over anhydrous magnesium sulfate, and subsequently concentrated in vacuo. The residue was purified by recrystallization with 2-propanol-diisopropyl ether. To a solution of the resulting precipitate in ethanol (20 ml) at 0° C. was added 1N hydrochloric acid (2.0 ml). The mixture was stirred at 0° C. for 5 min, and was then concentrated to dryness in vacuo. After diethyl ether was added to the residue, the resulting precipitate was purified by recrystallization with 2-propanol-ethanol, and was then dried at 80° C. for 37 hr in vacuo to give the desired product (288.3 mg, 54.7%) as a pale-yellow powder.

Melting point: 196.3°–198.6° C. (dec.)
$[\alpha]_D^{22.8} = -620.95°$ (c=0.422, $H_2O$)
$^1$H-NMR (400 MHz, $D_2O$) δ: 8.51 (1H, d, J=3.51 Hz), 5.02 and 4.91 (1H, m), 4.03–3.83 (1H, m), 3.60–3.41 (2H, m), 3.39–3.21 (1H, m), 2.93–2.83 (1H, m), 2.81 (3H, s), 2.21 (3H, s), 2.17–2.11 (1H, m), 1.83–1.61 (3H, m), 1.59–1.39 (1H, m), 1.19–1.09 (1H, m), 0.64–0.59 (4H, m).
Elemental analysis for $C_{22}H_{26}F_2N_4O_3 \cdot HCl$ Calcd.: C 53.27; H 6.08; N 11.30 Found: C 53.19; N 6.11; N 11.21

Reference Example J-1

Dimethyl4-(1,1-bisethoxycarbonylethyl)-3,5,6-trifluorophthalate

Dimethyl malonate (34.84 g, 0.20 mol) was added dropwise to a suspension of 80% NaH (8.0 g, 0.20 mol) in DMF (300 ml) under ice cooling. Dimethyl tetrafluorophthalate (53.23 g, 0.20 mol) was added to the mixture and the mixture was stirred for 24 h at room temperature. The reaction mixture was diluted with ethyl acetate (1000 ml). The solution was washed with water (3×500 ml), dried over anhydrous sodium sulfate, and evaporated to give 83.7 g of the title compound as a pale yellow oil.

$^1$H-NMR (400 MHz, $D_2O$) δ: 1.27 (6H, t, J=7 Hz), 1.85 (3H, s), 3.91 (3H, s), 3.97 (3H, s), 4.26 (2H, q, J=7 Hz), 4.27 (2H, q, J=7 Hz).

Reference Example J-2

4-(1-Carboxyethyl)-3,5,6-trifluorophthalic acid

A mixture of dimethyl 4-(1,1-bis-ethoxycarbonylethyl)-3,5,6-trifluorophthalate (12.9 g, 30.7 mmol), hydrochloric acid (120 ml), and acetic acid (120 ml, was refluxed for 24 h. The reaction mixture was concentrated to dryness to give 9.0 g of the title compound as colorless crystals.

$^1$H-NMR (400 Mhz, $D_2O$) δ: 1.45 (3H, d, J=7.4 Hz), 4.25–4.32 (2H, m).

Reference Example J-3

3-Ethyl-2,4,5-trifluorobenzoic acid

A mixture of 4-(1-carboxyethyl)-3,5,6-trifluorophthalic acid (14.9 g, 47.9 mmol), dimethylsulfoxide(100 ml), and triethylamine (30 ml) was heated at 140° C. for 4 days, and the reaction mixture was concentrated to dryness. To the residue was added 1N Hcl (100 ml), and the solution was extracted with ether. The extract was washed with brine, dried over anhydrous sodium sulfate, and then evaporated to yield 9.27 g of the title compound as pale yellow crystals.

$^1$H-NMR (400 MHz, $CDCl_3$) δ: 1.24 (3H, 7, J=7 Hz), 2.78 (2H, q, J=7 Hz), 7.67–7.73 (1H, m), 8.5–9.3 (1H, broad).

Reference Example K-1

Ethyl 5-amino-1-[(2S)-fluoro-(1R)-cyclopropyl]-1,4-dihydro-8-methoxy-4-oxoquinoline-3-carboxylate Ethyl 1-[(2S)-fluoro-(1R)-cyclopropyl]-1,4-dihydro-8-methoxy-5-nitro-4-oxoquinoline-3-carboxylate (1.72 g, 4.45 mmol) was dissolved in a mixture solvent of THF (40 ml) and EtOH (40 ml). Raney-Ni (1 ml) was added to the solution, and the mixture was stirred at room temperature for 1.5 h under hydrogen atmosphere. Raney-Ni catalyst was removed by filtration and the solvent was removed by evaporation. The residue was purified by silica gel column chromatography with 3% MeOH—$CHCl_3$ to give 1.33 g (84%) of the title compound.

$^1$H-NMR(400 MHz, $CDCl_3$) δ: 1.39 (3H, t, J=6.84 Hz), 1.40–1.60 (2H, m), 3.76–3.82 (1H, m), 3.86 (3H, s), 4.38 (2H, q, J=6.84 Hz), 4.72–4.76 (0.5H, m), 4.88–4.92 (0.5H, m), 8.40 (1H, s

Reference Example K-2

5-Amino-1-[(2S)-fluoro-(1R)-cyclopropyl]-1,4-dihydro-8-methoxy-4-oxoquinoline-3-carboxylic acid Ethyl 5-amino-1-[(2S)-fluoro-(1R)-cyclopropyl]-1,4-dihydro-8-methoxy-4-oxoquinoline-3-carboxylate (1.33 g, 3.73 mmol) was suspended in a mixture solvent of EtOH (10 ml) and MeOH (5 ml). To the suspension was added 1N NaOH (8 ml) and the mixture was stirred for 2.5 h at room temperature. The solvent was removed by evaporation, and conc. HCl was added to the residue under cooling with ice. The precipitated crystals were washed with water and EtOH to give 1.0 g (82%) of the title compound.

Inventive Example 30

5-Amino-7-(1-amino-3-azabicyclo[3.1.0]hex-3-yl)-6-fluoro-1-[(2S)-fluoro-(1R)-cyclopropyl]-1,4-dihydro-8-methoxy-4-oxoquinoline-3-carboxylic acid 1-tert-Butoxycarbonylamino-3-azabicyclo[3.1.0]hexane (Fr. 1) (350 mg, 1.77 mmol) and triethylamine (2 ml) were added to a solution of 5-amino-6,7-difluoro-1-[(2S)-fluoro-(1R)-cyclopropyl]-1,4-dihydro-8-methoxy-4-oxoquinoline-3-carboxylic acid (335 mg, 1.02 mmol) in DMSO (8 ml). The mixture was heated at 100° C. for 24 h, and the solvent was removed by evaporation. To the residue was added $CHCl_3$ (20 ml) and the insoluble material was removed by filtration. The filtrate was washed with 10% aqueous citric acid solution (10 ml×2), dried over anhydrous sodium sulfate and then evaporated to remove the solvent. To the residue was added conc. HCl (5 ml), and the mixture was stirred for 5 min at room temperature. The reaction mixture was washed with $CHCl_3$ (10 ml×2). The aqueous layer was neutralized to pH 7.3 with 20% aqueous NaOH solution and extracted with $CHCl_3$ (30 ml×3). The extract was dried over anhydrous $MgSO_4$ and the solvent was removed by evaporation to obtain 240 mg (58%) of the crude product. The crude product was recrystallized from EtOH-28% aqueous $NH_3$ solution to give 120 mg of the title compound.

Melting point: 219°–230° C. (decomposition)
$^1$H-NMR (400 MHz, 0.1 N-NaOD): δ: 0.62–0.65 (1H, m), 0.78–0.82 (1H, m), 1.21–1.52 (3H, m), 3.37 (3H, s), 3.42 (1H, d, J=9.28 Hz), 3.52 (2H, brs), 3.63–3.69 (1H, m), 3.83–3.90 (1H, m), 4.75–4.81 (0.5H, m), 4.90–4.95 (0.5H, m), 8.26 ( ) (1H, s).

Inventive Example 31

5-Amino-7-[(3R,1'S)-3-(1-methylaminoethyl)-1-pyrrolidinyl]-6-fluoro-1-[(1R,2S)-2-fluorocyclopropyl1-1,4-dihydro-8-methyl-4-oxoquinoline-3-carboxylic acid (3R,1'S)-3-[1-(N-Methyl)-tert-butoxycarbonylaminoethyl]-pyrrolidine (369 mg),5-amino- 1-[(1R,2S)-(2-fluorocyclopropyl]-6,7-difluoro-1,4-dihydro-8-methyl-4-oxoquinoline-3-carboxylic acid (312 mg), DMSO (5 ml) and triethylamine (5 ml) were mixed. The mixture was stirred at 120° C. for 3 days under a nitrogen atmosphere, and the solvent was removed by evaporation. To the residue was added conc. HCl (5 ml), and the mixture was stirred for 30 minutes and washed with $CHCl_3$. The aqueous layer was adjusted to pH 11 with an aqueous NaOH solution, adjusted to pH 7.40 with 1N HCl and extracted with $CHCl_3$ (500 ml×3). The extract was dried over anhydrous sodium sulfate and the solvent was removed by evaporation. The residue was recrystallized from isopropyl alcohol to give 125 mg of the title compound.

Elementary analysis for $C_{21}H_{26}F_2N_4O_3 \cdot 1/4 H_2O$ Calcd.: C 59.35 H 6.29 N 13.18 Found: C 59.41 H 6.21 N 12.95

INDUSTRIAL APPLICABILITY

The heterocyclic compounds of the present invention have an antibacterial activity against various kinds of bacteria, and therefore, are useful as antibacterial drugs.

TABLE 1

| Bacteria/compound (Ex. No.) | 1 | 2 | 3 | 8 |
|---|---|---|---|---|
| E. coli, NIHJ | ≦0.003 | ≦0.003 | ≦0.003 | ≦0.003 |
| S. flexneri, 2A 5503 | ≦0.003 | ≦0.003 | ≦0.003 | ≦0.003 |
| Pr. vulgaris, 08601 | 0.013 | ≦0.003 | ≦0.003 | 0.025 |
| Pr. mirabilis, IFO-3849 | 0.025 | 0.013 | 0.013 | 0.05 |
| Ser. marcescens, 10100 | 0.05 | 0.025 | 0.025 | 0.10 |
| Ps. aeruginosa, 32104 | 0.05 | 0.05 | 0.10 | 0.10 |
| Ps. aeruginosa, 32121 | 0.025 | 0.10 | 0.025 | 0.05 |
| Ps. maltophilia, IID-1275 | 0.025 | 0.05 | 0.05 | 0.10 |
| S. aureus, 209P | ≦0.003 | ≦0.003 | 0.006 | ≦0.003 |
| S. epidermidis, 56500 | 0.013 | 0.013 | 0.025 | 0.006 |
| Str. pyogenes, G-36 | 0.05 | 0.013 | 0.05 | ≦0.003 |
| Str. faeccalis, ATCC-19433 | 0.05 | 0.05 | 0.10 | 0.025 |
| S. aureus, 87037 | 0.10 | 0.10 | 0.20 | 0.05 |

| Bacteria/compound (Ex. No.) | 9 | 10 | 16 | 23 |
|---|---|---|---|---|
| E. coli, NIHJ | 0.006 | ≦0.003 | ≦0.003 | ≦0.003 |
| S. flexneri, 2A 5503 | 0.006 | ≦0.003 | ≦0.003 | ≦0.003 |
| Pr. vulgaris, 08601 | 0.013 | 0.006 | ≦0.003 | 0.013 |
| Pr. mirabilis, IFO-3849 | 0.10 | 0.006 | 0.013 | 0.025 |
| Ser. marcescens, 10100 | 0.10 | 0.025 | 0.05 | 0.05 |
| Ps. aeruginosa, 32104 | 0.10 | 0.05 | 0.05 | 0.10 |
| Ps. aeruginosa, 32121 | 0.05 | 0.025 | 0.05 | 0.025 |
| Ps. maltophilia, IID-1275 | 0.20 | 0.006 | 0.05 | 0.10 |
| S. aureus, 209P | ≦0.003 | ≦0.003 | ≦0.003 | ≦0.003 |
| S. epidermidis, 56500 | ≦0.003 | ≦0.003 | ≦0.003 | ≦0.003 |
| Str. pyogenes, G-36 | ≦0.003 | ≦0.003 | ≦0.003 | ≦0.003 |
| Str. faeccalis, ATCC-19433 | 0.025 | 0.013 | 0.025 | 0.013 |
| S. aureus, 87037 | 0.025 | 0.006 | 0.025 | 0.006 |

| Bacteria/compound (Ex. No.) | 28 | Ofloxacin |
|---|---|---|
| E. coli, NIHJ | ≦0.003 | 0.025 |
| S. flexneri, 2A 5503 | ≦0.003 | 0.05 |
| Pr. vulgaris, 08601 | 0.006 | 0.025 |
| Pr. mirabilis, IFO-3849 | 0.013 | 0.10 |
| Ser. marcescens, 10100 | 0.025 | 0.10 |
| Ps. aeruginosa, 32104 | 0.10 | 0.39 |
| Ps. aeruginosa, 32121 | 0.025 | 0.20 |
| Ps. maltophilia, IID-1275 | 0.006 | 0.39 |
| S. aureus, 209P | ≦0.003 | 0.20 |
| S. epidermidis, 56500 | ≦0.003 | 0.78 |
| Str. pyogenes, G-36 | ≦0.003 | 1.56 |
| Str. faeccalis, ATCC-19433 | 0.013 | 1.56 |
| S. aureus, 87037 | 0.006 | >6.25 |

We claim:

1. An $N_1$-(halogenocyclopropyl)-substituted pyridonecarboxylic acid derivative represented by formula (I):

wherein
X$^1$ represents a halogen atom or a;
X$^2$ represents a halogen atom;
R$^1$ represents a hydrogen atom, or an amino group;
R$^2$ is a group represented by formula (II):

wherein
R$^3$ and R$^4$ represent a hydrogen atom and n is an integer of 1;
A represents a partial structure of formula (III):

wherein
X$^3$ represents an alkyl group having 1 to 6 carbon atoms, a halogenomethyl group, an alkoxyl group having 1 to 6 carbon atoms or a halogenomethoxyl group,
R represents a hydrogen atom, a phenyl group, an acetoxymethyl group, a pivaloyloxymethyl group, an ethoxycarbonyl group, a choline group, a dimethylaminoethyl group, a 5-indanyl group, a phthalidynyl group, a 5-alkyl-2-oxo-1,3-dioxol-4-ylmethyl group, a 3-acetoxy-2-oxobutyl group, an alkyl group having 1 to 6 carbon atoms, an alkoxymethyl group having 2 to 7 carbon atoms or a phenylalkyl group composed of an alkylene group having 1 to 6 carbon atoms and a phenyl group; or a salt thereof.

2. The compound or a salt thereof according to claim 1, wherein said halogenocyclopropyl group in the formula (I) is a 1,2-cis-2-halogenocyclopropyl group.

3. The compound or a salt thereof according to claim 2, wherein R$^2$ in the formula (I) is a stereochemically pure substituent.

4. The compound or a salt thereof according to claim 1, 2 or 3, wherein said halogenocyclopropyl group in the formula (I) is a stereochemically pure substituent.

5. The compound or a salt thereof according to claim 4, wherein said halogenocyclopropyl group is a (1R,2S)-2-halogenocyclopropyl group.

6. The compound or a salt thereof according to claim 5, wherein X$^2$ is a fluorine atom.

7. An antibacterial composition, which comprises the compound of the formula (I) or a salt thereof as an active ingredient, together with a pharmaceutically acceptable carrier.

* * * * *